(12) United States Patent
Chu et al.

(10) Patent No.: US 7,427,635 B2
(45) Date of Patent: *Sep. 23, 2008

(54) SUBSTITUTED HYDANTOINS

(75) Inventors: Xin-Jie Chu, Livingston, NJ (US);
Nader Fotouhi, Basking Ridge, NJ (US); Nicholas J. S. Huby, Scotch Plains, NJ (US); Norman Kong, West Caldwell, NJ (US); Lee Apostle McDermott, Parlin, NJ (US); John Moliterni, Staten Island, NY (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 428 days.

This patent is subject to a terminal disclaimer.

(21) Appl. No.: 11/202,299

(22) Filed: Aug. 11, 2005

(65) Prior Publication Data

US 2006/0041146 A1 Feb. 23, 2006

Related U.S. Application Data

(60) Provisional application No. 60/682,997, filed on May 20, 2005, provisional application No. 60/602,175, filed on Aug. 17, 2004.

(51) Int. Cl.
*A61K 31/427* (2006.01)
*C07D 417/12* (2006.01)
(52) U.S. Cl. .................. 514/371; 548/146; 548/190; 548/193; 548/194; 548/195
(58) Field of Classification Search .............. 548/146, 548/190, 193, 194, 195; 514/365, 370, 371
See application file for complete search history.

(56) References Cited

U.S. PATENT DOCUMENTS 5,770,573 A  6/1998  Arrhenius et al.
6,583,288 B2 *  6/2003  Goodnow et al. ........ 546/274.4
6,784,298 B2 *  8/2004  Goodnow et al. ........... 548/195

FOREIGN PATENT DOCUMENTS

| WO | WO 99/01426 | 1/1999 |
|----|-------------|--------|
| WO | WO 01/83478 | 11/2001 |
| WO | WO 03/008365 A2 | 1/2003 |

OTHER PUBLICATIONS

J. M. English et al., *Trends in Pharm. Sci.* 2002, 23(1), 40.
J. L. Bos, *Cancer Res.* 1989, 49, 4682.
A. Bonni et al, *Science* 1999, 286, 1358.
H. Davies et al. *Nature* 2002, 417, 949.
R. Herrera et al. *Trends Mol. Med.* 2002, 8(4, Suppl.), S27.
C. F. Zheng et al., *J. Biol. Chem.* 1993, 268, 11435.
S. Cowley et al., *Cell* 1994, 77, 841.
R. Seger et al., *J. Biol. Chem.* 1992, 267, 14373.

* cited by examiner

*Primary Examiner*—Golam M Shameem
(74) *Attorney, Agent, or Firm*—George W. Johnston; Patricia S. Rocha-Tramaloni

(57) ABSTRACT

The present invention relates to compounds of the formula

I

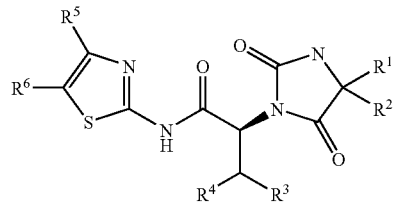

which are useful in treating diseases characterized by the hyperactivity of MEK.

Accordingly the compounds are useful in the treatment of diseases, such as, cancer, cognative and CNS disorders and inflammatory/autoimmune diseases.

5 Claims, No Drawings

SUBSTITUTED HYDANTOINS

PRIORITY TO RELATED APPLICATIONS

This application claims the benefit of Provisional Application(s) Ser. No. 60/682,997 filed May 20, 2005, and Ser. No. 60/602,175 filed Aug. 17, 2005.

FIELD OF THE INVENTION

The present invention relates to hydantoin derivatives as inhibitors of the two protein kinases commonly known as MEK1 and MEK2 for the treatment of human diseases such as cancer. MEK is a commonly used abbreviation for MAP kinase/ERK kinase which is in turn an abbreviation for mitogen activated protein/extracellular signal regulated kinase kinase. MEK is also sometimes referred to as MAPK kinase or MAP kinase.

BACKGROUND OF THE INVENTION

Cancer is a disease characterized by the proliferation of malignant cells and tumors which have the potential for unlimited growth, local expansion and systemic metastasis. This uncontrolled growth is derived from abnormalities in the signal transduction pathways and the response to various growth factors, which differ from those found in normal cells. The abnormalities include changes in the intrinsic activity or in the cellular concentration of one or more signaling proteins in the signaling cascade. These changes are frequently caused by genetic mutations or over expression of intracellular signaling proteins which can lead to spurious mitogenic signals within the cells.

The mitogen activated protein (MAP) kinase pathway represents one of the best characterized signaling pathways involved in the development and progression of human cancers (J. M. English et al., Trends in Pharm. Sci. 2002, 23(1), 40). This pathway, via the Ras/Raf/MEK/ERK signal cascade, is responsible for transmitting and amplifying mitogenic signals from the cell surface to the nucleus where activated transcription factors regulate gene expression and determine cell fate. The constitutive activation of this pathway is sufficient to induce cellular transformation. Dysregulated activation of the MAP kinase pathway due to aberrant receptor tyrosine kinase activation, Ras mutations or Raf mutations has frequently been found in human cancers, and represents a major factor determining abnormal growth control. In human malignances, Ras mutations are common, having been identified in about 30% of cancers (J. L. Bos, Cancer Res. 1989, 49, 4682). The Ras family of GTPase proteins (proteins which convert guanosine triphosphate to guanosine diphosphate) relay signals from activated growth factor receptors to downstream intracellular partners. Prominent among the targets recruited by active membrane-bound Ras are the Raf family of serine/threonine protein kinases. The Raf family is composed of three related kinases (A-, B- and C-Raf) that act as downstream effectors of Ras. Ras-mediated Raf activation in turn triggers activation of MEK1 and MEK2 (MAP/ERK kinases 1 and 2) which in turn phosphorylate ERK1 and ERK2 (extracellular signal-regulated kinases 1 and 2) on both tyrosine-185 and threonine-183. Activated ERK1 and ERK2 translocate and accumulate in the nucleus, where they can phosphorylate a variety of substrates, including transcription factors that control cellular growth and survival (A. Bonni et al, Science 1999, 286, 1358). Recently, B-Raf somatic mutations in the kinase domain were also found in 66% of malignant melanomas, and at a lower frequency in a wider range of human cancers (H. Davies et al. Nature 2002, 417, 949). Like mutated Ras, constitutively active mutated Raf can transform cells in vitro and induce malignancies in a variety of animal models (H. Davies et al., Nature 2002, 417, 949). Given the importance of the Ras/Raf/MEK/ERK pathway in the development of human cancers, the kinase components of this signaling cascade are emerging as potentially important targets for the modulation of disease progression in cancer and other proliferative diseases (R. Herrera et al. Trends Mol. Med. 2002, 8(4, Suppl.), S27).

MEK1 and MEK2 are members of a larger family of dual-specificity kinase (MEK1-7) that phosphorylate threonine and tyrosine residues of various MAP kinases. MEK1 and MEK2 are encoded by distinct genes, but they share high homology (80%) both within the C-terminal catalytic kinase domains and most of the N-terminal regulatory region (C. F. Zheng et al., J. Biol. Chem. 1993, 268, 11435). Oncogenic forms of MEK1 and 2 have not been found in human cancers. However, constitutive activation of MEK has been shown to result in cellular transformation (S. Cowley et al., Cell 1994, 77, 841). In addition to Raf, MEK can also be activated by other oncogenes as well. So far, the only known substrates of MEK1 and 2 are ERK1 and 2 (R. Seger et al., J. Biol. Chem. 1992, 267, 14373). This unusual substrate specificity in addition to the unique ability to phosphorylate both tyrosine and threonine residues places MEK1 and 2 at a critical point in the signal transduction cascade which allows them to integrate many extracellular signals into the MAPK pathway.

Previously reported studies with the MEK inhibitor 2-(2-chloro-4-iodo-phenylamino)-N-cyclopropylmethoxy-3,4-difluoro-benzamide, also known as CI-1040 (Pfizer Inc., described in PCT publication No. WO 99/01426) provides further evidence that MEK1 and 2 represent an attractive target for pharmacological intervention in cancer or other human diseases characterized by the hyperactivity of MEK and diseases regulated by the MAPK pathway.

Compounds related to the compounds of the present invention have previously been reported as glucokinase activators (F. Hoffmann-La Roche AG, PCT publication No. WO 01/83478). The compounds which have been previously reported were defined as containing a methylene spacer ($CH_2$ group) between the hydantoin ring and additional substituents which included an unsubstituted or a substituted aryl ring amongst other defined substituents. The compounds claimed in the present invention are defined to include compounds where there is no methylene spacer between the hydantoin ring and substituted or unsubstituted aryl or substituted or unsubstituted heteroaryl group rings.

SUMMARY OF THE INVENTION

This invention relates to at least one compound of the formula I

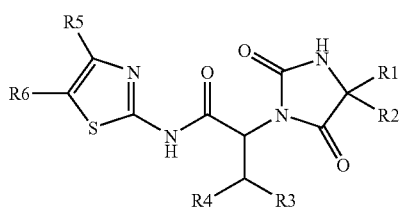

or pharmaceutically acceptable salts thereof, wherein $R^1$, $R^2$, $R^3$, $R^4$, $R^5$ and $R^6$ are described in this application. These compounds are believed to inhibit MEK 1/2, a dual specificity protein kinase which is an essential component of the MAP kinase signal transduction pathway and as such the compounds will have anti-hyperproliferative cellular activity.

DETAILED DESCRIPTION OF THE INVENTION

The present compounds are new compounds of the formula I

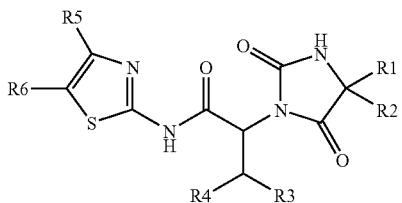

I wherein:
$R^1$ is selected from the group consisting of a substituted or unsubstituted aryl or a substituted or unsubstituted heteroaryl group;
$R^2$ is hydrogen
$R^3$ is selected from a mono- or di-alkyl group;
$R^4$ is selected from the group consisting of a substituted or unsubstituted aryl, hydroxyl, alkoxy, substituted alkoxy or a substituted or unsubstituted heteroaryl or alkyl group;
$R^5$ is selected from the group consisting of COOR, COR, CON(R7)$_2$ or CHOHR wherein R is alkyl or alkyl substituted by an alkoxy group; and
$R^6$ and $R^7$ are selected from hydrogen or an alkyl group or the pharmaceutically acceptable salts or esters or prodrugs thereof.

Preferred are compounds of formula I wherein $R^3$ is an alkyl group, $R^4$ is substituted or unsubstituted aryl and $R^6$ is hydrogen.

More preferred are compounds wherein $R^3$ is a methyl group and $R^4$ is phenyl.

Most preferred are compounds of the formulas:
(2S,3S)-N-(4-Acetyl-thiazol-2-yl)-2-[(R)-4-(4-methoxy-phenyl)-2,5-dioxo-imidazolidin-1-yl]-3-phenyl-butyramide;
(2S,3S)-N-(4-Acetyl-thiazol-2-yl)-2-[(R)-4-(4-hydroxy-phenyl)-2,5-dioxo-imidazolidin-1-yl]-3-phenyl-butyramide;
(2S,3S)-N-(4-Acetyl-thiazol-2-yl)-2-{(R)-4-[4-(2-hydroxy-ethoxy)-phenyl]-2,5-dioxo-imidazolidin-1-yl}-3-phenyl-butyramide;
(2S,3S)-N-(4-Acetyl-thiazol-2-yl)-2-{(R)-4-[4-(2-methoxy-ethoxy)-phenyl]-2,5-dioxo-imidazolidin-1-yl}-3-phenyl-butyramide;
(2S,3S)-N-(4-Acetyl-thiazol-2-yl)-2-((R)-4-{4-[2-(2-methoxy-ethoxy)-ethoxy]-phenyl}-2,5-dioxo-imidazolidin-1-yl)-3-phenyl-butyramide;
(2S,3S)-N-(4-Acetyl-thiazol-2-yl)-2-{(R)-4-[4-(2-ethoxy-ethoxy)-phenyl]-2,5-dioxo-imidazolidin-1-yl}-3-phenyl-butyramide;
(2S,3S)-N-(4-Acetyl-thiazol-2-yl)-2-{(R)-4-[4-(2-dimethylamino-ethoxy)-phenyl]-2,5-dioxo-imidazolidin-1-yl}-3-phenyl-butyramide; compound with trifluoro-acetic acid
(2S,3S)-N-(4-Acetyl-thiazol-2-yl)-2-{(R)-4-[4-(2-diethylamino-ethoxy)-phenyl]-2,5-dioxo-imidazolidin-1-yl}-3-phenyl-butyramide; compound with trifluoro-acetic acid
(2S,3S)-N-(4-Acetyl-thiazol-2-yl)-2-[(R)-4-(4-ethoxy-phenyl)-2,5-dioxo-imidazolidin-1-yl]-3-phenyl-butyramide;
(2S,3S)-N-(4-Acetyl-thiazol-2-yl)-2-{(S)-4-[4-(2-dimethylamino-ethoxy)-phenyl]-2,5-dioxo-imidazolidin-1-yl}-3-phenyl-butyramide; compound with trifluoro-acetic acid
(4-{1-[(1S,2S)-1-(4-Acetyl-thiazol-2-ylcarbamoyl)-2-phenyl-propyl]-2,5-dioxo-imidazolidin-4-yl}-phenyl)-phosphonic acid diethyl ester;
(2S,3S)-N-(4-Acetyl-thiazol-2-yl)-2-[4-(4-dimethylamino-phenyl)-2,5-dioxo-imidazolidin-1-yl]-3-phenyl-butyramide;
(2S,3S)-2-[(R)-4-(4-Methoxy-phenyl)-2,5-dioxo-imidazolidin-1-yl]-3-phenyl-pentanoic acid (4-acetyl-thiazol-2-yl)-amide;
(2S,3S)-2-[(R)-4-(4-Methoxy-phenyl)-2,5-dioxo-imidazolidin-1-yl]-3-phenyl-N-(4-propionyl-thiazol-2-yl)-butyramide;
(2S,3S)-2-[(R)-4-(2,3-Dihydro-benzo[1,4]dioxin-6-yl)-2,5-dioxo-imidazolidin-1-yl]-3-phenyl-N-(4-propionyl-thiazol-2-yl)-butyramide;
(2S,3S)-2-[(R)-4-(4-Ethoxy-phenyl)-2,5-dioxo-imidazolidin-1-yl]-3-phenyl-N-(4-propionyl-thiazol-2-yl)-butyramide;
(2S,3S)-2-[(R)-4-(4-Hydroxy-phenyl)-2,5-dioxo-imidazolidin-1-yl]-3-phenyl-N-(4-propionyl-thiazol-2-yl)-butyramide;
(2S,3S)-2-{(R)-4-[4-(2-Methoxy-ethoxy)-phenyl]-2,5-dioxo-imidazolidin-1-yl}-3-phenyl-N-(4-propionyl-thiazol-2-yl)-butyramide;
(2S,3S)-2-{(S)-4-[4-(2-Methoxy-ethoxy)-phenyl]-2,5-dioxo-imidazolidin-1-yl}-3-phenyl-N-(4-propionyl-thiazol-2-yl)-butyramide;
(2S,3S)-2-{(R)-4-[4-(2-Hydroxy-ethoxy)-phenyl]-2,5-dioxo-imidazolidin-1-yl}-3-phenyl-N-(4-propionyl-thiazol-2-yl)-butyramide;
(2S,3S)-2-((R)-4-{4-[2-(2-Methoxy-ethoxy)-ethoxy]-phenyl}-2,5-dioxo-imidazolidin-1-yl)-3-phenyl-N-(4-propionyl-thiazol-2-yl)-butyramide;
(2S,3S)-2-{(R)-4-[4-(2-Ethoxy-ethoxy)-phenyl]-2,5-dioxo-imidazolidin-1-yl}-3-phenyl-N-(4-propionyl-thiazol-2-yl)-butyramide;
(2S,3S)-2-{(R)-4-[4-(2-Dimethylamino-ethoxy)-phenyl]-2,5-dioxo-imidazolidin-1-yl}-3-phenyl-N-(4-propionyl-thiazol-2-yl)-butyramide; compound with trifluoro-acetic acid
(4-{(R)-2,5-Dioxo-1-[(1S,2S)-2-phenyl-1-(4-propionyl-thiazol-2-ylcarbamoyl)-propyl]-imidazolidin-4-yl}-phenoxymethyl)-phosphonic acid dimethyl ester;
(2S,3S)-N-(4-Isobutyryl-thiazol-2-yl)-2-{4-[4-(2-methoxy-ethoxy)-phenyl]-2,5-dioxo-imidazolidin-1-yl}-3-phenyl-butyramide;
(2S,3S)-N-(4-Isobutyryl-thiazol-2-yl)-2-[(R)-4-(4-methoxy-phenyl)-2,5-dioxo-imidazolidin-1-yl]-3-phenyl-butyramide;
(2S,3S)-2-{(S)-4-[4-(2-Dimethylamino-ethoxy)-phenyl]-2,5-dioxo-imidazolidin-1-yl}-3-phenyl-N-(4-propionyl-thiazol-2-yl)-butyramide; compound with trifluoro-acetic acid;
(2S,3S)-2-{2,5-Dioxo-4-[4-(2-piperidin-1-yl-ethoxy)-phenyl]-imidazolidin-1-yl}-3-phenyl-N-(4-propionyl-thiazol-2-yl)-butyramide;
(2S,3S)-2-{4-[4-(2-Morpholin-4-yl-ethoxy)-phenyl]-2,5-dioxo-imidazolidin-1-yl}-3-phenyl-N-(4-propionyl-thiazol-2-yl)-butyramide;

(2S,3S)-3-(3-Fluoro-phenyl)-2-{(R)-4-[4-(2-methoxy-ethoxy)-phenyl]-2,5-dioxo-imidazolidin-1-yl}-N-(4-propionyl-thiazol-2-yl)-butyramide;

(2S,3S)-2-[(R)-4-(4-Methoxy-3-methyl-phenyl)-2,5-dioxo-imidazolidin-1-yl]-3-phenyl-N-(4-propionyl-thiazol-2-yl)-butyramide;

(2S,3S)-2-{(S)-4-[4-(2-Hydroxy-ethoxy)-phenyl]-2,5-dioxo-imidazolidin-1-yl}-3-phenyl-N-(4-propionyl-thiazol-2-yl)-butyramide;

(2S,3S)-2-((R)-2,5-Dioxo-4-phenyl-imidazolidin-1-yl)-3-phenyl-N-(4-propionyl-thiazol-2-yl)-butyramide;

(2S,3S)-2-[4-(4-Dimethylamino-phenyl)-2,5-dioxo-imidazolidin-1-yl]-3-phenyl-N-(4-propionyl-thiazol-2-yl)-butyramide;

(2S,3S)-2-[4-(4-Morpholin-4-yl-phenyl)-2,5-dioxo-imidazolidin-1-yl]-3-phenyl-N-(4-propionyl-thiazol-2-yl)-butyramide;

(2S,3S)-2-{4-[4-(4-Hydroxy-piperidin-1-yl)-phenyl]-2,5-dioxo-imidazolidin-1-yl}-3-phenyl-N-(4-propionyl-thiazol-2-yl)-butyramide;

(2S,3S)-2-(4-{4-[(2-Methoxy-ethyl)-methyl-amino]-phenyl}-2,5-dioxo-imidazolidin-1-yl)-3-phenyl-N-(4-propionyl-thiazol-2-yl)-butyramide;

(2S,3S)-N-(4-Cyclopropanecarbonyl-thiazol-2-yl)-2-{(R)-4-[4-(2-methoxy-ethoxy)-phenyl]-2,5-dioxo-imidazolidin-1-yl}-3-phenyl-butyramide;

(2S,3S)-2-{4-[4-(2-Methoxy-ethoxy)-phenyl]-2,5-dioxo-imidazolidin-1-yl}-3-methyl-pentanoic acid (4-propionyl-thiazol-2-yl)-amide;

(2S,3R)-3-Benzyloxy-2-{(R)-4-[4-(2-methoxy-ethoxy)-phenyl]-2,5-dioxo-imidazolidin-1-yl}-N-(4-propionyl-thiazol-2-yl)-butyramide;

(2S,3S)-N-[4-(2-Methoxy-acetyl)-thiazol-2-yl]-2-[(R)-4-(4-methoxy-phenyl)-2,5-dioxo-imidazolidin-1-yl]-3-phenyl-butyramide;

2-{(2S,3S)-2-[(R)-4-(2,3-Dihydro-benzo[1,4]dioxin-6-yl)-2,5-dioxo-imidazolidin-1-yl]-3-phenyl-butyrylamino}-thiazole-4-carboxylic acid methyl ester;

2-[(2S,3S)-2-((R)-2,5-Dioxo-4-phenyl-imidazolidin-1-yl)-3-phenyl-butyrylamino]-thiazole-4-carboxylic acid methyl ester;

2-{(2S,3S)-2-[(R)-4-(4-Methoxy-phenyl)-2,5-dioxo-imidazolidin-1-yl]-3-phenyl-butyrylamino}-thiazole-4-carboxylic acid methyl ester;

2-{(2S,3S)-2-[(R)-4-(4-Hydroxy-phenyl)-2,5-dioxo-imidazolidin-1-yl]-3-phenyl-butyrylamino}-thiazole-4-carboxylic acid methyl ester;

2-((2S,3S)-2-{(R)-4-[4-(2-Methoxy-ethoxy)-phenyl]-2,5-dioxo-imidazolidin-1-yl}-3-phenyl-butyrylamino)-thiazole-4-carboxylic acid methyl ester;

2-((2S,3S)-2-{(R)-4-[4-(2-Hydroxy-ethoxy)-phenyl]-2,5-dioxo-imidazolidin-1-yl}-3-phenyl-butyrylamino)-thiazole-4-carboxylic acid methyl ester;

2-{(2S,3S)-2-[(R)-4-(4-Isopropoxy-phenyl)-2,5-dioxo-imidazolidin-1-yl]-3-phenyl-butyrylamino}-thiazole-4-carboxylic acid methyl ester;

2-{(2S,3S)-2-[(R)-4-(4-Methoxy-3-methyl-phenyl)-2,5-dioxo-imidazolidin-1-yl]-3-phenyl-butyrylamino}-thiazole-4-carboxylic acid methyl ester;

2-((2S,3S)-2-{(R)-4-[4-(Dimethoxy-phosphorylmethoxy)-phenyl]-2,5-dioxo-imidazolidin-1-yl}-3-phenyl-butyrylamino)-thiazole-4-carboxylic acid methyl ester;

2-{(2S,3S)-3-(2-Methoxy-phenyl)-2-[4-(4-methoxy-phenyl)-2,5-dioxo-imidazolidin-1-yl]-butyrylamino}-thiazole-4-carboxylic acid methyl ester;

2-((2S,3S)-3-(4-Fluoro-phenyl)-2-{(R)-4-[4-(2-methoxy-ethoxy)-phenyl]-2,5-dioxo-imidazolidin-1-yl}-butyrylamino)-thiazole-4-carboxylic acid methyl ester;

2-{(2S,3S)-2-[(R)-4-(4-Methoxy-phenyl)-2,5-dioxo-imidazolidin-1-yl]-3-methyl-pentanoylamino}-thiazole-4-carboxylic acid methyl ester;

2-[(2S,3S)-2-((R)-2,5-Dioxo-4-phenyl-imidazolidin-1-yl)-3-methyl-pentanoylamino]-thiazole-4-carboxylic acid methyl ester;

2-((2S,3S)-2-{(R)-4-[4-(2-Methoxy-ethoxy)-phenyl]-2,5-dioxo-imidazolidin-1-yl}-3-methyl-pentanoylamino)-thiazole-4-carboxylic acid methyl ester;

2-{(2S,3R)-3-Hydroxy-2-[(R)-4-(4-methoxy-phenyl)-2,5-dioxo-imidazolidin-1-yl]-butyrylamino}-thiazole-4-carboxylic acid methyl ester;

2-((2S,3R)-3-Hydroxy-2-{(R)-4-[4-(2-methoxy-ethoxy)-phenyl]-2,5-dioxo-imidazolidin-1-yl}-butyrylamino)-thiazole-4-carboxylic acid methyl ester;

2-((2S,3R)-3-tert-Butoxy-2-{(R)-4-[4-(2-methoxy-ethoxy)-phenyl]-2,5-dioxo-imidazolidin-1-yl}-butyrylamino)-thiazole-4-carboxylic acid methyl ester;

2-{(2S,3R)-3-Methoxy-2-[(R)-4-(4-methoxy-phenyl)-2,5-dioxo-imidazolidin-1-yl]-butyrylamino}-thiazole-4-carboxylic acid methyl ester;

2-((2S,3R)-3-Methoxy-2-{(R)-4-[4-(2-methoxy-ethoxy)-phenyl]-2,5-dioxo-imidazolidin-1-yl}-butyrylamino)-thiazole-4-carboxylic acid methyl ester;

2-((2S,3R)-3-Benzyloxy-2-{(R)-4-[4-(2-methoxy-ethoxy)-phenyl]-2,5-dioxo-imidazolidin-1-yl}-butyrylamino)-thiazole-4-carboxylic acid methyl ester;

2-((2S,3R)-3-(4-Chloro-benzyloxy)-2-{(R)-4-[4-(2-methoxy-ethoxy)-phenyl]-2,5-dioxo-imidazolidin-1-yl}-butyrylamino)-thiazole-4-carboxylic acid methyl ester 2-{(2S,3R)-2-[(R)-4-(4-Methoxy-phenyl)-2,5-dioxo-imidazolidin-1-yl]-3-methyl-pentanoylamino}-thiazole-4-carboxylic acid methyl ester 2-((2S,3R)-2-{(R)-4-[4-(2-Methoxy-ethoxy)-phenyl]-2,5-dioxo-imidazolidin-1-yl}-3-methyl-pentanoylamino)-thiazole-4-carboxylic acid methyl ester;

2-((2S,3R)-2-{(R)-4-[4-(2-Methoxy-ethoxy)-phenyl]-2,5-dioxo-imidazolidin-1-yl}-3-methyl-pentanoylamino)-thiazole-4-carboxylic acid methyl ester;

2-{(2S,3S)-2-[4-(4-Methanesulfonyl-phenyl)-2,5-dioxo-imidazolidin-1-yl]-3-phenyl-butyrylamino}-thiazole-4-carboxylic acid methyl ester;

2-{(S)-2-[(R)-4-(4-Methoxy-phenyl)-2,5-dioxo-imidazolidin-1-yl]-3-methyl-3-phenyl-butyrylamino}-thiazole-4-carboxylic acid methyl ester;

2-{(2S,3R)-2-[(R)-4-(2,3-Dihydro-benzo[1,4]dioxin-6-yl)-2,5-dioxo-imidazolidin-1-yl]-3-phenyl-butyrylamino}-thiazole-4-carboxylic acid methyl ester;

2-{(2S,3S)-2-[(R)-4-(4-Acetylamino-phenyl)-2,5-dioxo-imidazolidin-1-yl]-3-phenyl-butyrylamino}-thiazole-4-carboxylic acid methyl ester;

N-[4-(1-Hydroxy-1-methyl-ethyl)-thiazol-2-yl]-2-[(R)-4-(4-methoxy-phenyl)-2,5-dioxo-imidazolidin-1-yl]-3-phenyl-butyramide;

(2S,3S)-2-[(R)-4-(2,3-Dihydro-benzo[1,4]dioxin-6-yl)-2,5-dioxo-imidazolidin-1-yl]-N-[4-(1-hydroxy-propyl)-thiazol-2-yl]-3-phenyl-butyramide;

(2S,3S)-N-[4-(1-Hydroxy-ethyl)-thiazol-2-yl]-2-[(R)-4-(4-methoxy-phenyl)-2,5-dioxo-imidazolidin-1-yl]-3-phenyl-butyramide;

2-{(2S,3S)-2-[(R)-4-(4-Methoxy-phenyl)-2,5-dioxo-imidazolidin-1-yl]-3-phenyl-butyrylamino}-thiazole-4-carboxylic acid dimethylamide;

(2S,3S)-N-(4-Ethylsulfanyl-thiazol-2-yl)-2-{(R)-4-[4-(2-methoxy-ethoxy)-phenyl]-2,5-dioxo-imidazolidin-1-yl}-3-phenyl-butyramide;
(2S,3S)-N-(4-Ethanesulfinyl-thiazol-2-yl)-2-{(R)-4-[4-(2-methoxy-ethoxy)-phenyl]-2,5-dioxo-imidazolidin-1-yl}-3-phenyl-butyramide;
(2S,3S)-N-(4-Ethanesulfonyl-thiazol-2-yl)-2-{(R)-4-[4-(2-methoxy-ethoxy)-phenyl]-2,5-dioxo-imidazolidin-1-yl}-3-phenyl-butyramide;
(2S,3S)-N-[4-(2-Hydroxy-acetyl)-thiazol-2-yl]-2-{(R)-4-[4-(2-methoxy-ethoxy)-phenyl]-2,5-dioxo-imidazolidin-1-yl}-3-phenyl-butyramide;
(4-{(R)-1-[(1S,2S)-1-(4-Acetyl-thiazol-2-ylcarbamoyl)-2-phenyl-propyl]-2,5-dioxo-imidazolidin-4-yl}-phenoxy)-acetic acid methyl ester;
(4-{(R)-2,5-Dioxo-1-[(1S,2S)-2-phenyl-1-(4-propionyl-thiazol-2-ylcarbamoyl)-propyl]-imidazolidin-4-yl}-phenoxy)-acetic acid methyl ester;
(4-{2,5-Dioxo-1-[(1S,2S)-2-phenyl-1-(4-propionyl-thiazol-2-ylcarbamoyl)-propyl]-imidazolidin-4-yl}-phenoxy)-acetic acid;
(2S,3S)-N-(4-Acetyl-thiazol-2-yl)-2-[(R)-4-(4-dimethylcarbamoylmethoxy-phenyl)-2,5-dioxo-imidazolidin-1-yl]-3-phenyl-butyramide;
(2S,3S)-N-(4-Acetyl-thiazol-2-yl)-2-[(R)-4-(4-methylcarbamoylmethoxy-phenyl)-2,5-dioxo-imidazolidin-1-yl]-3-phenyl-butyramide;
(2S,3S)-N-(4-Acetyl-thiazol-2-yl)-2-[(R)-4-(4-carbamoylmethoxy-phenyl)-2,5-dioxo-imidazolidin-1-yl]-3-phenyl-butyramide;
(2S,3S)-N-(4-Acetyl-thiazol-2-yl)-2-((R)-4-{4-[(2-methoxy-ethylcarbamoyl)-methoxy]-phenyl}-2,5-dioxo-imidazolidin-1-yl)-3-phenyl-butyramide;
(2S,3S)-N-(4-Acetyl-thiazol-2-yl)-2-((R)-4-{4-[(2-methoxy-ethylcarbamoyl)-methoxy]-phenyl}-2,5-dioxo-imidazolidin-1-yl)-3-phenyl-butyramide;
(2S,3S)-N-(4-Acetyl-thiazol-2-yl)-2-{(R)-4-[4-(2-morpholin-4-yl-2-oxo-ethoxy)-phenyl]-2,5-dioxo-imidazolidin-1-yl}-3-phenyl-butyramide;
(2S,3S)-N-(4-Acetyl-thiazol-2-yl)-2-{(R)-2,5-dioxo-4-[4-(2-oxo-2-pyrrolidin-1-yl-ethoxy)-phenyl]-imidazolidin-1-yl}-3-phenyl-butyramide;
(2S,3S)-2-[(R)-4-(4-Dimethylcarbamoylmethoxy-phenyl)-2,5-dioxo-imidazolidin-1-yl]-3-phenyl-N-(4-propionyl-thiazol-2-yl)-butyramide;
(2S,3S)-2-[(R)-4-(4-Methylcarbamoylmethoxy-phenyl)-2,5-dioxo-imidazolidin-1-yl]-3-phenyl-N-(4-propionyl-thiazol-2-yl)-butyramide;
(2S,3S)-2-((R)-4-{4-[(2-Methoxy-ethylcarbamoyl)-methoxy]-phenyl}-2,5-dioxo-imidazolidin-1-yl)-3-phenyl-N-(4-propionyl-thiazol-2-yl)-butyramide;
(2S,3S)-2-{(R)-4-[4-(2-Morpholin-4-yl-2-oxo-ethoxy)-phenyl]-2,5-dioxo-imidazolidin-1-yl}-3-phenyl-N-(4-propionyl-thiazol-2-yl)-butyramide;
(2S,3S)-2-{(R)-2,5-Dioxo-4-[4-(2-oxo-2-pyrrolidin-1-yl-ethoxy)-phenyl]-imidazolidin-1-yl}-3-phenyl-N-(4-propionyl-thiazol-2-yl)-butyramide;
(2S,3S)-2-{(R)-4-[4-(2-Azetidin-1-yl-2-oxo-ethoxy)-phenyl]-2,5-dioxo-imidazolidin-1-yl}-3-phenyl-N-(4-propionyl-thiazol-2-yl)-butyramide and
(2S,3S)-N-(4-Cyclopropanecarbonyl-thiazol-2-yl)-2-[(R)-4-(4-methylcarbamoylmethoxy-phenyl)-2,5-dioxo-imidazolidin-1-yl]-3-phenyl-butyramide.

"Alkyl" denotes a straight-chained, branched or cyclic saturated aliphatic hydrocarbon. Preferably, alkyl denotes a lower alkyl group i.e., a C1-C6 alkyl group and includes methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl. Examples of cycloalkyl groups are moieties having 3 to 10, preferably 3 to 7 carbon atoms including cyclopropyl, cyclopentyl and cyclohexyl groups.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Hetero atom" means an atom selected from N, O and S.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

As mono-, di- or tri-substituents on the aryl or heteroaryl rings one can include hydroxyl, alkoxy, hydroxy alkoxy, halogen, alkylamines, aniline derivatives, amide derivatives of the aniline derivatives, carboxylic acids, carboxylic acid esters, carboxylic acid amides and methanesulfonyl. When two or more substituents are present on an aryl or heteroaryl ring they may also be present in the form of a fused ring. Such fused rings include, but are not limited to, 3,4-methylenedioxyphenyl and 3,4-ethylenedioxyphenyl.

"Alkoxy or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like. Also included within the meaning of alkoxy are alkoxy side chains bearing additional substituents such as carboxylic acids, carboxylic acid esters and carboxylic acid amides.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard Hans ed. (Elsevier, 1985). See also, Ansel et. al., Pharmaceutical Dosage Forms and Drug Delivery Systems (6th Ed. 1995) at pp. 108-109; Krogsgaard-Larsen, et al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted aryl or heteroaryl, means that the substitution can occur at one or more positions and, unless otherwise indicated, that the substituents at each substitution site are independently selected from the specified options.

"Therapeutically effective amount" means an amount of at least one designated compound that significantly inhibits proliferation and/or prevents differentiation of a human tumor cell, including human tumor cell lines.

The compounds of the present invention are useful in the treatment or control of cell proliferative disorders such as inflammatory/autoimmune disorders, e.g., restenosis, cognative disorders e.g., dementia and Alzeheimer's disease. CNS disorders, e.g., neuropathic pain and, in particular, oncological disorders. These compounds and formulations containing said compounds may be useful in the treatment or control of solid tumors, such as, for example, breast, colon, lung and prostate tumors.

The compounds of formula I as well as their salts have at least one asymmetric carbon atom and therefore may be present as mixtures of different stereoisomers. The various isomers can be isolated by known separation methods, e.g., chromatography.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Reaction Schemes

Compounds of formula 6, where R8=alkyl or substituted alkyl, can be prepared according to the method outlined in scheme 1. As set forth in scheme 1, the known compound 1 when treated with di-tert-butyl dicarbonate in refluxing pyridine gave compound 2. Compound 2 was then hydrolyzed with lithium hydroxide in a mixture of tetrahydrofuran and water to give the corresponding carboxylic acid 3. Compound 3 was first reacted with 2-chloro-4,5-dimethoxy-1,3,5-triazine and N-methylmorpholine in tetrahydrofuran, then with the N,O-dimethylhydroxylamine hydrochloride and triethylamine to give the compound with formula 4. Compound 4 can be converted to ketones of formula 5 using alkyl magnesium chloride or bromide salts (Grignard reagents) in ethereal solvents. Compounds of formula 6 are then obtained after treatment of compounds of formula 5 with acid to effect removal of the tert-butyloxycarbonyl group e.g trifluoroacetic acid.

Scheme 1

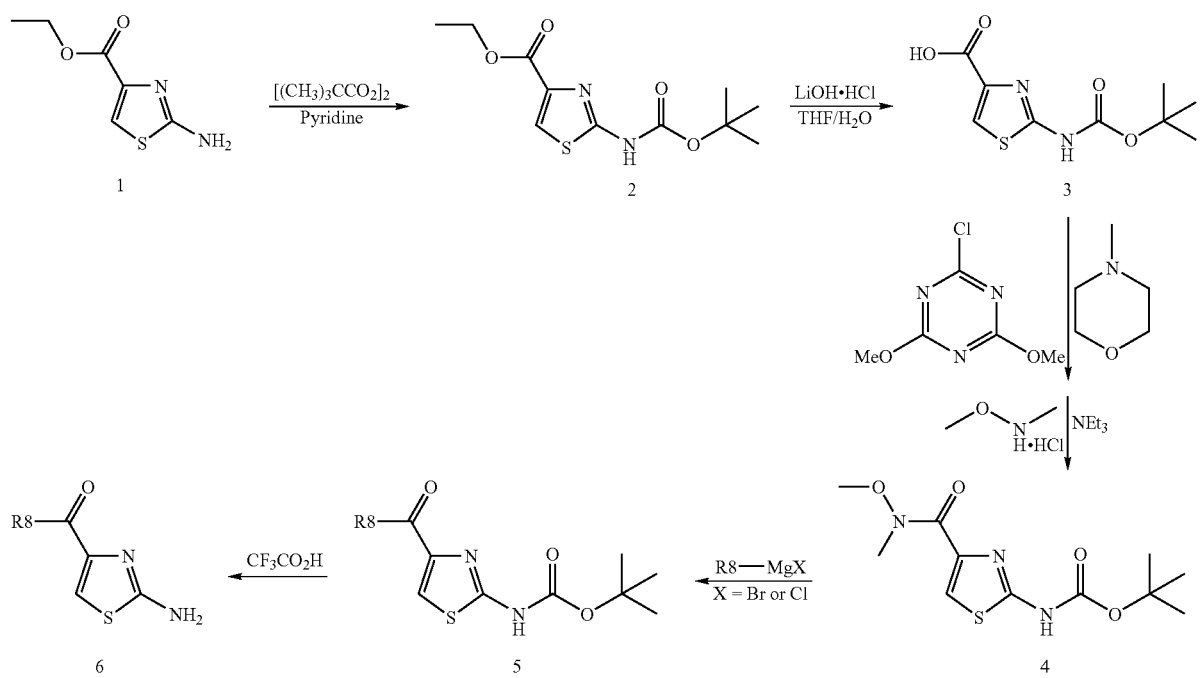

As set forth in scheme 2, an alternative method of functionalizing compound 4 is via formation of the bis-tert-butoxycarbonylamino derivative 7 with di-tert-butyl dicarbonate and potassium carbonate. Compound 7 can then be converted into ketones of formula 8 by reaction with the appropriate organometallic reagent e.g. organolithium reagents. Compounds of formula 6 are obtained from compounds of formula 8 after treatment with acid to effect removal of the tert-butyloxycarbonyl group e.g. trifluoroacetic acid.

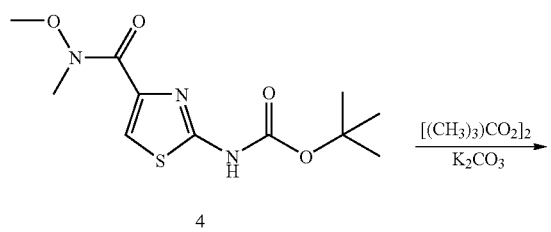

Scheme 2

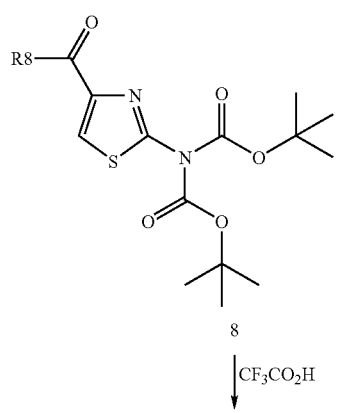

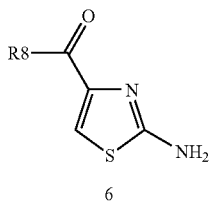

6

In the case where the substituent R8 contains a reactive functional group further modification of this substituent may be possible by appropriate use of known methods and chemical transformations by one knowledgable in the field. Such modifications may be possible immediately after introduction of the R8 substituent or on any subsequent derivative bearing this substituent.

In addition, the ketone functional group present in compounds of formula 5, 6 and 8 is a reactive functional group and may be amenable to further chemical transformations using methods known in the field of organic chemistry and by one knowledgable in the field. Such modifications may be possible immediately after formation of the ketone functional group or on any subsequent derivative bearing this substituent.

As set forth in scheme 3, a solution of substituted 2-propenoic acid 9 and triethylamine in dry tetrahydrofuran at low temperature, e.g. −78° C., is treated with trimethylacetyl chloride and then with the anion of (S)-(+)-4-phenyl-2-oxazolidinone anion (generated with n-butyl lithium) to give a compounds of formula 10. Compounds of formula 10 react with an appropriate Grignard reagents in the presence of copper(I) bromide-dimethyl sulfide complex to give compounds of formula 11. The Grignard reagents utilized in this transformation may contain aryl, substituted aryl, heteroaryl or substituted heteroaryl groups which are incorporated in to compounds of formula 11. Compounds of formula 11 were converted to compounds of formula 12 by treatment first with a strong base e.g. potassium hexamethyldisilazane followed by treatment with 2,4,6 triisopropylphenylsulfonyl azide. Compounds of formula 12 were hydrogenolyzed in the presence of di-tert-butyl dicarbonate and palladium on charcoal to give compounds of formula 13. Compounds of formula 14 were obtained from compounds of formula 13 by treatment with hydrogen peroxide and lithium hydroxide.

Scheme 3

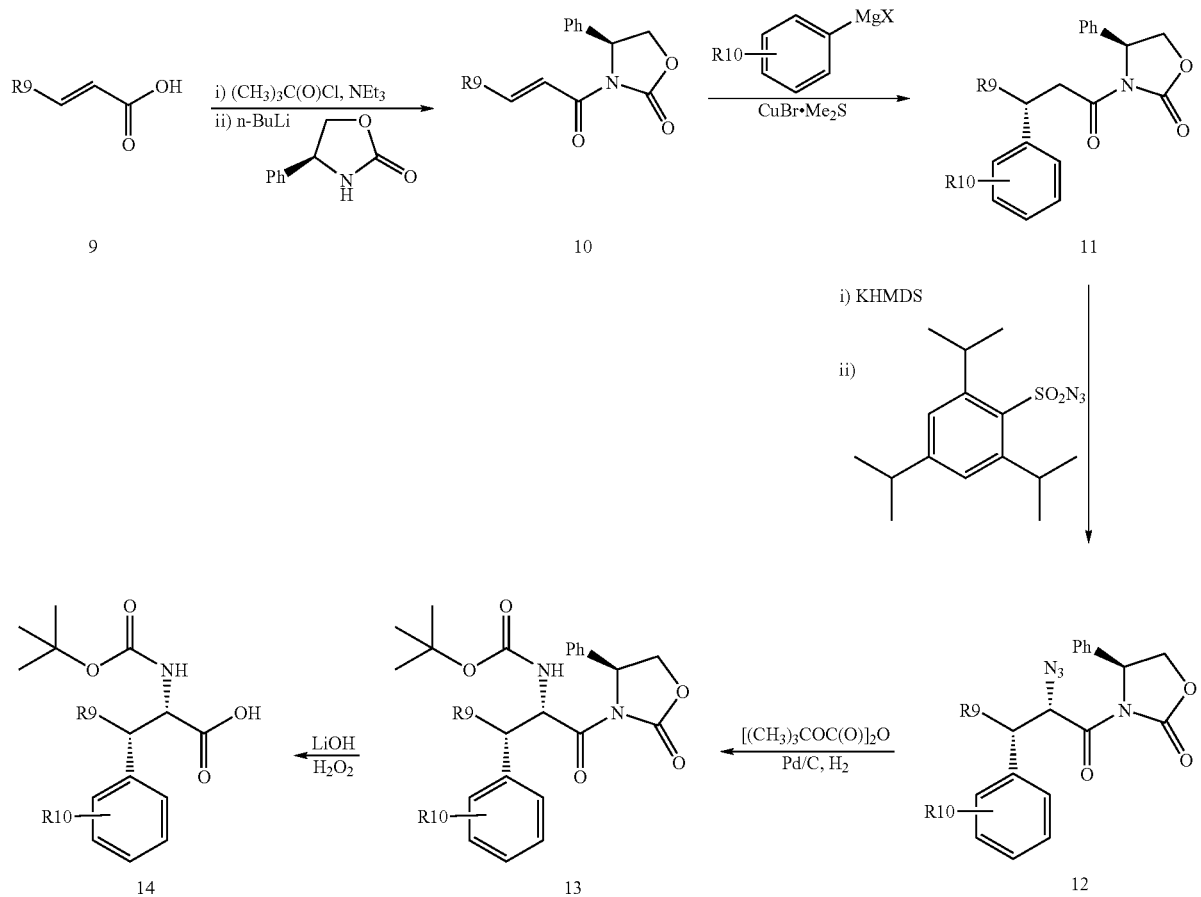

The R9 group shown in scheme 3 can be either alkyl or substituted alkyl. In the case where R9 is substituted alkyl, the substituent may be unreactive to the conditions employed in subsequent chemical transformations on remote parts of the molecule so that the R9 group persists into the compounds claimed in the present invention in a chemically unchanged form. Alternatively, the R9 group may contain a potentially reactive functional group present in a protected form from which the functional group may be liberated at an appropriate point during subsequent chemical transformations. For a more complete description of the utility of protecting groups see Protecting Groups in Organic Synthesis, 3$^{rd}$ Edition, T. W. Greene and P. G. M. Wuts, Wiley-Interscience.

The R10 group shown in scheme 3 can be either hydrogen, alkyl, substituted alkyl or halogen.

As set forth in scheme 4, compounds of formula 14 were converted to the acyl fluorides of formula 15 using cyanuric fluoride in the presence of pyridine in dichloromethane. Compounds of formula 15 were treated with compounds of formula 6 in the presence of N-methyl morpholine and the reaction catalyzed by the addition of 4-dimethylaminopyridine and microwave irradiation to give an internal reaction temperature between 100 and 120° C. Compounds of formula 6 may be known compounds, e.g. R8=OMe, or compounds prepared according to known methods, or compounds prepared according to the methods outlined in schemes 1 and 2. In this way, compounds of formula 16 were obtained. Compounds of formula 16 were deprotected with trifluoroacetic acid to give a compounds of formula 17. Compounds of formula 17 were coupled with α-amino acid derivatives, preferably an enantiomerically enriched phenyl glycine derivative (either a known compound or a compound prepared by known methods), with 1-hydroxybenzotriazole and O-benzotriazol-1-yl-N,N,N',N'-tetramethyluronium-hexaflurorophosphate to give compounds of formula 18. In the case when the α-amino acid derivative used is a phenyl glycine derivative R11 may be hydroxy, alkoxy, substituted alkoxy, acylated amine, substituted sulfone and phosphate. In the case when the α-amino acid derivatives is an enantiomerically enriched phenyl glycine derivative these compounds may be conveniently prepared from 4-hydroxyphenyl glycine for which both enantiomers are commercially available. Compounds of formula 18 were reacted with trifluoroacetic acid to give compounds of formula 19 by removal of the tert-butylcarbamate protecting group. Compounds of formula 19 were treated with diphosgene and diisopropylethyl amine to give substituted hydantoins of formula 20 in a solvent such as dichloromethane, tetrahydrofuran or a mixture of tetrahdrofuran and toluene.

Scheme 4
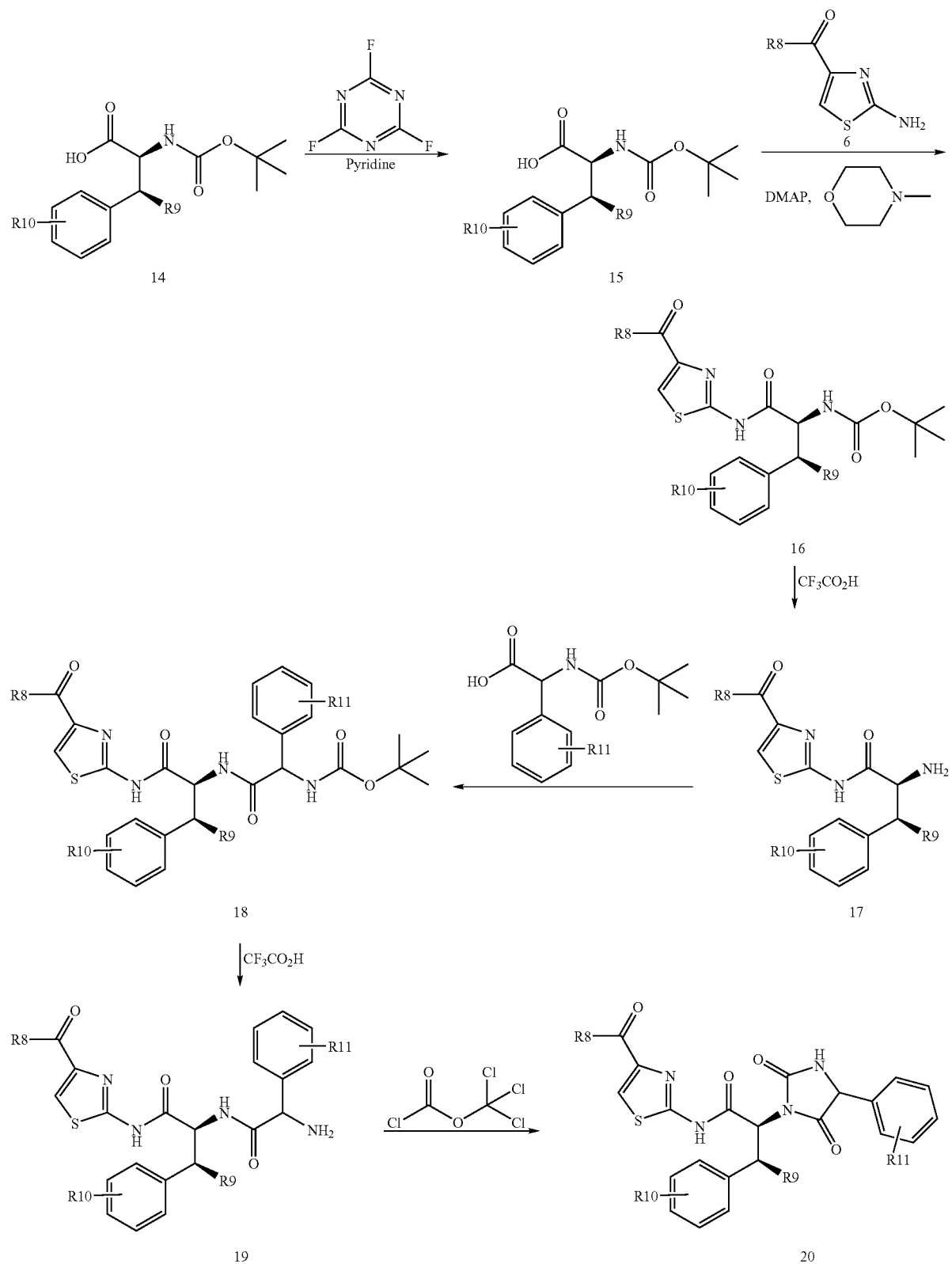

EXAMPLE 1

(2S,3S)-N-(4-Acetyl-thiazol-2-yl)-2-[(R)-4-(4-methoxy-phenyl)-2,5-dioxo-imidazolidin-1-yl]-3-phenyl-butyramide

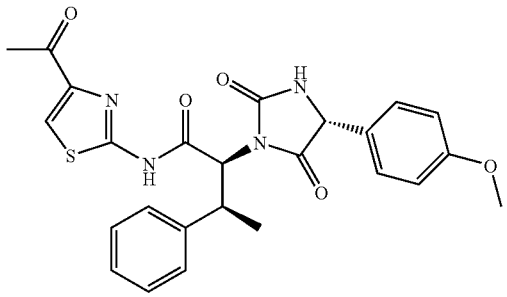

(1) 1-(2-Amino-thiazol-4-yl)-ethanone was prepared using the 3 step procedure outlined in steps (1a) to (1c) and then converted into (2S,3S)-N-(4-acetyl-thiazol-2-yl)-2-[(R)-4-(4-methoxy-phenyl)-2,5-dioxo-imidazolidin-1-yl]-3-phenyl-butyramide according to the procedures outlined in steps (2) to (7).

(1a) Sulfuryl chloride (97% purity) (18.7 mL, 226 mmol) was added dropwise over 1 hour to a stirred solution of 2,3-butanedione (97% purity) (20 g, 225 mmol) in benzene (80 mL) at 60° C. and the mixture left to stir at this temperature overnight. The benzene was removed in vacuo and the residue was purified by distillation to give 1-chloro-2,3-butanedione as a yellow liquid, b.p.=95 to 105° C. (≈10 mmHg), (16.2 g, 60%).

(1b) To a stirred mixture of thiourea (8.87 g, 115 mmol) in ethanol (20.9 mL) was added 1-chloro-2,3-butanedione (13.90 g, 115 mmol) dropwise, a slight exothermic reaction resulted. The mixture was stirred at ambient temperature for 1 hour. The reaction mixture was filtered and the precipitate washed with ethyl ether (2x). The tan solid was air dried then dried under high vacuum overnight to give 1-(2-amino-thiazol-4-yl)-ethanone hydrochloride as a tan solid (21.5 g, 97%).

(1c) 1-(2-Amino-thiazol-4-yl)-ethanone hydrochloride (5.6 g 29.1 mmol) was dissolved in water (15 mL) and cooled in an ice bath. To this was added dropwise 17 N ammonium hydroxide (15 mL, 105 mmol). The resulting mixture was stirred for 15 minutes than filtered and washed with cold water (3x), cold methanol (3x50 mL), ethyl ether (3x10 mL). The precipitate was dried first by passing air through the material and then in vacuo to give 1-(2-amino-thiazol-4-yl)-ethanone as a pale yellow solid (2.6 g, 57%).

(2S,3S)-2-tert-Butoxycarbonylamino-3-phenyl-butyric acid (1.94 g, 6.93 mmol) and pyridine (0.63 mL, 7.74 mmol) were dissolved in dichloromethane (50 mL) at −10° C. Cyanuric fluoride (1.80 mL, 21.1 mmol) was added dropwise. The mixture was stirred for 1 hour and ice-water was added. The mixture was extracted with dichloromethane (2x). The organic extracts were washed with water, brine and dried (sodium sulfate). Evaporation of the solvents gave crude ((1S,2S)-1-fluorocarbonyl-2-phenyl-propyl)-carbamic acid tert-butyl ester (2.2 g) as a cloudy oil which was used in the next step.

Crude ((1S,2S)-1-fluorocarbonyl-2-phenyl-propyl)-carbamic acid tert-butyl ester (2.2 g, ≈6.93 mol), 1-(2-amino-thiazol-4-yl)-ethanone (1.0 g, 7.0 mmol), 4-methyl morpholine (1.56 mL, 14 mmol) and N,N-dimethylaminopyridine (10 mg, 0.082 mmol) were dissolved in tetrahydrofuran (20 mL). The mixture was microwaved at 120° C. for 15 minutes. The solution was diluted with ethyl acetate and washed with 1.5 M aqueous potassium hydrogen sulfate, water and brine. After drying (sodium sulfate), filtration and evaporation of the solvents, [(1S,2S)-1-(4-acetyl-thiazol-2-ylcarbamoyl)-2-phenyl-propyl]-carbamic acid tert-butyl ester (2.8 g, 89%) was obtained as a yellow foam.

[(1S,2S)-1-(4-Acetyl-thiazol-2-ylcarbamoyl)-2-phenyl-propyl]-carbamic acid tert-butyl ester (2.8 g, 6.25 mmol) was dissolved in dichloromethane (42 mL) in an ice bath. Trifluoroacetic acid (35 mL) was added. After 30 minutes, the reaction mixture was evaporated and the residue was precipitated with hexanes/ether. The mixture was stirred vigorously for 10 minutes and then filtered. The solid was partitioned between aqueous sodium bicarbonate and dichloromethane. The organic layer was separated and the aqueous layer was extracted with dichloromethane. The combined organic extracts were washed with brine and dried (sodium sulfate). Evaporation of the solvents gave (2S,3S)-N-(4-acetyl-thiazol-2-yl)-2-amino-3-phenyl-butyramide (1.9 g, 95%) as a white solid.

(5) (2S,3S)-N-(4-Acetyl-thiazol-2-yl)-2-amino-3-phenyl-butyramide (1.8 g, 5.64 mmol), (R)-tert-butyloxycarbonylamino-4-methyoxyphenylglycine (prepared according to the procedure of Hyun, M. H., et al. *J. Liq. Chrom. & Rel. Technol.* 2002, 25, 573-588.) (1.67 g, 5.9 mmol), O-benzotriazol-1-yl-N,N,N',N'-tetramethyluronium hexaflurorophosphate (2.35 g, 6.2 mmol) and diisopropylethyl amine were dissolved in dimethylformamide (20 mL) in an ice bath. 1-Hydroxybenzotriazole (0.84 g, 6.2 mmol) in dimethylformamide (5 mL) was added dropwise. Stirring was continued for 30 minutes at 0° C. The reaction mixture was diluted with ethyl acetate and the mixture washed with water and brine. The organic layer was diluted with an equal volume of dichloromethane, filtered through a pad of silica gel with a layer of sodium sulfate on the top and then eluted with 1:1 ethyl acetate/dichloromethane. Evaporation of the solvents gave a white solid which was triturated with ether/hexane to give [(R)-[(1S,2S)-1-(4-acetyl-thiazol-2-ylcarbamoyl)-2-phenyl-propylcarbamoyl]-(4-methoxy-phenyl)-methyl]-carbamic acid tert-butyl ester (3.1 g, 97%).

(6) [(R)-[(1S,2S)-1-(4-Acetyl-thiazol-2-ylcarbamoyl)-2-phenyl-propylcarbamoyl]-(4-methoxy-phenyl)-methyl]-carbamic acid tert-butyl ester (3.1 g, 5.2 mmol) was stirred in dichloromethane (50 mL) in an ice-bath. Trifluoroacetic acid (50 mL) was added and the solution was stirred for 1 hour. The reaction mixture was evaporated and the residue was precipitated with hexanes/ether. The mixture was stirred vigorously for 10 minutes and then filtered. The solid was partitioned between aqueous sodium bicarbonate and dichloromethane. The organic layer was separated and the aqueous layer extracted with dichloromethane. The combined organic extracts were washed with brine and dried (sodium sulfate). Evaporation of the solvents gave (2S,3S)-N-(4-acetyl-thiazol-2-yl)-2-[(R)-2-amino-2-(4-methoxy-phenyl)-acetylamino]-3-phenyl-butyramide (2.7 g, 90% pure) as a white solid.

(7) (2S,3S)-N-(4-Acetyl-thiazol-2-yl)-2-[(R)-2-amino-2-(4-methoxy-phenyl)-acetylamino]-3-phenyl-butyramide (2.7 g, 90% purity, 5.2 mmol) and diisopropylethylamine (4.2 mL, 23.6 mmol) in tetrahydrofuran (50 mL) were added to a solution of diphosgene (0.48 mL, 4 mmol) in a mixture of toluene (50 mL) and tetrahydrofuran (50 mL) over 10 minutes at 0° C. The mixture was stirred at 0° C. for 20 minutes and diluted with ethyl acetate. The mixture was washed with water, brine and dried (sodium sulfate). Evaporation of the solvents and chromatography of the residue over silica gel with 0.4-1% v/v methanol in dichloromethane gave (2S,3S)-N-(4-acetyl-thiazol-2-yl)-2-[(R)-4-(4-methoxy-phenyl)-2,5-dioxo-imidazolidin-1-yl]-3-phenyl-butyramide (2.36 g, 92%) as a white solid.

HRMS: Obs. Mass, 493.1538. Calcd. Mass, 493.1540 (M+H).

EXAMPLE 2

In a manner similar to that described in Example 1, the following compounds were prepared.

a) (2S,3S)-N-(4-Acetyl-thiazol-2-yl)-2-[(R)-4-(4-hydroxy-phenyl)-2,5-dioxo-imidazolidin-1-yl]-3-phenyl-butyramide.

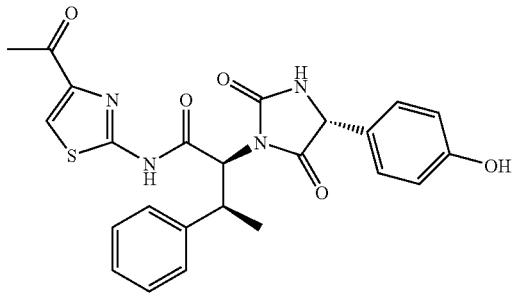

HRMS: Obs. Mass, 479.1385. Calcd. Mass, 479.1384 (M+H).

b) (2S,3S)-N-(4-Acetyl-thiazol-2-yl)-2-{(R)-4-[4-(2-hydroxy-ethoxy)-phenyl]-2,5-dioxo-imidazolidin-1-yl}-3-phenyl-butyramide.

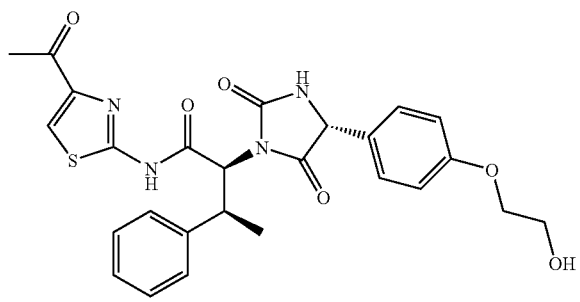

(R)-tert-Butoxycarbonylamino-{4-[2-(tetrahydro-pyran-2-yloxy)-ethoxy]-phenyl}-acetic acid, which was used in place of (R)-tert-butyloxycarbonylamino-4-methyoxyphenylglycine in Example 1d, was prepared as follows. (R)-tert-butoxycarbonyl-(4-hydroxy-phenyl)-acetic acid (2.67 g, 10 mmol) (Salituro, G. M.; Townsend, C. A. J. Am. Chem. Soc. 1990, 112, 760-770.) was dissolved in dimethylformamide (70 mL) in an ice bath. Sodium hydride (0.88 g, 60% in mineral oil, 22 mmol) was added in small portions. The mixture was warmed up to 10° C. for 1 hour. 2-(2-Bromo-ethoxy)-tetrahydropyran (1.7 mol, 11 mmol) in dimethylformamide (20 mL) was added drop wise. The reaction mixture was stirred for 24 hours and then diluted with ice-water. The mixture was extracted with ethyl acetate. The aqueous layer was cooled in an ice bath and acidified using 1.5 M aqueous potassium hydrogen sulfate to pH=2-3. The resulting mixture was extracted with ethyl acetate (5×), washed with water (5×), brine and dried (sodium sulfate). Evaporation of the solvents gave (R)-tert-butoxycarbonylamino-{4-[2-(tetrahydropyran-2-yloxy)-ethoxy]-phenyl}-acetic acid as a solid white foam (3.2 g, 82%).

HRMS: Obs. Mass, 523.1645. Calcd. Mass, 523.1646 (M+H).

c) (2S,3S)-N-(4-Acetyl-thiazol-2-yl)-2-{(R)-4-[4-(2-methoxy-ethoxy)-phenyl]-2,5-dioxo-imidazolidin-1-yl}-3-phenyl-butyramide.

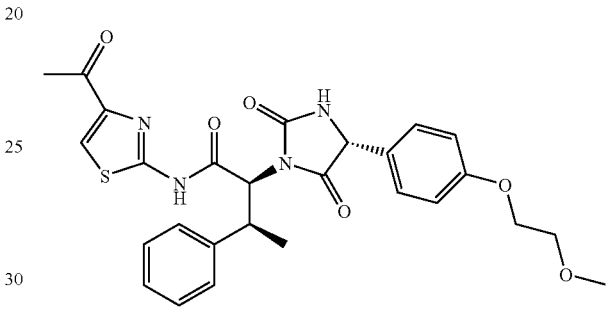

(R)-tert-Butoxycarbonylamino-[4-(2-methoxy-ethoxy)-phenyl]-acetic acid, which was used in place of (R)-tert-butyloxycarbonylamino-4-methyoxyphenylglycine in Example 1d, was prepared in a similar manner as described for the synthesis of (R)-tert-butoxycarbonylamino-{4-[2-(tetrahydro-pyran-2-yloxy)-ethoxy]-phenyl}-acetic acid in Example 2b.

HRMS: Obs. Mass, 537.1803. Calcd. Mass, 537.1803 (M+H).

d) (2S,3S)-N-(4-Acetyl-thiazol-2-yl)-2-((R)-4-{4-[2-(2-methoxy-ethoxy)-ethoxy]-phenyl}-2,5-dioxo-imidazolidin-1-yl)-3-phenyl-butyramide.

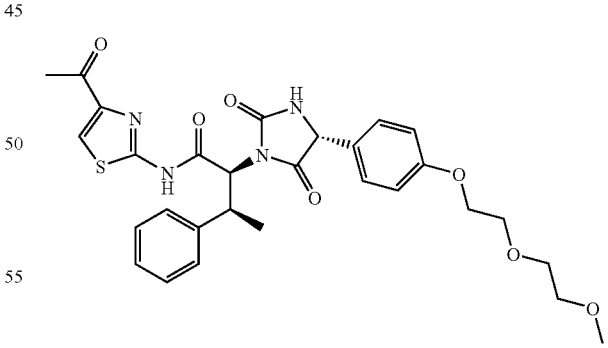

(R)-tert-Butoxycarbonylamino-{4-[2-(2-methoxy-ethoxy)-ethoxy]-phenyl}-acetic acid, which was used in place of (R)-tert-butyloxycarbonylamino-4-methyoxyphenylglycine in Example 1d, was prepared in a similar manner as described for the synthesis of (R)-tert-butoxycarbonylamino-{4-[2-(tetrahydro-pyran-2-yloxy)-ethoxy]-phenyl}-acetic acid in Example 2b.

HRMS: Obs. Mass, 581.2067. Calcd. Mass, 581.2065 (M+H).

e) (2S,3S)-N-(4-Acetyl-thiazol-2-yl)-2-{(R)-4-[4-(2-ethoxy-ethoxy)-phenyl]-2,5-dioxo-imidazolidin-1-yl}-3-phenyl-butyramide.

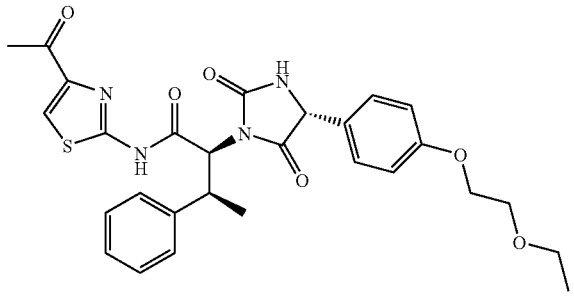

(R)-tert-Butoxycarbonylamino-[4-(2-ethoxy-ethoxy)-phenyl]-acetic acid, which was used in place of (R)-tert-butyloxycarbonylamino-4-methyoxyphenylglycine in Example 1d, was prepared in a similar manner as described for the synthesis of (R)-tert-butoxycarbonylamino-{4-[2-(tetrahydro-pyran-2-yloxy)-ethoxy]-phenyl}-acetic acid in Example 2b.

HRMS: Obs. Mass, 551.1963. Calcd. Mass, 551.1959 (M+H).

f) (2S,3S)-N-(4-Acetyl-thiazol-2-yl)-2-{(R)-4-[4-(2-dimethylamino-ethoxy)-phenyl]-2,5-dioxo-imidazolidin-1-yl}-3-phenyl-butyramide, trifluoro-acetic acid salt.

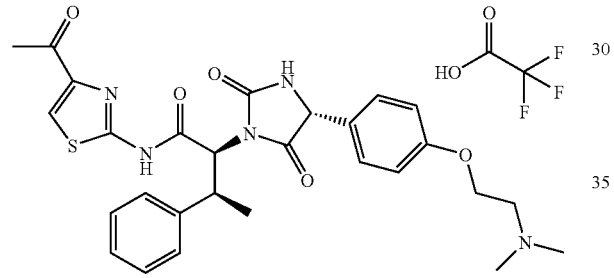

(R)-tert-Butoxycarbonylamino-[4-(2-dimethylamino-ethoxy)-phenyl]-acetic acid, which was used in place of (R)-tert-butyloxycarbonylamino-4-methyoxyphenylglycine in Example 1d, was prepared in a similar manner as described for the synthesis of (R)-tert-butoxycarbonylamino-[4-(2-diethylamino-ethoxy)-phenyl]-acetic acid in Example 2g.

HRMS: Obs. Mass, 550.2117, Calcd. Mass, 550.2119 (M+H)

g) (2S,3S)-N-(4-Acetyl-thiazol-2-yl)-2-{(R)-4-[4-(2-diethylamino-ethoxy)-phenyl]-2,5-dioxo-imidazolidin-1-yl}-3-phenyl-butyramide, trifluoro-acetic acid salt.

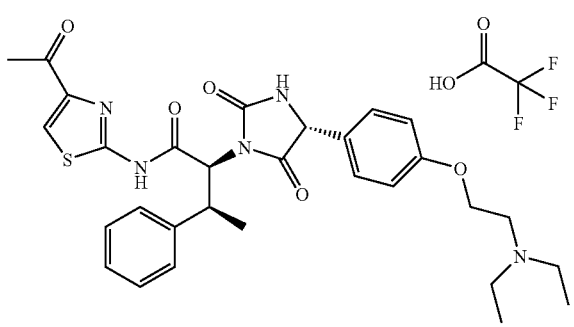

(R)-tert-Butoxycarbonylamino-[4-(2-diethylamino-ethoxy)-phenyl]-acetic acid, which was used in place of (R)-tert-butyloxycarbonylamino-4-methyoxyphenylglycine in Example 1d, was prepared as follows:

To a suspension of sodium hydride (43.8 mg, 95% Aldrich) in anhydrous N,N-dimethylformamide (4 mL), was added dropwise a solution of (R)-tert-butoxycarbonylamino-(4-hydroxyphenyl)-acetic acid (200.0 mg, 0.749 mmol) at 0° C. After addition, the reaction mixture was allowed to stir at ambient temperature for 20 minutes. A cooled solution of 2-bromoethyl-N,N-diethylamine hydrochloride (234 mg, 0.91 mmol) in N,N-dimethylformamide (2 mL), was treated with sodium hydride (23 mg, 1.00 mmol), and was then added slowly to the above suspension at 0° C. The reaction was allowed to stir at ambient temperature for 17 hours before it was quenched and neutralized by pouring into 1N aqueous hydrochloric acid. The resulting mixture was lyophlized dry to give the product (contaminated with inorganic salts) which was used without further purification (61.9.5 mg).

HRMS: Obs. Mass, 578.2430, Calcd. Mass, 578.2432 (M+H).

h) (2S,3S)-N-(4-Acetyl-thiazol-2-yl)-2-[(R)-4-(4-ethoxy-phenyl)-2,5-dioxo-imidazolidin-1-yl]-3-phenyl-butyramide

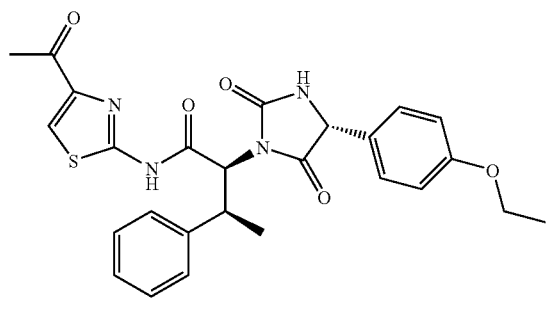

(R)-tert-Butoxycarbonylamino-(4-ethoxyphenyl)-acetic acid, which was used in place of (R)-tert-butyloxycarbonylamino-(4-methoxyphenylglycine) in Example 1d, was prepared in a manner similar to that described for the synthesis of (R)-tert-butoxycarbonylamino-{4-[2-(tetrahydro-pyran-2-yloxy)-ethoxy]-phenyl}-acetic acid in Example 2b).

HRMS: Obs. Mass, 507.1696. Calcd. Mass, 507.1697 (M+H).

i) (2S,3S)-N-(4-Acetyl-thiazol-2-yl)-2-{(S)-4-[4-(2-dimethylamino-ethoxy)-phenyl]-2,5-dioxo-imidazolidin-1-yl}-3-phenyl-butyramide, trifluoro-acetic acid salt.

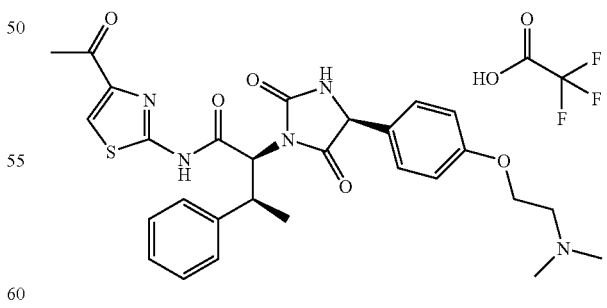

(2S,3S)-N-(4-Acetyl-thiazol-2-yl)-2-{(S)-4-[4-(2-dimethylamino-ethoxy)-phenyl]-2,5-dioxo-imidazolidin-1-yl}-3-phenyl-butyramide was isolated as the minor isomer following the last step in the preparation described in Example 2f.

HRMS: Obs. Mass, 550.2118, Calcd. Mass, 550.2119 (M+H).

j) (4-{1-[(1S,2S)-1-(4-Acetyl-thiazol-2-ylcarbamoyl)-2-phenyl-propyl]-2,5-dioxo-imidazolidin-4-yl}-phenyl)-phosphonic acid diethyl ester.

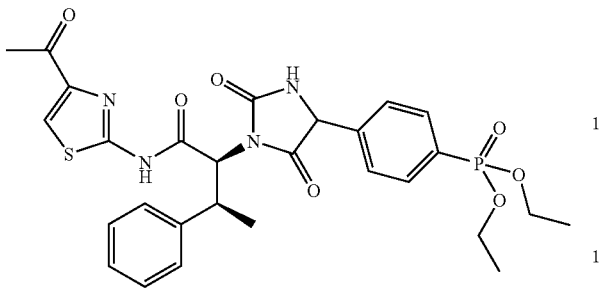

(±)-tert-Butoxycarbonylamino-{4-phenyl phosphonic acid diethyl ester}-acetic acid, which was used in place of (R)-N-(tert-butyloxycarbonyl-(4-methoxyphenylglycine) in Example 1d, was prepared as follows.

(1) To a cold solution of (R)-tert-butoxycarbonylamino-(4-hydroxyphenyl)-acetic acid benzyl ester (prepared as described in *J. Med. Chem.* 1991, 34, 956-968) (2.0 g, 5.60 mmol) in dry methylene chloride (60 mL) was added N-phenylbis(trifluoromethanesulphonamide) (4.03 g, 11.28 mmol) and diisopropylethylamine (1.0 mL, 5.74 mmol). The reaction mixture was stirred at room temperature for 48 hours. The solvent was removed in vacuo and the residue was dissolved in ethyl acetate, washed with 10% aqueous potassium carbonate (2×), water and brine and dried over sodium sulfate. The solvent was removed in vacuo, and the product was purified by chromatography over silica gel eluted first with 50% methylene chloride in hexanes and then with 30% ethyl acetate in hexanes to afford tert-butoxycarbonylamino-(4-trifluoromethane-sulfonyloxy-phenyl)-acetic acid benzyl ester (2.62 g, 96%).

To a solution of tert-butoxycarbonylamino-(4-trifluoromethane-sulfonyloxy-phenyl)-acetic acid benzyl ester (2.2 g, 4.50 mmol) in acetonitrile (10 mL) was added diethylphosphite (643 µL, 5.00 mmol) followed by N-methylmorpholine (691 µL, 6.30 mmol). The mixture was purged with nitrogen and tetrakis-triphenylphosphine palladium (260 mg, 0.23 mmol, 15 mol %) was added. The reaction mixture was heated to 75° C. overnight then cooled to room temperature and diluted with ethyl acetate (50 mL). The mixture was poured into a separatory funnel containing ethyl acetate (100 mL) and washed with 0.2M aqueous hydrochloric acid (2×), water (2×), brine and dried over sodium sulfate. The solvent was removed in vacuo, and the product was chromatographed over silica gel gradient eluted between 10 to 75% ethyl acetate in hexanes to afforded tert-butoxycarbonylamino-[4-(diethoxy-phosphoryl)-phenyl]-acetic acid benzyl ester (2.0 g, 93%).

To solution of tert-butoxycarbonylamino-[4-(diethoxy-phosphoryl)-phenyl]-acetic acid benzyl ester (2.0 g, 4.2 mmol) in ethanol (20 mL) was added 10% palladium on activated carbon (200 mg). The mixture was stirred under an atmosphere of hydrogen at atmospheric pressure for two days. The reaction mixture was filtered through a pad of Celite®. The solids were washed with ethanol and the combined ethanolic filtrate was concentrated in vacuo to afford (±)-tert-butoxycarbonylamino-{4-phenyl phosphonic acid diethyl ester}-acetic acid (1.5 g; 92%). HRMS: Obs. Mass, 388.1516. Calcd. Mass, 388.1520 (M+H).

HRMS: Obs. Mass, 599.1722. Calcd. Mass, 599.1724 (M+H).

k) (2S,3S)-N-(4-Acetyl-thiazol-2-yl)-2-[4-(4-dimethylamino-phenyl)-2,5-dioxo-imidazolidin-1-yl]-3-phenyl-butyramide.

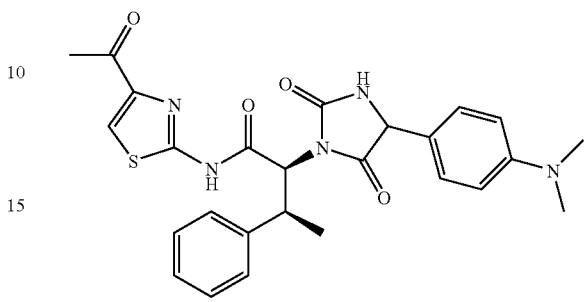

Prepared as described in Example 1 except that tert-butoxycarbonylamino-(4-dimethylamino-phenyl)-acetic acid was used in place of (R)-tert-butyloxycarbonylamino-4-methyoxyphenylglycine.

HRMS: HRMS: Obs. Mass, 506.1858. Calcd. Mass, 506.1857 (M+H)

EXAMPLE 3

(2S,3S)-N-(4-Acetyl-thiazol-2-yl)-2-[(R)-4-(4-methoxy-phenyl)-2,5-dioxo-imidazolidin-1-yl]-3-phenyl-pentanoic acid (4-acetyl-thiazol-2-yl)-amide

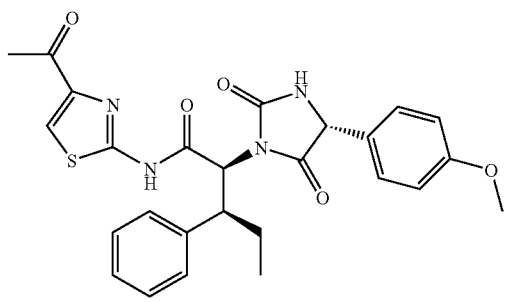

(1) To a solution of 2-pentenoic acid (5.44 g, 54 mmol) and triethylamine (6 g, 60 mmol) in anhydrous tetrahydrofuran (120 mL) under nitrogen at −78° C. was added trimethylacetyl chloride (7.36 mL, 60 mmol). The reaction mixture was stirred at −78° C. for 10 minutes, 0° C. for 1 hour, then re-cooled to −78° C. At the same time, in a seperate flask charged with a solution of (S)-(+)-4-phenyl-2-oxazolidinone (8.86 g, 54 mmol) in anhydrous tetrahydrofuran (130 mL) under nitrogen at −78° C. was added dropwise a solution of n-butyl lithium (22 mL, 54 mmol, 2.5 M in hexanes). The mixture was stirred at −78° C. for 20 minutes and then transferred via a cannula into the reaction flask containing the mixed anhydride at −78° C. The reaction mixture was stirred at 0° C. for 1 hour, then warmed to room temperature and stirred for 18 hours. The mixture was quenched with saturated aqueous ammonium chloride solution (200 mL), concentrated to about half of its original volume under reduced pressure to remove tetrahydrofuran. The remaining mixture was extracted with ethyl acetate (2×250 mL). The organic layer was separated, combined, dried over sodium sulfate and concentrated under reduced pressure. The residue was purified by chromatography over silica gel eluted with 2:1 ethyl acetate/hexanes to give (S)-3-((E)-pent-2-enoyl)-4-phenyl-oxazolidin-2-one as a white foam (9.9 g, 75%).

(2) To a suspension of copper (I) bromide dimethyl sulfide complex (12.4 g, 60.6 mmol) in dry tetrahydrofuran (150 mL) at −10° C. was added phenyl magnesium chloride solution (30.3 mL, 60.6 mmol, 2 M in tetrahydrofuran). The reaction mixture was stirred at −10° C. for 1 hour, then a solution of (S)-3-((E)-pent-2-enoyl)-4-phenyl-oxazolidin-2-one (9.9 g, 40.4 mmol) in tetrahydrofuran (100 mL) was added dropwise via cannula. The reaction mixture was stirred at −10° C. for 0.5 hours, then at room temperature for 2 hours. The mixture was quenched with saturated aqueous ammonium chloride solution (150 mL), concentrated under reduced pressure to half of its volume. The mixture was extracted with ethyl acetate (2×250 mL). The organic layer was separated, combined and dried over sodium sulfate and concentrated under reduced pressure. The residue was purified by chromatography over silica gel eluted with 2:1 ethyl acetate/hexanes to give (S)-4-phenyl-3-((R)-3-phenyl-pentanoyl)-oxazolidin-2-one as a colorless oil which solidified on standing at room temperature (9.56 g, 73%).

(3) To a solution of (S)-4-phenyl-3-((R)-3-phenyl-pentanoyl)-oxazolidin-2-one (8:81 g, 27.2 mmol) in dry tetrahydrofuran (200 mL) under nitrogen at −78° C. was added potassium hexamethyldisilazide (45 mL, 40.8 mmol, 0.91 M in tetrahydrofuran). The reaction mixture was stirred at −78° C. for 1 hour, then a pre-cooled solution of 2,4,6-triisopropylbenzenesulfonyl azide (9.6 g, 31 mmol) in tetrahedrofuran (200 mL) at −78° C. was added dropwise via cannula. The reaction mixture was stirred at −78° C. for 1.5 hours and then acetic acid (7.5 g, 125 mmol) was added. The reaction mixture was warmed to 35° C. in a water bath and stirred for 2 hours, during which period of time thin layer chromatography analysis indicated the formation of desired product as a major component. The reaction mixture was concentrated to a smaller volume, then poured into water, and extracted with ethyl acetate (2×200 mL). The organic layers were separated, combined, dried over sodium sulfate and concentrated. The residue was purified by chromatography over silica gel eluted with 2:1 dichloromethane/hexanes to give (S)-3-((2S,3S)-2-azido-3-phenyl-pentanoyl)-4-phenyl-oxazolidin-2-one as a white solid. Further purification by precipitation of an ethyl acetate solution with hexanes yielded the product as a white solid (6.08 g, 36%).

(4) To a solution of (S)-3-((2S,3S)-2-azido-3-phenyl-pentanoyl)-4-phenyl-oxazolidin-2-one (4.0 g, 11 mmol) and di-tert-butyl dicarbonate (4.8 g, 22 mmol) in ethyl acetate (100 mol) was added 10% palladium on carbon (2 g) under nitrogen. The resulting suspension was vigorously shaken under an atmosphere of hydrogen (55 psi) in a Parr apparatus for 20 hours. The mixture was then filtered through a short pad of celite and the filtrate was concentrated. The residue was purified by chromatography over silica gel eluted with 1:4 ethyl acetate/hexanes to give [(1S,2S)-1-((S)-2-oxo-4-phenyl-oxazolidine-3-carbonyl)-2-phenyl-butyl]-carbamic acid tert-butyl ester as a white foam (4.38 g, 90%).

(5) To a solution of [(1S,2S)-1-((S)-2-oxo-4-phenyl-oxazolidine-3-carbonyl)-2-phenyl-butyl]-carbamic acid tert-butyl ester (4.38 g, 10 mmol) in a mixture of tetrahydrofuran and water (3:1, 60 mL) at −10° C. was added sequentially a solution of hydrogen peroxide in water (11 mL, 100 mmol, 30%) and an aqueous solution (15 mL) of lithium hydroxide monohydrate (1.23 g, 30 mmol). The reaction mixture was stirred at −10° C. and the progress of the reaction was monitored by thin layer chromatography. After 3 hours, TLC analysis indicated almost complete consumption of starting material. Saturated aqueous sodium sulfite solution (100 mL) was added. The mixture was concentrated to half of its original volume under reduced pressure to remove tetrahydrofuran and then extracted with dichloromethane (2×100 mL). The aqueous layer was separated, acidified to pH=2-3 with aqueous citric acid solution and extracted with ethyl acetate (2×300 mL). The organic layers were separated, combined and dried over sodium sulfate, concentrated under reduced pressure and dried in vacuo to give (2S,3S)-2-tert-butoxycarbonylamino-3-phenyl-pentanoic acid as a white foam (1.7 g, 58%).

(6) In a manner similar to that described in Example 1, (2S,3S)-N-(4-acetyl-thiazol-2-yl)-2-[(R)-4-(4-methoxy-phenyl)-2,5-dioxo-imidazolidin-1-yl]-3-phenyl-pentanoic acid (4-acetyl-thiazol-2-yl)-amide (RO4922706) was prepared from (2S,3S)-2-tert-butoxycarbonylamino-3-phenyl-pentanoic acid and 1-(2-amino-thiazol-4-yl)-ethanone.

HRMS: Obs. Mass, 507.1701. Calcd. Mass, 507.1697 (M+H).

EXAMPLE 4

(2S,3S)-2-[(R)-4-(4-Methoxy-phenyl)-2,5-dioxo-imidazolidin-1-yl]-3-phenyl-N-(4-propionyl-thiazol-2-yl)-butyramide

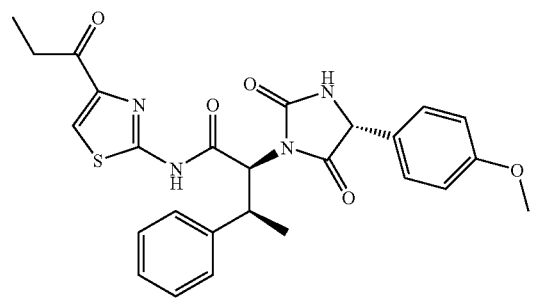

(1) 2-Amino-thiazole-4-carboxylic acid ethyl ester (Kumar, R.; Rai, D. et al. *Heterocyclic Communications* 2002, 8, 521-530) (34.44 g, 0.20 mol) and di-tert-butyl dicarbonate (65.47 g, 0.30 mol) in pyridine (1000 mol) were heated at reflux for 4.5 hours. More di-tert-butyl dicarbonate (65.47 g, 0.3 mol) was added and refluxing continued for 1.5 hours. The reaction mixture was partitioned between ethyl acetate and water. The organic phase was washed well with water, dried (magnesium sulfate) and evaporated. Chromatography of the residue over silica gel using 3:1 ethyl acetate/dichloromethane gave 2-tert-butoxycarbonylamino-thiazole-4-carboxylic acid ethyl ester as a tan solid (52.35 g, 96%).

(2) Lithium hydroxide monohydrate (20.16 g, 0.48 mol) was added to a stirred solution of 2-tert-butoxycarbonylamino-thiazole-4-carboxylic acid ethyl ester (52.35 g, 0.192 mol) in a mixture of tetrahydrofuran (800 mL) and water (200 mL). The mixture was stirred over night. 1 N Aqueous hydrochloric acid (480 mL) was added and the reaction mixture concentrated in vacuo to remove tetrahydrofuran. The mixture was then diluted with water and filtered. The solid was washed with water, ether and dried overnight to give 2-tert-butoxycarbonylamino-thiazole-4-carboxylic acid (43.9 g, 94%).

(3) A solution of 2-tert-butoxycarbonylamino-thiazole-4-carboxylic acid (14 g, 0.0573 mol), 2-chloro-4,6-dimethoxy-1,3,5-triazine (10.06 g, 0.0573 mol) and N-methyl morpholine (5.79 g, 0.0573 mol) in tetrahydrofuran was stirred for 2 hours at room temperature. N,O-Dimethylhydroxylamine hydrochloride (5.59 g, 0.0573 mmol) and triethylamine (5.59 g, 0.0573 mol) were added and the mixture was stirred for 3 days. The reaction mixture was evaporated and ethyl acetate was added. The reaction mixture was washed with 1 N aqueous hydrochloric acid and then washed with saturated aqueous sodium bicarbonate. [4-(Methoxy-methyl-carbamoyl)-thiazol-2-yl]-carbamic acid tert-butyl ester (14.5 g, 88%) was obtained as a tan tar after drying (magnesium sulfate) and evaporation.

(4) A solution of ethyl magnesium chloride (126 mL, 0.252 mol, 2 M in tetrahydrofuran) was stirred and cooled to −70° C. on a dry ice/acetone bath. A solution of [4-(methoxy-methyl-carbamoyl)-thiazol-2-yl]-carbamic acid tert-butyl ester (14.5 g, 0.0504 mol) in tetrahydrofuran (200 mL) was added dropwise over approximately 5 minutes. The mixture was stirred for 1 hour. The cooling bath was removed and stirring continued for an additional 2 hours. The mixture was poured into a mixture of ice and saturated aqueous ammonium chloride solution and then extracted with ethyl acetate. The organic extracts were combined, washed with brine, dried over magnesium sulfate and evaporated to give an off white solid which was purified by chromatography over a 350 g pad of silica gel eluted with 4:1 ethyl acetate/dichloromethane to afford (4-propionyl-thiazol-2-yl)-carbamic acid tert-butyl ester (7.09 g, 55%) as an off white solid.

(5) (4-Propionyl-thiazol-2-yl)-carbamic acid tert-butyl ester (5.0 g, 19.5 mmol) was suspended in dichloromethane (100 mL) at 0° C. Trifluoroacetic acid (100 mL) was added and the mixture was stirred at 0° C. for 1.5 hours. The cooling bath was removed and stirring was continued for 1 hour prior to concentration of the reaction mixture in vacuo. The residue was triturated with ether and filtered. The solid was dissolved in a mixture of dichloromethane and saturated aqueous sodium bicarbonate solution. The organic layer was separated and the aqueous layer was extracted with dichloromethane. The combined organic extracts were washed with brine, dried over sodium sulfate and evaporated to give 1-(2-amino-thiazol-4-yl)-propan-1-one (2.3 g, 75%).

(6) In a similar manner as that described in Example 1, (2S,3S)-2-[(R)-4-(4-methoxy-phenyl)-2,5-dioxo-imidazolidin-1-yl]-3-phenyl-N-(4-propionyl-thiazol-2-yl)-butyramide was prepared from (2S,3S)-2-tert-butoxycarbonylamino-3-phenyl-butyric acid and 1-(2-amino-thiazol-4-yl)-propan-1-one.

HRMS: Obs. Mass, 507.1697. Calcd. Mass, 507.1097 (M+H).

EXAMPLE 5

In a manner similar to that described in Example 4, the following compounds were prepared.

a) (2S,3S)-N-(4-Acetyl-thiazol-2-yl)-2-[(R)-4-(2,3-dihydro-benzo[1,4]dioxin-6-yl)-2,5-dioxo-imidazolidin-1-yl]-3-phenyl-N-(4-propionyl-thiazol-2-yl)-butyramide.

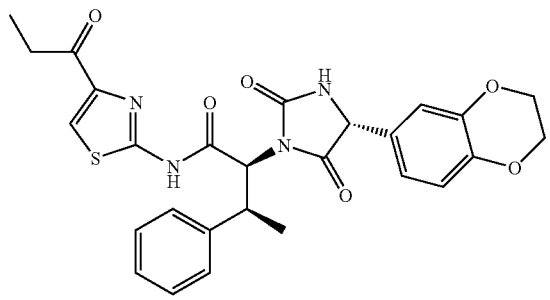

(2R)-tert-Butoxycarbonylamino-(2,3-dihydro-benzo[1,4]dioxin-6-yl)-acetic acid was prepared according to the procedure described by Bohme, E. H. W. et al., *J. Med. Chem.* 1980, 23, 405412.

HRMS: Obs. Mass, 535.1645. Calcd. Mass, 535.1646 (M+H).

b) (2S,3S)-2-[(R)-4-(4-Ethoxy-phenyl)-2,5-dioxo-imidazolidin-1-yl]-3-phenyl-N-(4-propionyl-thiazol-2-yl)-butyramide.

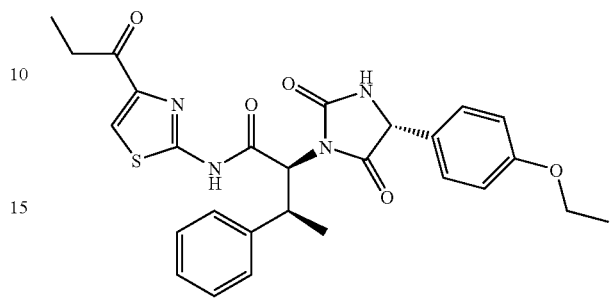

(R)-tert-Butoxycarbonylamino-{4-ethoxyphenyl}-acetic acid, which was used in place of (R)-tert-butyloxycarbonylamino-(4-methoxyphenylglycine) in Example 1d, was prepared in a similar manner as described for the synthesis of (R)-tert-butoxycarbonylamino-{4-[2-(tetrahydro-pyran-2-yloxy)-ethoxy]-phenyl}-acetic acid in Example 2b.

HRMS: Obs. Mass, 611.2166. Calcd. Mass, 611.2170 (M+H).

c) (2S,3S)-2-[(R)-4-(4-Hydroxy-phenyl)-2,5-dioxo-imidazolidin-1-yl]-3-phenyl-N-(4-propionyl-thiazol-2-yl)-butyramide.

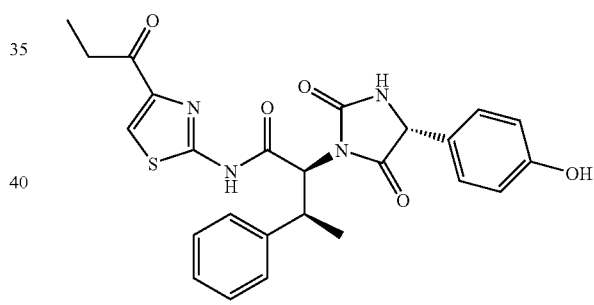

LR-MS: 493 (M+H).

d) (2S,3S)-2-{(R)-4-[4-(2-Methoxy-ethoxy)-phenyl]-2,5-dioxo-imidazolidin-1-yl}-3-phenyl-N-(4-propionyl-thiazol-2-yl)-butyramide.

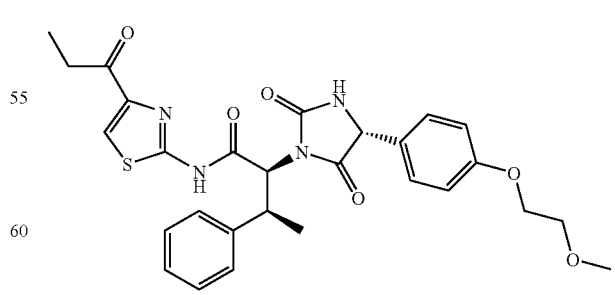

(R)-tert-Butoxycarbonylamino-[4-(2-methoxy-ethoxy)-phenyl]-acetic acid, which was used in place of (R)-tert-butyloxycarbonylamino-4-methoxyphenylglycine in Example 1d, was prepared in a similar manner as described for the synthesis of (R)-tert-butoxycarbonylamino-{4-[2-(tetrahydro-pyran-2-yloxy)-ethoxy]-phenyl}-acetic acid in Example 2b.

HRMS: Obs. Mass, 551.1958. Calcd. Mass, 551.1959 (M+H).

e) (2S,3S)-2-{(S)-4-[4-(2-Methoxy-ethoxy)-phenyl]-2,5-dioxo-imidazolidin-1-yl}-3-phenyl-N-(4-propionyl-thiazol-2-yl)-butyramide was isolated as a by product from the synthesis of (2S,3S)-2-{(R)-4-[4-(2-methoxy-ethoxy)-phenyl]-2,5-dioxo-imidazolidin-1-yl}-3-phenyl-N-(4-propionyl-thiazol-2-yl)-butyramide.

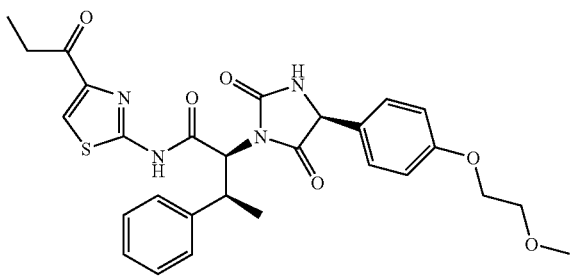

HRMS: Obs. Mass, 551.1692. Calcd. Mass, 551.1959 (M+H).

f) (2S,3S)-2-{(R)-4-[4-(2-Hydroxy-ethoxy)-phenyl]-2,5-dioxo-imidazolidin-1-yl}-3-phenyl-N-(4-propionyl-thiazol-2-yl)-butyramide.

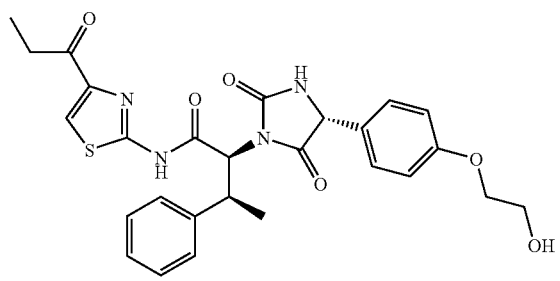

(R)-tert-Butoxycarbonylamino-{4-[2-(tetrahydro-pyran-2-yloxy)-ethoxy]-phenyl}-acetic acid, which was used in place of (R)-tert-butyloxycarbonylamino-4-methyoxyphenylglycine in Example 1d, was prepared in Example 2b.

HRMS: Obs. Mass, 537.1804. Calcd. Mass, 537.1803 (M+H).

g) (2S,3S)-2-((R)-4-{4-[2-(2-Methoxy-ethoxy)-ethoxy]-phenyl}-2,5-dioxo-imidazolidin-1-yl)-3-phenyl-N-(4-propionyl-thiazol-2-yl)-butyramide.

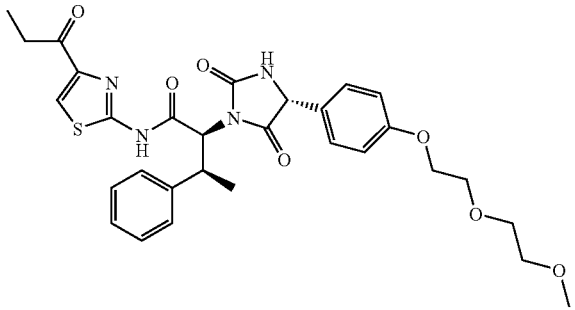

(R)-tert-Butoxycarbonylamino-{4-[2-(2-methoxy-ethoxy)-ethoxy]-phenyl}-acetic acid, which was used in place of (R)-tert-butyloxycarbonylamino-4-methyoxyphenylglycine in Example 1d, was prepared in a similar manner as described for the synthesis of (R)-tert-butoxycarbonylamino-{4-[2-(tetrahydro-pyran-2-yloxy)-ethoxy]-phenyl}-acetic acid in Example 2b.

HRMS: Obs. Mass, 595.2217. Calcd. Mass, 595.2221 (M+H).

h) (2S,3S)-2-{(R)-4-[4-(2-Ethoxy-ethoxy)-phenyl]-2,5-dioxo-imidazolidin-1-yl}-3-phenyl-N-(4-propionyl-thiazol-2-yl)-butyramide.

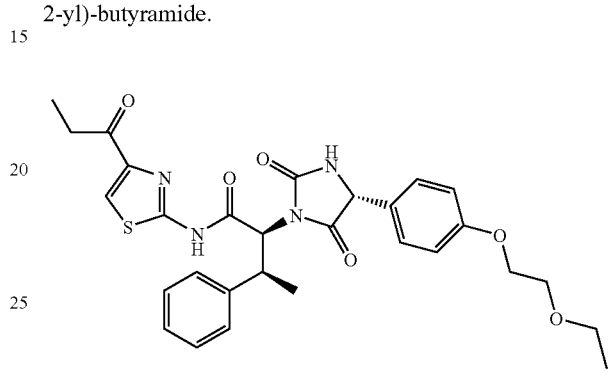

(R)-tert-Butoxycarbonylamino-[4-(2-ethoxy-ethoxy)-phenyl]-acetic acid, which was used in place of (R)-tert-butyloxycarbonylamino-4-methyoxyphenylglycine in Example 1d, was prepared in a similar manner as described for the synthesis of (R)-tert-butoxycarbonylamino-{4-[2-(tetrahydro-pyran-2-yloxy)-ethoxy]-phenyl}-acetic acid in Example 2b.

HRMS: Obs. Mass, 565.2120. Calcd. Mass, 565.2116 (M+H).

i) (2S,3S)-2-{(R)-4-[4-(2-Dimethylamino-ethoxy)-phenyl]-2,5-dioxo-imidazolidin-1-yl}-3-phenyl-N-(4-propionyl-thiazol-2-yl)-butyramide, trifluoro-acetic acid salt.

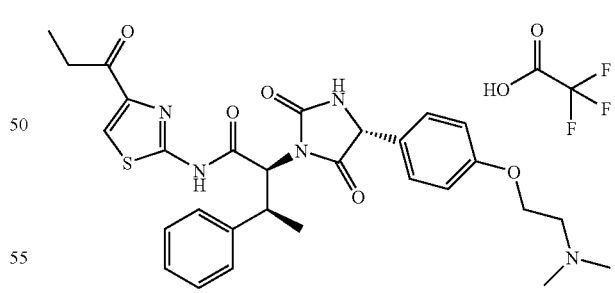

(R)-tert-Butoxycarbonylamino-[4-(2-dimethylamino-ethoxy)-phenyl]-acetic acid, which was used in place of (R)-tert-butyloxycarbonylamino-4-methyoxyphenylglycine in Example 1d, was prepared in a similar manner as described for the synthesis of (R)-tert-butoxycarbonylamino-[4-(2-diethylamino-ethoxy)-phenyl]-acetic acid in Example 2g.

HRMS: Obs. Mass, 564.2266, Calcd. Mass, 564.2275 (M+H).

j) (4-{(R)-2,5-Dioxo-1-[(1S,2S)-2-phenyl-1-(4-propionyl-thiazol-2-ylcarbamoyl)-propyl]-imidazolidin-4-yl}-phenoxymethyl)-phosphonic acid dimethyl ester.

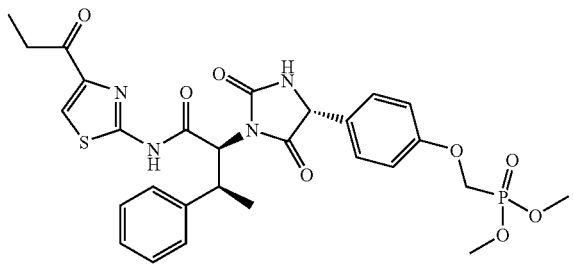

(R)-tert-Butoxycarbonylamino-{4-phenoxymethyl)-phosphonic acid dimethyl ester}-acetic acid, which was used in place of (R)-tert-butyloxycarbonylamino-4-methoxyphenylglycine in Example 1, was prepared as described in example 8h.

HRMS: Obs. Mass, 615.1670. Calcd. Mass, 615.1673 (M+H).

k) (2S,3S)-N-(4-Isobutyryl-thiazol-2-yl)-2-{(R)-4-[4-(2-methoxy-ethoxy)-phenyl]-2,5-dioxo-imidazolidin-1-yl}-3-phenyl-butyramide.

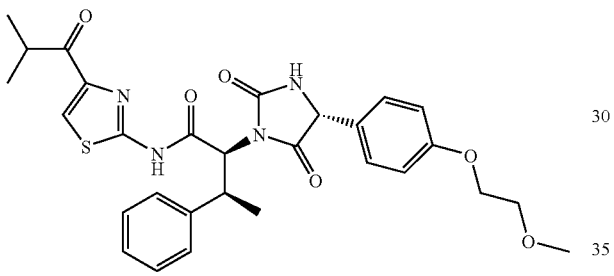

(R)-tert-Butoxycarbonylamino-[4-(2-methoxy-ethoxy)-phenyl]-acetic acid, which was used in place of (R)-tert-butyloxycarbonylamino-4-methyoxyphenylglycine in Example 1d, was prepared in a similar manner as described for the synthesis of (R)-tert-butoxycarbonylamino-{4-[2-(tetrahydro-pyran-2-yloxy)-ethoxy]-phenyl}-acetic acid in Example 2b.

1-(2-Amino-thiazol-4-yl)-2-methyl-propan-1-one, which was used in place of 1-(2-amino-thiazol-4-yl)-ethanone in Example 1c, was prepared in a similar manner as described for the synthesis 1-(2-amino-thiazol-4-yl)-propan-1-one in Example 4.

HRMS: Obs. Mass, 565.2116. Calcd. Mass, 565.2116 (M+H).

l) (2S,3S)-N-(4-Isobutyryl-thiazol-2-yl)-2-[(R)-4-(4-methoxy-phenyl)-2,5-dioxo-imidazolidin-1-yl]-3-phenyl-butyramide.

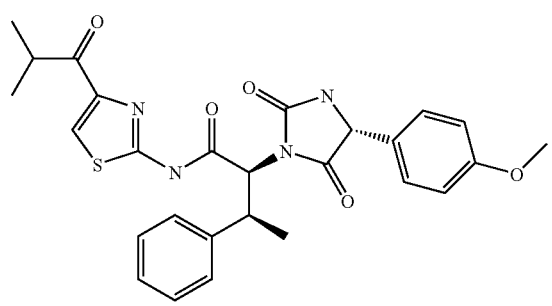

1-(2-Amino-thiazol-4-yl)-2-methyl-propan-1-one, which was used in place of 1-(2-amino-thiazol-4-yl)-ethanone in Example 1c, was prepared in a similar manner as described for the synthesis 1-(2-amino-thiazol-4-yl)-propan-1-one in Example 4.

HRMS: Obs. Mass, 521.1852. Calcd. Mass, 521.1853 (M+H).

m) (2S,3S)-2-{(S)-4-[4-(2-Dimethylamino-ethoxy)-phenyl]-2,5-dioxo-imidazolidin-1-yl}-3-phenyl-N-(4-propionyl-thiazol-2-yl)-butyramide, trifluoro-acetic acid.

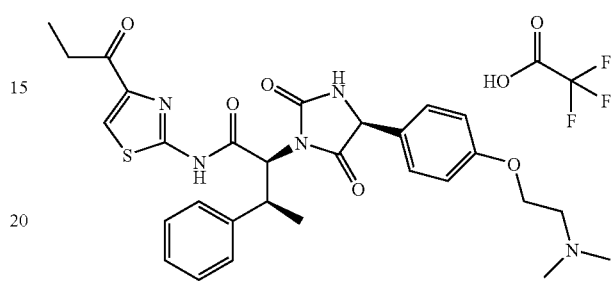

(2S,3S)-2-{(S)-4-[4-(2-Dimethylamino-ethoxy)-phenyl]-2,5-dioxo-imidazolidin-1-yl}-3-phenyl-N-(4-propionyl-thiazol-2-yl)-butyramide was isolated as the minor isomer following the last step in the preparation described in Example 5i.

HRMS: Obs. Mass, 564.2274, Calcd. Mass, 564.2275 (M+H).

n) (2S,3S)-2-{2,5-Dioxo-4-[4-(2-piperidin-1-yl-ethoxy)-phenyl]-imidazolidin-1-yl}-3-phenyl-N-(4-propionyl-thiazol-2-yl)-butyramide.

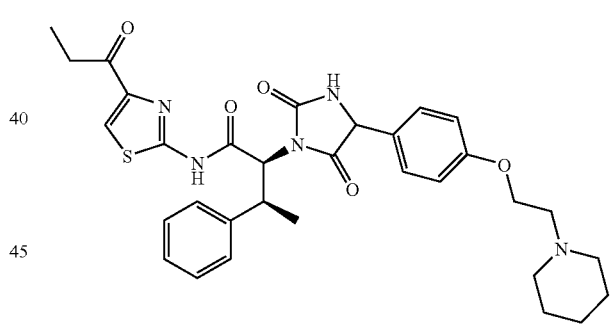

(1) A solution of (R)-N-(tert-butyloxycarbonyl-(4-hydroxyphenylglycine) (1 g, 3.74 mmol) in dry N,N-dimethylformamide (35 mL) was treated with sodium hydride (60% suspention in mineral oil) (470 mg, 11.97 mmol) at 0° C. After 10 minutes the reaction mixture was warmed to room temperature stirred for an additional 10 minutes at that temperature and then treated with 1-(2-chloroethyl)piperidine hydrochloride (720 mg, 2.93 mmol) and potassium iodide (310 mg, 1.87 mmol). After stirring for 15 minutes, additional of dry N,N-dimethylformamide (50 mL) was added and and the resulting slurry was allowed to stir for 27.5 hours. The reaction mixture was then partitioned between ethyl acetate and water and the aqueous layer adjusted to pH=7 with 1N aqueous hydrochloric acid. The aqueous layer was then lyophilized to give a solid residue that was suspended in tetrahydrofuran and filtered. The solids were washed with tetrafydrofuran (2×) and the combined filtrates concentrated to afford crude (R)-tert-butoxycarbonylamino-[4-(2-piperidin- 1-yl-ethoxy)-phenyl]-acetic acid (1.9 g) which was used immediately without further purification.

(2) (R)-tert-Butoxycarbonylamino-[4-(2-piperidin-1-yl-ethoxy)-phenyl]-acetic acid (740 mg, ≈1.96 mmol) was dissolved in tetrahydrofuran (30 mL) and (2S,3S)-2-amino-3-phenyl-N-(4-propionyl-thiazol-2-yl)-butyramide (250 mg, 0.78 mmol) (prepared as described in example 4) was added followed by 1-[3-(dimethylamino)propyl]-3-ethylcarbodiimide hydrochloride (180 mg, 0.94 mmol) at 0° C. The reaction mixture was allowed to slowly warm to room temperature. After stirring for 3.5 hours additional (R)-tert-butoxycarbonylamino-[4-(2-piperidin-1-yl-ethoxy)-phenyl]-acetic acid (320 mg, ≈0.85 mmol) was added to the reaction mixture. After stirring for an additional 1.5 hours an additional aliquot of (R)-tert-butoxycarbonylamino-[4-(2-piperidin-1-yl-ethoxy)-phenyl]-acetic acid (300 mg, ≈0.82 mmol) was added to the reaction mixture along with additional 1-[3-(dimethylamino)propyl]-3-ethylcarbodiimide hydrochloride (90 mg, 4.72 mmol). After stirring at room temperature for an additional 1 hour the mixture was partitioned between ethyl acetate and brine, the organic extract was dried over sodium sulfate, concentrated in vacuo and the resulting residue purified by chromatography over silica gel eluted first with ethyl acetate and then gradient eluted with dichloromethane containing from 0 to 10% methanol. {(R)-[(1S,2S)-2-Phenyl-1-(4-propionyl-thiazol-2-ylcarbamoyl)-propylcarbamoyl]-[4-(2-piperidin-1-yl-ethoxy)-phenyl]-methyl}-carbamic acid tert-butyl ester was obtained as a white solid (120 mg, 24%).

HRMS: Obs. Mass, 678.3323. Calcd. Mass, 678.3320 (M+H).

(3) {(R)-[(1S,2S)-2-Phenyl-1-(4-propionyl-thiazol-2-ylcarbamoyl)-propylcarbamoyl]-[4-(2-piperidin-1-yl-ethoxy)-phenyl]-methyl}-carbamic acid tert-butyl ester (110 mg, 0.16 mmol) was dissolved in a 30% v/v solution of trifluoroacetic acid in dichloromethane (5 mL) at 0° C. After stirring for 1.5 hours the reaction mixture was partitioned between ethyl acetate and saturated aqueous sodium bicarbonate solution. The aqueous layer was adjusted to pH=8 by the addition of solid sodium bicarbonate. The aqueous layer was again extracted with ethyl acetate (2×). The combined organic layers was dried over sodium sulfate, filtered and concentrated in vacuo to give crude (2S,3S)-2-{(R)-2-amino-2-[4-(2-piperidin-1-yl-ethoxy)-phenyl]-acetylamino}-3-phenyl-N-(4-propionyl-thiazol-2-yl)-butyramide which was used immediately and without further purification.

(4) Crude (2S,3S)-2-{(R)-2-amino-2-[4-(2-piperidin-1-yl-ethoxy)-phenyl]-acetylamino}-3-phenyl-N-(4-propionyl-thiazol-2-yl)-butyramide (≈0.16 mmol) was dissolved in tetrahydrofuran (10 mL) that contained diisopropylethylamine (142 μL, 105 mg, 0.81 mmol) and was transferred via cannula to a solution of diphosgene (14 μL, 23 mg, 0.12 mmol) in tetrahydrofuran (15 mL) at 0° C. The reaction mixture was stirred for 20 minutes and then partitioned between ethyl acetate and water. The organic layer was separated and dried over sodium sulfate, filtered and concentrated in vacuo. The residue was purified by chromatography over silica gel eluted first with ethyl acetate and then gradient eluted with dichloromethane containing from 0 to 10% methanol. Precipitation of the isolated product from dichloromethane with an excess of hexanes gave (2S,3S)-2-{2,5-dioxo-4-[4-(2-piperidin-1-yl-ethoxy)-phenyl]-imidazolidin-1-yl}-3-phenyl-N-(4-propionyl-thiazol-2-yl)-butyramide as a white solid (26 mg, 27%).

HRMS: Obs. Mass, 604.2591. Calcd. Mass, 604.2588 (M+H).

o) (2S,3S)-2-{4-[4-(2-Morpholin-4-yl-ethoxy)-phenyl]-2,5-dioxo-imidazolidin-1-yl}-3-phenyl-N-(4-propionyl-thiazol-2-yl)-butyramide.

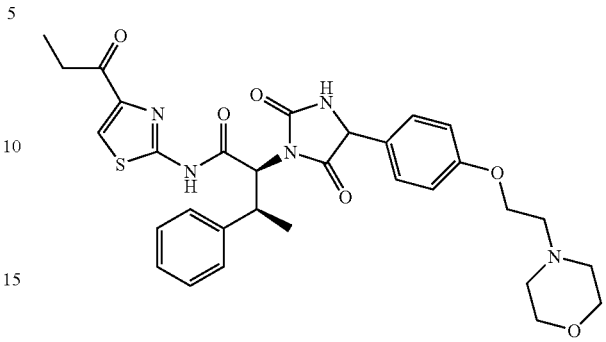

(1) A solution of (R)-N-(tert-butyloxycarbonyl-(4-hydroxyphenylglycine) (1 g, 3:74 mmol) in dry N,N-dimethylformamide (70 mL) was treated with sodium hydride (60% suspension in mineral oil) (470 mg, 11.97 mmol) at 0° C. After 10 minutes the reaction mixture was warmed to room temperature stirred for an additional 10 minutes at that temperature and then treated with N-(2-chloroethyl)morpholine hydrochloride (720 mg, 2.93 mmol) and potassium iodide (61 mg, 0.37 mmol). The reaction mixture was stirred at ambient temperature for 27.5 hours and then partitioned between ethyl acetate and water. The aqueous layer was adjusted to pH=7 with 1N aqueous hydrochloric acid. The aqueous layer was then lyophilized to give a solid residue that was suspended in tetrahydrofuran and filtered. The solids were washed with tetrafydrofuran (2×) and the combined filtrates concentrated to afford crude (R)-tert-butoxycarbonylamino-[4-(2-morpholin-4-yl-ethoxy)-phenyl]-acetic acid which was used immediately without further purification.

(2) (R)-tert-butoxycarbonylamino-[4-(2-morpholin-4-yl-ethoxy)-phenyl]-acetic acid (≈2.93 mmol) was dissolved in tetrahydrofuran (60 mL) and (2S,3S)-2-amino-3-phenyl-N-(4-propionyl-thiazol-2-yl)-butyramide (500 mg, 1.58 mmol) (prepared as described in example 4) was added followed by 1-[3-(dimethylamino)propyl]-3-ethylcarbodiimide hydrochloride (600 mg, 3.12 mmol) at 0° C. The reaction mixture was allowed to slowly warm to room temperature. After stirring for 5.5 hours the reaction mixture was partitioned between ethyl acetate and brine, the organic extract was dried over sodium sulfate and concentrated in vacuo. The resulting residue purified by chromatography over silica gel eluted first with ethyl acetate and then gradient eluted with dichloromethane containing from 0 to 10% methanol. {(R)-[4-(2-Morpholin-4-yl-ethoxy)-phenyl]-[(1S,2S)-2-phenyl-1-(4-propionyl-thiazol-2-ylcarbamoyl)-propylcarbamoyl]-methyl}-carbamic acid-tert-butyl ester was obtained as a white solid (146 mg, 14%).

HRMS: Obs. Mass, 680.3118. Calcd. Mass, 680.3113 (M+H).

(3) {(R)-[4-(2-Morpholin-4-yl-ethoxy)-phenyl]-[(1S,2S)-2-phenyl-1-(4-propionyl-thiazol-2-ylcarbamoyl)-propylcarbamoyl]-methyl}-carbamic acid-tert-butyl ester (0.19 mmol) was dissolved in a 30% v/v solution of trifluoroacetic acid in dichloromethane (5 mL) at 0° C. After stirring for 2 hours the reaction mixture was partitioned between ethyl acetate and saturated aqueous sodium bicarbonate solution. The aqueous layer was adjusted to pH=8 by the addition of solid sodium bicarbonate. The aqueous layer was again extracted with ethyl acetate (2×). The combined organic layers was dried over sodium sulfate, filtered and concentrated in vacuo to give crude (2S,3S)-2-{(R)-2-amino-2-[4-(2-morpholin-4-yl-ethoxy)-phenyl]-acetylamino}-3-phenyl-N-(4-propionyl-thiazol-2-yl)-butyramide which was used immediately and without further purification.

(4) Crude (2S,3S)-2-{(R)-2-amino-2-[4-(2-morpholin-4-yl-ethoxy)-phenyl]-acetylamino}-3-phenyl-N-(4-propionyl-thiazol-2-yl)-butyramide (≈0.19 mmol) was dissolved in tetrahydrofuran (10 mL) that contained diisopropylethylamine (160 μL, 122 mg, 0.94 mmol) and was transferred via cannula to a solution of diphosgene (16 μL, 26 mg, 0.13 mmol) in tetrahydrofuran (15 mL) at 0° C. The reaction mixture was stirred for 20 minutes and then partitioned between ethyl acetate and water. The organic layer was separated and dried over sodium sulfate, filtered and concentrated in vacuo. The residue was purified by chromatography over silica gel gradient eluted with 0-100% ethyl acetate in hexanes and the isolated material further purified by preparative thin layer chromatography using silica gel eluted with ethyl acetate. Precipitation of the isolated product from dichloromethane with an excess of hexanes gave (2S,3S)-2-{4-[4-(2-morpholin-4-yl-ethoxy)-phenyl]-2,5-dioxo-imidazolidin-1-yl}-3-phenyl-N-(4-propionyl-thiazol-2-yl)-butyramide as an off white solid (32 mg, 29%).

HRMS: Obs. Mass, 606.2384. Calcd. Mass, 606.2381 (M+H).

p) (2S,3S)-3-(3-Fluoro-phenyl)-2-{(R)-4-[4-(2-methoxy-ethoxy)-phenyl]-2,5-dioxo-imidazolidin-1-yl}-N-(4-propionyl-thiazol-2-yl)-butyramide.

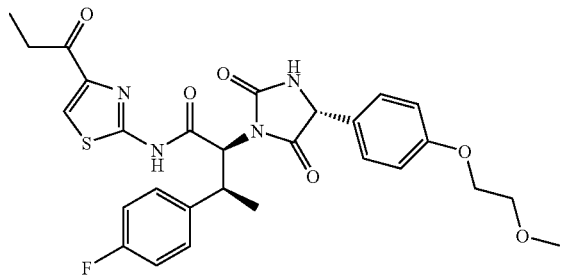

(2S,3S)-2-tert-Butoxycarbonylamino-3-(4-fluoro-phenyl)-butyric acid was prepared in a similar manner as the synthesis of (2S,3S)-2-tert-butoxycarbonylamino-3-phenyl-pentanoic acid as described in Example 3.

HRMS: Obs. Mass, 569.1866. Calcd. Mass, 569.1865 (M+H).

q) (2S,3S)-2-[(R)-4-(4-Methoxy-3-methyl-phenyl)-2,5-dioxo-imidazolidin-1-yl]-3-phenyl-N-(4-propionyl-thiazol-2-yl)-butyramide.

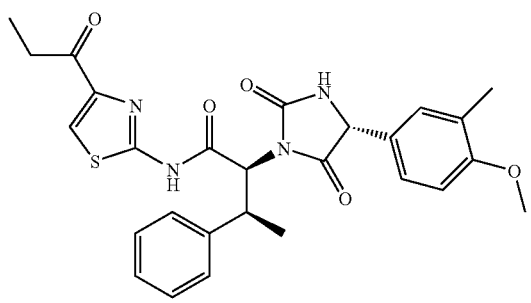

(R)-tert-Butoxycarbonylamino-(4-methoxy-3-methyl-phenyl)-acetic acid was prepared as described in Example 8g.

HRMS: Obs. Mass, 543.1672. Calcd. Mass, 543.1672 (M+H).

r) (2S,3S)-2-{(S)-4-[4-(2-Hydroxy-ethoxy)-phenyl]-2,5-dioxo-imidazolidin-1-yl}-3-phenyl-N-(4-propionyl-thiazol-2-yl)-butyramide.

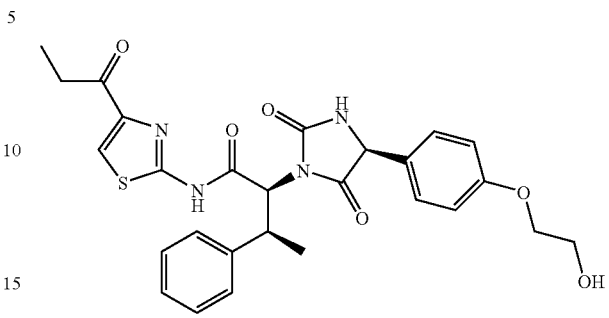

Prepared in a similar way as (2S,3S)-2-{(R)-4-[4-(2-hydroxy-ethoxy)-phenyl]-2,5-dioxo-imidazolidin-1-yl}-3-phenyl-N-(4-propionyl-thiazol-2-yl)-butyramide (Example 5f) except that (S)-4-hydroxyphenylglycine was used in place of (R)-4-hydroxyphenylglycine.

HRMS: Obs. Mass, 537.1802. Calcd. Mass, 537.1803 (M+H).

s) (2S,3S)-2-((R)-2,5-Dioxo-4-phenyl-imidazolidin-1-yl)-3-phenyl-N-(4-propionyl-thiazol-2-yl)-butyramide.

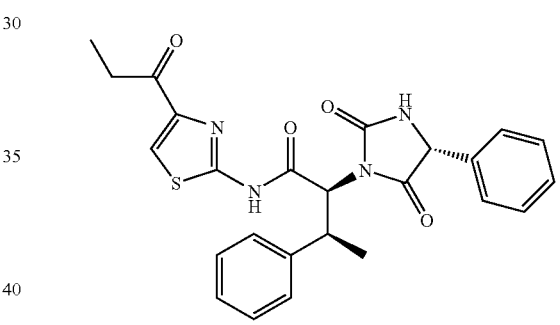

Prepared as described in Example 4 except that (R)-tert-butyloxycarbonylamino-phenylglycine was used in place of (R)-tert-butyloxycarbonylamino-4-methyoxyphenylglycine.

HRMS: Obs. Mass, 477.1595. Calcd. Mass, 477.1591 (M+H).

t) (2S,3S)-2-[4-(4-Dimethylamino-phenyl)-2,5-dioxo-imidazolidin-1-yl]-3-phenyl-N-(4-propionyl-thiazol-2-yl)-butyramide.

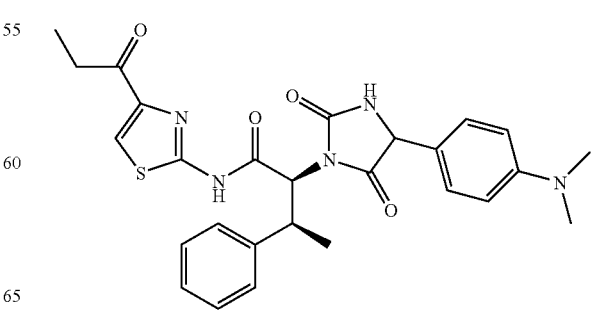

Prepared as described in Example 4 except that tert-butoxycarbonylamino-(4-dimethylamino-phenyl)-acetic acid was used in place of (R)-tert-butyloxycarbonylamino-4-methoxyphenylglycine.

HRMS: Obs. Mass, 520.2015. Calcd. Mass, 520.2013 (M+H).

u) (2S,3S)-2-[4-(4-Morpholin-4-yl-phenyl)-2,5-dioxo-imidazolidin-1-yl]-3-phenyl-N-(4-propionyl-thiazol-2-yl)-butyramide.

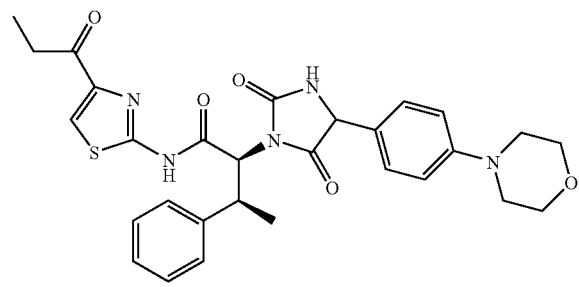

Prepared as described in Example 4 except that tert-butoxycarbonylamino-(4-morpholin-4-yl-phenyl)-acetic acid was used in place of (R)-tert-butyloxycarbonylamino-4-methoxyphenylglycine. tert-Butoxycarbonylamino-(4-morpholin-4-yl-phenyl)-acetic acid was prepared in a similar way as that described in Example 9, step 1, except that 4-morpholin-4-yl-benzaldehyde was used in place of 4-thiomethylbenzaldehyde. 4-Morpholin-4-yl-benzaldehyde was prepared as follows:

A mixture of 2-(4-iodo-phenyl)-[1,3]dioxolane (960 mg, 3.477 mmol), 18-crown-6 ether (1.021 g, 3.85 mmol), tris(dibenzylideneacetone)dipalladium(0)-chloroform adduct (36.35 mg, 0.0348 mmol), rac-2,2'-bis(diphenylphosphino)-1-1'-binaphthyl (65.54 mg, 0.104 mmol) and sodium-t-butoxide (447.9 mg, 4.52 mmol) were thoroughly degassed with argon. To this mixture under argon was added an argon degassed solution of freshly distilled morpholine (324.6 mg, 3.651 mmol) in dry tetrahydrofuran (8 mL). It was stirred at room temperature for 2 hours, and then heated to reflux for 2 hours. The mixture was cooled to room temperature, taken into ethyl acetate (50 mL) and washed with water (3×50 mL) and back extracted with ethyl acetate (50 mL). The combined organic extracts were dried over sodium sulfate, filtered and concentrated to a residue (1.06 g). The residue was purified by chromatography over a methanol deactivated silica gel column gradient eluted in 5% steps from 0 to 25% ethyl acetate in hexanes. 4-(4-[1,3]Dioxolan-2-yl-phenyl)-morpholine eluted from the column with 20 to 25% ethyl acetate in hexanes. Upon concentration 4-(4-[1,3]dioxolan-2-yl-phenyl)-morpholine was obtained as a tan solid (690 mg, 84.3%).

A mixture of 4-(4-[1,3]dioxolan-2-yl-phenyl)-morpholine (690 mg, 2.933 mmol) in methanol (5 mL) was treated with 10 drops concentrated aqueous hydrochloric acid. The mixture was stirred at room temperature for 1 hour. To this solution was added 5 drops of water and stirring was continued for 2 hours at ambient temperature. The solution was then poured into ethyl acetate (50 mL) and washed with saturated aqueous sodium bicarbonate (2×50 mL) and extracted with ethyl acetate (2×50 mL). The combined organic extracts were dried over sodium sulfate, filtered and concentrated to give 4-morpholin-4-yl-benzaldehyde as a tan waxy solid (550 mg, 98%).

HRMS: Obs. Mass, 562.2120. Calcd. Mass, 562.2119 (M+H).

v) (2S,3S)-2-{4-[4-(4-Hydroxy-piperidin-1-yl)-phenyl]-2,5-dioxo-imidazolidin-1-yl}-3-phenyl-N-(4-propionyl-thiazol-2-yl)-butyramide.

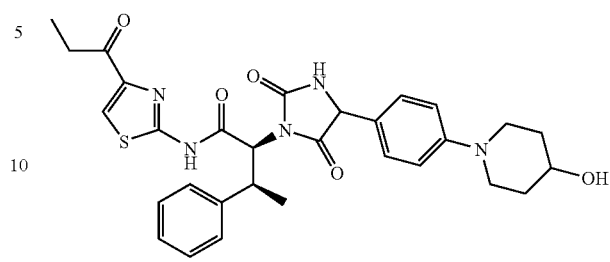

Prepared as described in Example 4 except that tert-butoxycarbonylamino-[4-(4-hydroxy-piperidin-1-yl)-phenyl]-acetic acid was used in place of (R)-tert-butyloxycarbonylamino-4-methyoxyphenylglycine. tert-Butoxycarbonylamino-[4-(4-hydroxy-piperidin-1-yl)-phenyl]-acetic acid was prepared in way similar to that described in Example 5u except that piperidin-4-ol was used in place of morpholine.

HRMS: Obs. Mass, 576.2275. Calcd. Mass, 576.2275 (M+H).

w) (2S,3S)-2-(4-{4-[(2-Methoxy-ethyl)-methyl-amino]-phenyl}-2,5-dioxo-imidazolidin-1-yl)-3-phenyl-N-(4-propionyl-thiazol-2-yl)-butyramide.

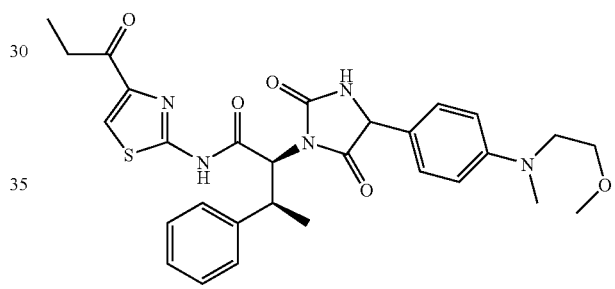

Prepared as described in Example 4 except that tert-butoxycarbonylamino-{4-[(2-methoxy-ethyl)-methyl-amino]-phenyl}-acetic acid was used in place of (R)-tert-butyloxycarbonylamino-4-methyoxyphenylglycine. tert-Butoxycarbonylamino-{4-[(2-methoxy-ethyl)-methyl-amino]-phenyl}-acetic acid was prepared in a similar way as that described in Example 5u except that (2-methoxy-ethyl)-methyl-amine was used in place of morpholine.

HRMS: Obs. Mass, 564.2279. Calcd. Mass, 564.2275 (M+H).

x) (2S,3S)-N-(4-Cyclopropanecarbonyl-thiazol-2-yl)-2-{(R)-4-[4-(2-methoxy-ethoxy)-phenyl]-2,5-dioxo-imidazolidin-1-yl}-3-phenyl-butyramide.

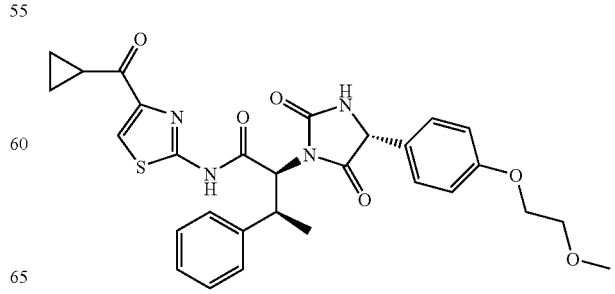

Prepared as described in Example 4 except that cyclopropyl magnesium chloride was used in place of ethyl magnesium chloride in step 4 and (R)-tert-butoxycarbonylamino-[4-(2-methoxy-ethoxy)-phenyl]-acetic acid (prepared as described in example 2c) was used in place of (R)-tert-butyloxycarbonylamino-4-methyoxyphenylglycine.

HRMS: Obs. Mass, 563.1955. Calcd. Mass, 563.1959 (M+H).

y) (2S,3S)-2-{4-[4-(2-Methoxy-ethoxy)-phenyl]-2,5-dioxo-imidazolidin-1-yl}-3-methyl-pentanoic acid (4-propionyl-thiazol-2-yl)-amide.

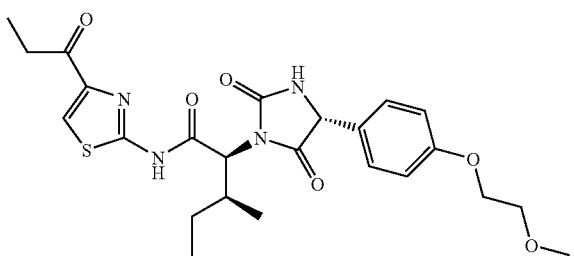

Prepared as described in Example 4 except that (2S,3S)-2-tert-butoxycarbonylamino-3-methyl-pentanoic acid was used in place of (2S,3S)-2-tert-butoxycarbonylamino-3-phenyl-butyric acid and (R)-tert-butoxycarbonylamino-[4-(2-methoxy-ethoxy)-phenyl]-acetic acid (prepared as described in Example 2c) was used in place of (R)-tert-butyloxycarbonylamino-4-methyoxyphenylglycine.

HRMS: Obs. Mass, 503.1961 Calcd. Mass, 503.1959 (M+H).

z) (2S,3R)-3-Benzyloxy-2-{(R)-4-[4-(2-methoxy-ethoxy)-phenyl]-2,5-dioxo-imidazolidin-1-yl}-N-(4-propionyl-thiazol-2-yl)-butyramide.

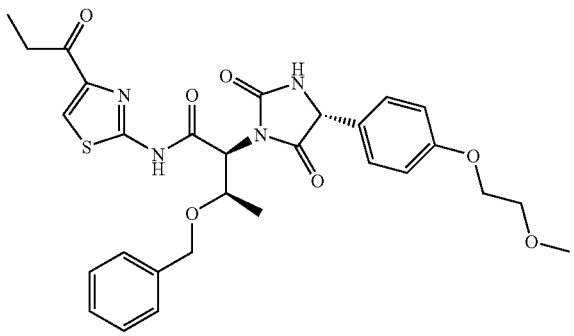

Prepared as described in Example 4 except that (2S,3R)-3-benzyloxy-2-tert-butoxycarbonylamino-butyric acid was used in place of (2S,3S)-2-tert-butoxycarbonylamino-3-phenyl-butyric acid and (R)-tert-butoxycarbonylamino-[4-(2-methoxy-ethoxy)-phenyl]-acetic acid (prepared as described in Example 2c) was used in place of (R)-tert-butyloxycarbonylamino-4-methyoxyphenylglycine.

HRMS: Obs. Mass, 581.2063 Calcd. Mass, 581.2065 (M+H).

EXAMPLE 6

(2S,3S)-N-[4-(2-Methoxy-acetyl)-thiazol-2-yl]-2-[(R)-4-(4-methoxy-phenyl)-2,5-dioxo-imidazolidin-1-yl]-3-phenyl-butyramide

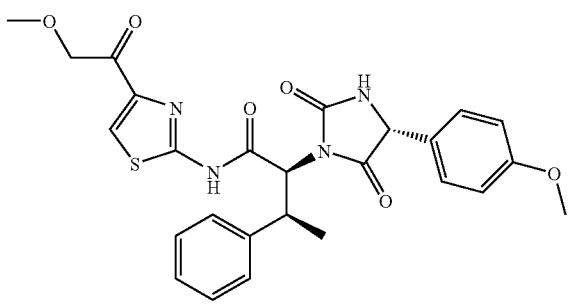

(1) To a solution of [4-(methoxy-methyl-carbamoyl)-thiazol-2-yl]-carbamic acid-tert-butyl ester (17.0 g, 59.2 mmol) (prepared as described in example 4a-4c) in acetonitrile (250 mL) were added potassium carbonate (40.8 g, 295.2 mmol) and 4-dimethylaminopyridine (1.4 g, 11.5 mmol) followed by di-tert-butyl dicarbonate (27.1 g, 124.2 mmol) at room temperature. After stirring for 12 hours, the reaction was filtered through celite and the solvent was removed under vacuum. The crude product was purified by chromatography over silica gel gradient eluted with 30% up to 40% ethyl acetate in hexane to give [4-(methoxy-methyl-carbamoyl)-thiazol-2-yl]-bis-(carbamic acid-tert-butyl ester) (20.1 g, 88% yield).

(2) To a solution of lithium diisopropylamide (13.3 g, 124.1 mmol) in anhydrous tetrahydrofuran (100 mL) chilled to −78° C. was added dropwise, methyl methoxyacetate (12.9 g, 124.3 mmol) in anhydrous tetrahydrofuran (20 mL) at −78° C. The mixture was stirred at −78° C. for 15 minutes. [4-(Methoxy-methyl-carbamoyl)-thiazol-2-yl]-bis-(carbamic acid-tert-butyl ester) (6.0 g, 15.5 mmol) in anhydrous tetrahydrofuran (20 mL) was added dropwise to the anion at −78° C. The mixture was stirred for 30 minutes then quenched with saturated aqueous sodium bicarbonate, extracted with ethyl acetate, washed with brine and dried over sodium sulfate. The crude product was purified by chromatography over silica gel gradient eluted with 10% up to 30% ethyl acetate in hexanes. 3-(2-Bis-tert-butoxycarbonylamino-thiazol-4-yl)-2-methoxy-3-oxo-propionic acid methyl ester was obtained as a white foam (1.54 g, 23%).

(3) To a solution of 3-(2-bis-tert-butoxycarbonylamino-thiazol-4-yl)-2-methoxy-3-oxo-propionic acid methyl ester (1.54 g, 3.6 mmol) in dichloromethane (15 mL) was added trifluoroacetic acid (7.2 mL) at 0° C. The reaction was warmed to room temperature and stirred for 4 hours. The solvent was removed under vacuum and the residue was partitioned between ethyl acetate and saturated aqueous sodium bicarbonate. The aqueous layer was extracted with ethyl acetate and the combined extracts were washed with brine and dried over sodium sulfate. The solvent was removed to give 3-(2-amino-thiazol-4-yl)-2-methoxy-3-oxo-propionic acid methyl ester as an oil (800 mg, 97% yield).

(4) To a solution of 3-(2-amino-thiazol-4-yl)-2-methoxy-3-oxo-propionic acid methyl ester (765 mg, 3.3 mmol) in tetrahydrofuran (25 ml) was added 1M aqueous sodium hydroxide (4.0 ml, 4.0 mmol) at room temperature. The mixture was stirred for 2 hours then cooled to 0° C. 1 N aqueous sulfuric acid (33 mL, 33.2 mmol) was added and the reaction was warmed to 40° C. for 30 minutes. The reaction mixture was then cooled to 0° C. and made basic with saturated aqueous sodium bicarbonate. The suspension was extracted with ethyl acetate, the combined organic extracts washed with water, brine and dried over magnesium sulfate. The crude product was purified by chromatography over silica gel eluted with 7:3 ethyl acetate/hexanes to give 1-(2-amino-thiazol-4-yl)-2-methoxy-ethanone as a yellow oil (240 mg, 42% yield).

(5) In a manner similar as described in example 1, (2S,3S)-N-[4-(2-methoxy-acetyl)-thiazol-2-yl]-2-[(R)-4-(4-methoxy-phenyl)-2,5-dioxo-imidazolidin-1-yl]-3-phenyl-butyramide was prepared from 1-(2-amino-thiazol-4-yl)-2-methoxy-ethanone.

HRMS: Obs. Mass, 507.2888. Calcd. Mass, 507.2887 (M+H).

EXAMPLE 7

2-{(2S,3S)-2-[(R)-4-(2,3-Dihydro-benzo[1,4]dioxin-6-yl)-2,5-dioxo-imidazolidin-1-yl]-3-phenyl-butyrylamino}-thiazole-4-carboxylic acid methyl ester

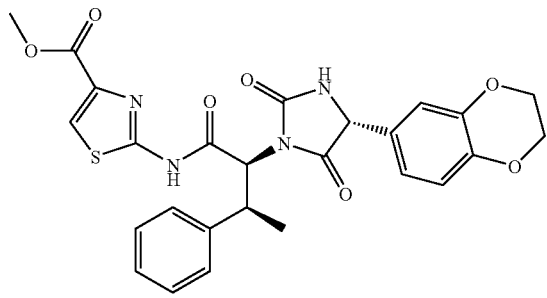

(1) 2-Amino-thiazole-4-carboxylic acid ethyl ester (38 g) (prepared as described in Example 4) in methanol (400 mL) was cooled in an ice bath and to it was added 25% sodium methoxide over 0.5 hours. The ice bath was removed after 0.5 hours. A small amount of isoluble material was removed by filtration and to the yellow solution was added saturated aqueous ammonium chloride and the reaction mixture concentrated to remove excess methanol. The mixture was basified to pH=9.0 with saturated aqueous sodium bicarbonate and extracted with 1:1 ether/tetrahydrofuran (3×200 mL). The combined organic extracts were washed with water. The organic solution was dried over sodium sulfate and concentrated to give a pale yellow solid which still contained some residual solvent. The solid was suspended in hexanes, filtered on a 5.5 cm funnel then dried in vacuo to give 2-amino-thiazole-4-carboxylic acid methyl ester (15.6 g) as a pale yellow solid.

(2) 2-Amino-thiazole-4-carboxylic acid methyl ester (0.57 g, 3.62 mmol) and (2S,3S)-2-tert-butoxycarbonylamino-3-phenyl-butyric acid (Acros) (1.01 g, 3.62 mmol), 1-hydroxybenzotriazole and (0.59 g, 4.34 mmol) and O-benzeotrazol-1-yl-N,N,N',N'-tetramethyluroniumhexaflurorophosphate (1.65 g, 4.34 mmol) in N,N-dimethylformamide (8 mL) were stirred at ambient temperature for 24 hours. The mixture was diluted with ethyl acetate, washed with water, brine and dried (magnesium sulfate). Evaporation of the solvents and chromatography of the residue over silica gel gradient eluted with 0.2-1.5% methanol in dichloromethane gave 2-((2S,3S)-2-tert-butoxycarbonylamino-3-phenyl-butyrylamino)-thiazole-4-carboxylic acid methyl ester (0.65 g, 43%).

(3) 2-((2S,3S)-2-tert-butoxycarbonylamino-3-phenyl-butyrylamino)-thiazole-4-carboxylic acid methyl ester (0.65 g, 1.54 mmol) was mixed in dichloromethane (5 mL) in an ice-bath. Trifluoroacetic acid (5 mL) was added and the solution was stirred for 2 hours. The reaction mixture was evaporated and the residue was precipitated with ether. The mixture was stirred vigorously for 10 minutes and then filtered. The solid was partitioned between aqueous sodium bicarbonate and dichloromethane. The organic layer was separated and the aqueous layer was extracted with dichloromethane. The combined organic extracts were washed with brine and dried (sodium sulfate). Evaporation of the solvents gave 2-((2S,3S)-2-amino-3-phenyl-butyrylamino)-thiazole-4-carboxylic acid methyl ester (0.35 g, 71%).

(4) 2-((2S,3S)-2-Amino-3-phenyl-butyrylamino)-thiazole-4-carboxylic acid methyl ester (0.255 g, 0.80 mmol), (2R)-tert-butoxycarbonylamino-(2,3-dihydro-benzo[1,4]dioxin-6-yl)-acetic acid (prepared according to the procedure of Bohme, E. H. W. et al., J. Med. Chem. 1980, 23, 405-412), O-benzotriazol-1-yl-N,N,N',N'-tetramethyluronium hexaflurorophosphate (0.364 g, 0.96 mmol) and diisopropylethyl amine (0.56 mol, 3.2 mmol) were dissolved in N,N-dimethylformamide (3 mL) in an ice bath. 1-Hydroxybenzotriazole (0.13 g, 9.6 mmol) in N,N-dimethylformamide (1 mL) was added dropwise. Stirring was continued for 30 min at 0° C. The reaction mixture was diluted with ethyl acetate and the mixture was washed with water and brine. The organic layer was diluted with an equal volume of dichloromethane, filtered through a pad of silica gel with a layer of sodium sulfate on the top and eluted with 1:1 ethyl acetate/dichloromethane. Evaporation of the solvents gave a white solid which was triturated with ether/hexane to give crude 2-{(2S,3S)-2-[(R)-2-tert-butoxycarbonylamino-2-(2,3-dihydro-benzo[1,4]dioxin-6-yl)-acetylamino]-3-phenyl-butyrylamino}-thiazole-4-carboxylic acid methyl ester (0.49 g).

(5) 2-{(2S,3S)-2-[(R)-2-tert-Butoxycarbonylamino-2-(2,3-dihydro-benzo[1,4]dioxin-6-yl)-acetylamino]-3-phenyl-butyrylamino}-thiazole-4-carboxylic acid methyl ester (0.49 g, 0.80 mmol) was stirred in dichloromethane (8 mL) in an ice bath. Trifluoroacetic acid (8 mL) was added and the solution was stirred for 2 hours. The reaction mixture was evaporated and the residue was precipitated with hexanes/ether. The mixture was stirred vigorously for 10 minutes and then filtered. The resulting solid was partitioned between aqueous sodium bicarbonate and dichloromethane. The organic layer was separated and the aqueous layer was extracted with dichloromethane. The combined organic extracts were washed with brine and dried (sodium sulfate). Evaporation of the solvents gave 2-{(2S,3S)-2-[(R)-2-amino-2-(2,3-dihydro-benzo[1,4]dioxin-6-yl)-acetylamino]-3-phenyl-butyrylamino}-thiazole-4-carboxylic acid methyl ester (0.384 g, 94%).

(6) A solution of 2-{(2S,3S)-2-[(R)-2-amino-2-(2,3-dihydro-benzo[1,4]dioxin-6-yl)-acetylamino]-3-phenyl-butyrylamino}-thiazole-4-carboxylic acid methyl ester (0.380 g, 0.75 mmol)) and diisopropylethylamine (0.52 mL, 3 mmol) in tetrahydrofuran (7.5 mL) were added to a solution of diphosgene (0.48 mL, 4 mmol) in a mixture of toluene (7.5 mol) and tetrahydrofuran (7.5 mol) over 10 minutes at 0° C. The mixture was stirred at 0° C. for 20 minutes and then diluted with ethyl acetate. The mixture was washed with water, brine and dried (sodium sulfate). Evaporation of the solvents and chromatography of the residue over silica gel gradient eluted with 0.2-1% methanol in dichloromethane gave (2-{(2S,3S)-2-[(R)-4-(2,3-dihydro-benzo[1,4]dioxin-6-yl)-2,5-dioxo-imidazolidin-1-yl]-3-phenyl-butyrylamino}-thiazole-4-carboxylic acid methyl ester (0.22 g, 55%).

HRMS: Obs. Mass, 537.1438. Calcd. Mass, 537.1439 (M+H).

EXAMPLE 8

In a manner similar to that described in Example 7, the following compounds were prepared.

a) 2-[(2S,3S)-2-((R)-2,5-Dioxo-4-phenyl-imidazolidin-1-yl)-3-phenyl-butyrylamino]-thiazole-4-carboxylic acid methyl ester.

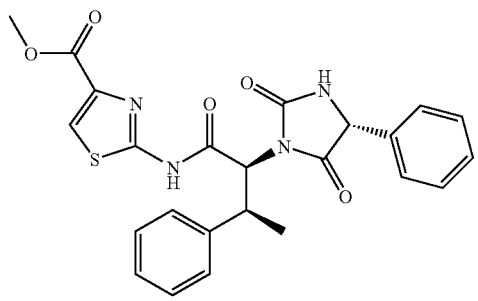

Anal. Calcd. for C$_{24}$H$_{22}$N$_4$O$_5$S.0.2 C$_6$H$_{14}$: C, 61.05; H, 5.04; N, 11.30; S, 6.47. Found: C, 61.27; H, 5.25; N, 10.95; S, 6.10.

b) 2-{(2S,3S)-2-[(R)-4-(4-Methoxy-phenyl)-2,5-dioxo-imidazolidin-1-yl]-3-phenyl-butyrylamino}-thiazole-4-carboxylic acid methyl ester.

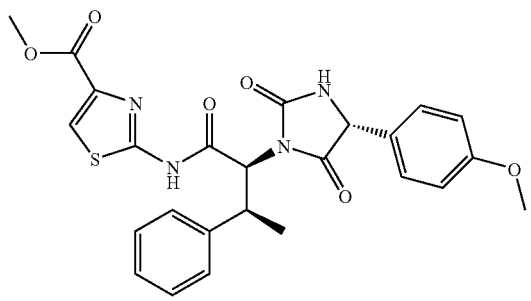

(R)-tert-butyloxycarbonylamino-4-methyoxyphenylglycine (Hyun, M. H.; Cho, Y. K. et al. *J. Liq. Chrom. & Rel. Technol.* 2002, 25, 573-588.) was used in place of (2R)-tert-butoxycarbonylamino-(2,3-dihydro-benzo[1,4]dioxin-6-yl)-acetic acid in Example 7 (step 4).

HRMS: Obs. Mass, 509.1485. Calcd. Mass, 509.1490 (M+H).

c) 2-{(2S,3S)-2-[(R)-4-(4-Hydroxy-phenyl)-2,5-dioxo-imidazolidin-1-yl]-3-phenyl-butyrylamino}-thiazole-4-carboxylic acid methyl ester.

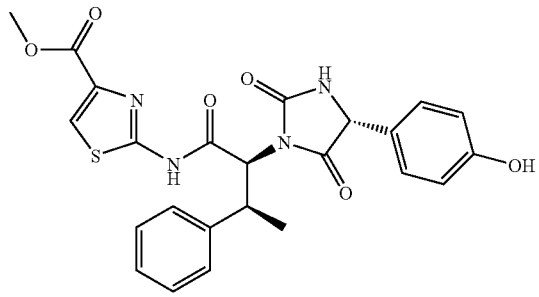

HRMS: Obs. Mass, 495.1334. Calcd. Mass, 495.1333 (M+H).

d) 2-((2S,3S)-2-{(R)-4-[4-(2-Methoxy-ethoxy)-phenyl]-2,5-dioxo-imidazolidin-1-yl}-3-phenyl-butyrylamino)-thiazole-4-carboxylic acid methyl ester.

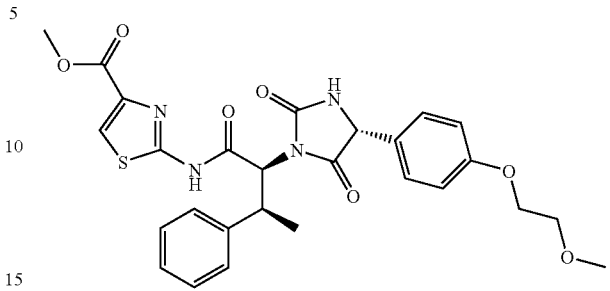

(R)-tert-Butoxycarbonylamino-[4-(2-methoxy-ethoxy)-phenyl]-acetic acid, which was used in place of (2R)-tert-butoxycarbonylamino-(2,3-dihydro-benzo[1,4]dioxin-6-yl)-acetic acid in Example 7 (step 4) was prepared in a similar manner as described for the synthesis of (R)-tert-butoxycarbonylamino-{4-[2-(tetrahydro-pyran-2-yloxy)-ethoxy]-phenyl}-acetic acid in Example 2b.

HRMS: Obs. Mass, 553.1753. Calcd. Mass, 553.1752 (M+H).

e) 2-((2S,3S)-2-{(R)-4-[4-(2-Hydroxy-ethoxy)-phenyl]-2,5-dioxo-imidazolidin-1-yl}-3-phenyl-butyrylamino)-thiazole-4-carboxylic acid methyl ester.

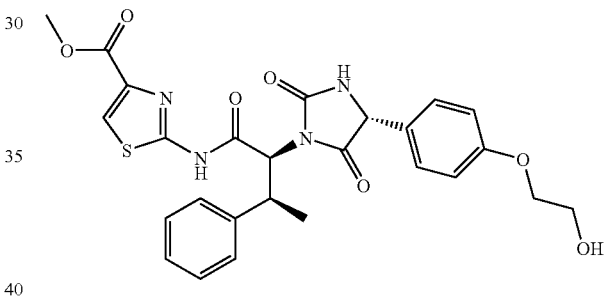

(R)-tert-butoxycarbonylamino-{4-[2-(tetrahydro-pyran-2-yloxy)-ethoxy]-phenyl}-acetic acid, which was used in place of (2R)-tert-butoxycarbonylamino-(2,3-dihydro-benzo[1,4]dioxin-6-yl)-acetic acid in Example 7 (step 4), was prepared as described in Example 2b.

HRMS: Obs. Mass, 539.1595. Calcd. Mass, 539.1595 (M+H).

f) 2-{(2S,3S)-2-[(R)-4-(4-Isopropoxy-phenyl)-2,5-dioxo-imidazolidin-1-yl]-3-phenyl-butyrylamino}-thiazole-4-carboxylic acid methyl ester

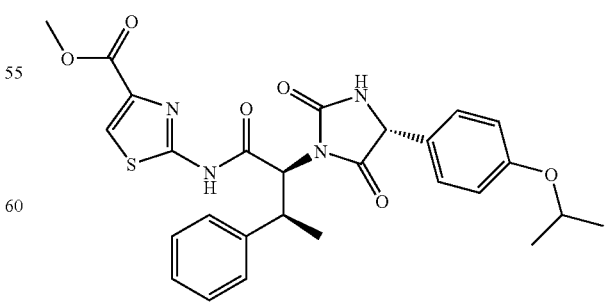

(R)-tert-Butoxycarbonylamino-[4-(1-methyl-ethoxy)-phenyl]-acetic acid, which was used in place of (R)-tert-butoxycarbonylamino-{4-[2-(tetrahydro-pyran-2-yloxy)-ethoxy]-phenyl}-acetic acid in Example 8e, was prepared in a similar manner as described for the synthesis of (R)-tert-butoxycarbonylamino-{4-[2-(tetrahydro-pyran-2-yloxy)-ethoxy]-phenyl}-acetic acid in Example 2b.

HRMS: Obs. Mass, 537.1803. Calcd. Mass, 537.1803 (M+H).

g) 2-{(2S,3S)-2-[(R)-4-(4-Methoxy-3-methyl-phenyl)-2,5-dioxo-imidazolidin-1-yl]-3-phenyl-butyrylamino}-thiazole-4-carboxylic acid methyl ester.

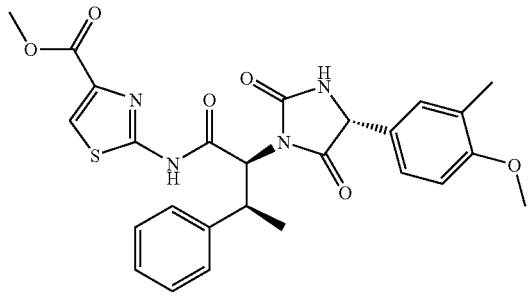

(R)-tert-Butoxycarbonylamino-(4-methoxy-3-methyl-phenyl)-acetic acid was prepared as follows.

(1) To a solution of (4-methoxy-3-methyl-phenyl)-acetic acid (5.04 g, 27.97 mmol) and triethylamine (3.9 mL, 27.97 mmol) in anhydrous tetrahydrofuran (100 mL) under nitrogen at −78° C. was added trimethylacetyl chloride (3.44 mL, 27.97 mmol). The reaction mixture was stirred at −78° C. for 10 minutes, 0° C. for 1 hour, then re-cooled to −78° C. At the same time, to a separate flask charged with a solution of (R)-(+)-4-benzyl-2-oxazolidinone (4.96 g, 27.97 mmol) in anhydrous tetrahydrofuran (100 mL) under nitrogen at −78° C. was added dropwise a solution of n-butyllithium (14 mL, 28 mmol, 2 M in hexanes). The second reaction mixture was stirred at −78° C. for 20 minutes, then transferred via cannula into the first reaction flask containing the mixed anhydride at −78° C. The reaction mixture was stirred at 0° C. for 1 hour, then warmed to room temperature and stirred for 18 hours. The mixture was quenched with saturated aqueous ammonium chloride solution (200 mL), concentrated to about half of its original volume under reduced pressure to remove tetrahydrofuran. The remaining mixture was extracted with ethyl acetate (2×250 mL). The organic layers were separated, combined, dried over sodium sulfate and concentrated under reduced pressure. The residue was purified by chromatography over silica gel eluted with 1:1 ethyl acetate/hexanes to give (R)-4-benzyl-3-[2-(4-methoxy-3-methyl-phenyl)-acetyl]-oxazolidin-2-one as a pale yellow oil (8.5 g, 89%).

(2) To a solution of (R)-4-benzyl-3-[2-(4-methoxy-3-methyl-phenyl)-acetyl]-oxazolidin-2-one (8.5 g, 25 mmol) in dry tetrahydrofuran (120 mL) under nitrogen at −78° C. was added potassium hexamethyldisilazide (36 mL, 32.6 mmol, 0.91M in tetrahydrofuran). The reaction mixture was stirred at −78° C. for 1 hour, then a pre-cooled solution of 2,4,6-triisopropylbenzenesulfonyl azide (8.8 g, 28.6 mmol) in tetrahydrofuran (80 mL) at −78° C. was added dropwise via cannula. The reaction mixture was stirred at −78° C. for 1.5 hours, then acetic acid (5.4 equiv, 8.2 g, 136 mmol) was added. The reaction mixture was warmed to 35° C. in a water bath and stirred for 2 hours, during which period of time analysis by thin layer chromatography indicated the formation of the desired product as a major component. The reaction mixture was concentrated to a smaller volume, then poured into water, and extracted with ethyl acetate (2×200 mL). The organic layers were separated, combined, dried over sodium sulfate and concentrated. The residue was purified by chromatography over silica gel eluted with 2:1 dichloromethane/hexanes to give (R)-3-[(R)-2-azido-2-(4-methoxy-3-methyl-phenyl)-acetyl]-4-benzyl-oxazolidin-2-one as a yellow oil (8.0 g, 84%).

(3) To a solution of (R)-3-[(R)-2-azido-2-(4-methoxy-3-methyl-phenyl)-acetyl]-4-benzyl-oxazolidin-2-one (8 g, 21 mmol) and di-tert-butyl dicarbonate (9.2 g, 42 mmol) in ethyl acetate (100 mL) was added 10% palladium on charcol (3 g) under nitrogen. The resulting suspension was vigorously shaken under hydrogen at 55 psi pressure in a Parr apparatus for 24 hours. The mixture was then filtered through a short pad of celite, and the filtrate was concentrated. The residue was purified by chromatography over silica gel eluted with 1:4 ethyl acetate/hexanes to give [(R)-2-((R)-4-benzyl-2-oxo-oxazolidin-3-yl)-1-(4-methoxy-3-methyl-phenyl)-2-oxo-ethyl]-carbamic acid tert-butyl ester as a yellow oil (6.05 g, 63%).

(4) To a solution of [(R)-2-((R)-4-benzyl-2-oxo-oxazolidin-3-yl)-1-(4-methoxy-3-methyl-phenyl)-2-oxo-ethyl]-carbamic acid tert-butyl ester (6.05 g, 13.3 mmol) in 4:1 tetrahydrofuran/water (200 mL) at −10° C. was added sequentially 30% aqueous hydrogen peroxide (15 mL, 133 mmol) and a solution of lithium hydroxide monohydrate (1.63 g, 40 mmol) in water (20 mL). The reaction mixture was stirred at −10° C., and the progress of the reaction was monitored by thin layer chromatography. After 4 hours, thin layer chromatography indicated almost complete consumption of starting material. Saturated aqueous sodium sulfite solution (100 mL) was added. The mixture was concentrated to half of its original volume under reduced pressure to remove tetrahydrofuran, then extracted with dichloromethane (2×100 mL). The aqueous layer was separated and acidified to pH=4 with aqueous citric acid solution, extracted with ethyl acetate (2×250 mL). The organic layers were separated, combined, dried over sodium sulfate, concentrated under reduced pressure and dried in vacuo to give (R)-tert-butoxycarbonylamino-(4-methoxy-3-methyl-phenyl)-acetic acid as a white foam (2.2 g, 58%).

HRMS: Obs. Mass, 523.1646. Calcd. Mass, 523.1646 (M+H).

h) 2-((2S,3S)-2-{(R)-4-[4-(Dimethoxy-phosphorylmethoxy)-phenyl]-2,5-dioxo-imidazolidin-1-yl}-3-phenyl-butyrylamino)-thiazole-4-carboxylic acid methyl ester.

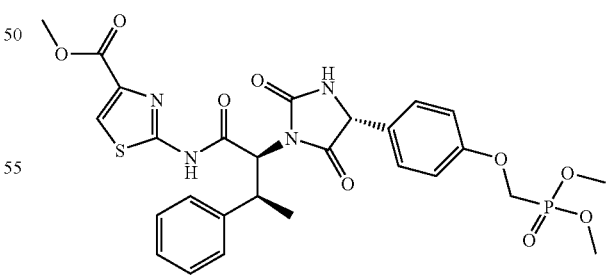

tert-Butoxycarbonylamino-[(R)-4-(dimethoxy-phosphorylmethoxy)-phenyl]-acetic acid was prepared as follows.

Dimethyl phosphite (2.0 g, 18.2 mmol), paraformaldehyde (574 mg, 19.1 mmol) and triethylamine (0.25 mL, 1.8 mmol) were combined and heated to 70° C. to give a clear solution. After 1 hour the reaction was cooled and concentrated in vacuo overnight to afford the crude hydroxymethyl-phosphonic acid dimethyl ester (2.5 g).

(2) To a solution of hydroxymethyl-phosphonic acid dimethyl ester (2.0 g, 14.5 mmol) in anhydrous dichloromethane (50 mL) at −20° C. was added pyridine (1.4 mL, 16.7 mmol) followed by trifluoromethanesulfonic anhydride (2.7 mL, 15.9 mmol). After stirring at 0° C. for 0.5 hours, the mixture was filtered through celite with a thin layer of silica gel. The filtrate was washed with cold 1.0 N aqueous hydrochloric acid, water, saturated aqueous sodium bicarbonate and dried over sodium sulfate. The solvents were removed to give trifluoro-methanesulfonic acid dimethoxy-phosphorylmethyl ester as an oil (2.1 g, 53%).

(3) Sodium hydride (18.9 mg, 0.79 mmol) was added to (R)-tert-butoxycarbonylamino-(4-hydroxy-phenyl)-acetic acid (100 mg, 0.37 mmol) in anhydrous dimethylformamide (2.5 mL) in an ice bath. The mixture was allowed to warm to room temperature followed by the addition of trifluoro-methanesulfonic acid dimethoxy-phosphorylmethyl ester (122 mg, 0.45 mmol). Stirring was continued overnight at room temperature. The reaction was poured into 0.2 M aqueous hydrochloric acid (10 mL) and the mixture extracted with ethyl acetate. The combined extracts were washed with saturated aqueous sodium bicarbonate, brine and dried over sodium sulfate. Evaporation of the solvents gave tert-butoxycarbonylamino-[(R)-4-(dimethoxy-phosphorylmethoxy)-phenyl]-acetic acid (120 mg, 83% yield).

HRMS: Obs. Mass, 617.1459. Calcd. Mass, 617.1466 (M+H).

i) 2-{(2S,3S)-3-(2-Methoxy-phenyl)-2-[4-(4-methoxy-phenyl)-2,5-dioxo-imidazolidin-1-yl]-butyrylamino}-thiazole-4-carboxylic acid methyl ester.

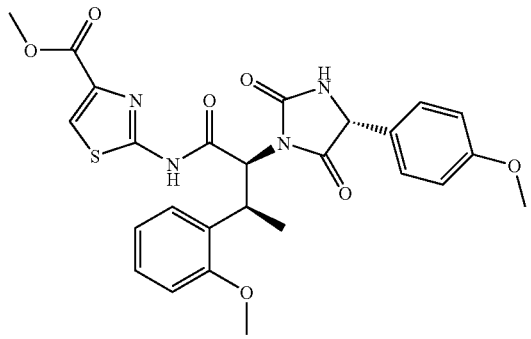

(2S,3S)-2-tert-Butoxycarbonylamino-3-(2-methoxy-phenyl)-butyric acid was prepared in a similar manner as the synthesis of (2S,3S)-2-tert-butoxycarbonylamino-3-phenyl-pentanoic acid as described in Example 3.

HRMS: Obs. Mass, 539.1591. Calcd. Mass, 539.1595 (M+H).

j) 2-((2S,3S)-3-(4-Fluoro-phenyl)-2-{(R)-4-[4-(2-methoxy-ethoxy)-phenyl]-2,5-dioxo-imidazolidin-1-yl}-butyrylamino)-thiazole-4-carboxylic acid methyl ester.

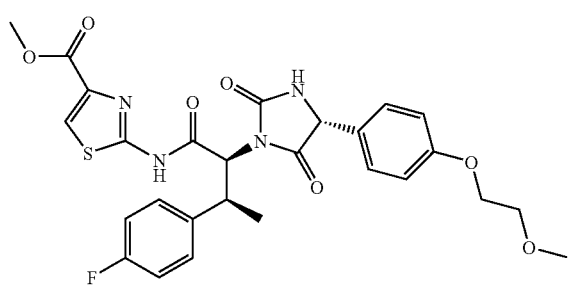

(2S,3S)-2-tert-Butoxycarbonylamino-3-(4-fluoro-phenyl)-butyric acid was prepared in a similar manner as the synthesis of (2S,3S)-2-tert-butoxycarbonylamino-3-phenyl-pentanoic acid as described in Example 3.

(R)-tert-Butoxycarbonylamino-[4-(2-methoxy-ethoxy)-phenyl]-acetic acid, which was used in place of (2R)-tert-butoxycarbonylamino-(2,3-dihydro-benzo[1,4]dioxin-6-yl)-acetic acid in Example 7 (step d), was prepared in a similar manner as described for the synthesis of (R)-tert-butoxycarbonylamino-{4-[2-(tetrahydro-pyran-2-yloxy)-ethoxy]-phenyl}-acetic acid in Example 2b.

HRMS: Obs. Mass, 571.1655. Calcd. Mass, 571.1657 (M+H).

k) 2-{(2S,3S)-2-[(R)-4-(4-Methoxy-phenyl)-2,5-dioxo-imidazolidin-1-yl]-3-methyl-pentanoylamino}-thiazole-4-carboxylic acid methyl ester.

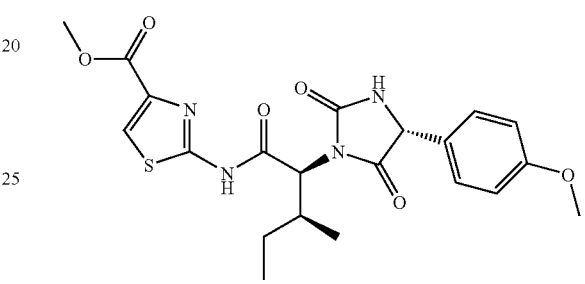

Prepared as described in Example 7 except that (2S,3S)-2-tert-butoxycarbonylamino-3-methyl-pentanoic acid was used in place of (2S,3S)-2-tert-butoxycarbonylamino-3-phenyl-butyric acid in step 2 and (R)-tert-butyloxycarbonylamino-4-methyoxyphenylglycine (prepared as described in example 1, step 5) was used in place of (2R)-tert-butoxycarbonylamino-(2,3-dihydro-benzo[1,4]dioxin-6-yl)-acetic acid in step 4.

HRMS: Obs. Mass, 483.1312. Calcd. Mass, 483.1309 (M+Na).

l) 2-[(2S,3S)-2-((R)-2,5-Dioxo-4-phenyl-imidazolidin-1-yl)-3-methyl-pentanoylamino]-thiazole-4-carboxylic acid methyl ester.

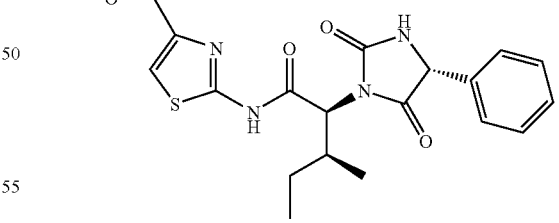

Prepared as described in Example 7 except that (2S,3S)-2-tert-butoxycarbonylamino-3-methyl-pentanoic acid was used in place of (2S,3S)-2-tert-butoxycarbonylamino-3-phenyl-butyric acid in step 2 and (R)-tert-butyloxycarbonylamino-phenylglycine was used in place of (2R)-tert-butoxycarbonylamino-(2,3-dihydro-benzo[1,4]dioxin-6-yl)-acetic acid in step 4.

HRMS: Obs. Mass, 453.1205 Calcd. Mass, 453.1203 (M+Na).

m) 2-((2S,3S)-2-{(R)-4-[4-(2-Methoxy-ethoxy)-phenyl]-2,5-dioxo-imidazolidin-1-yl}-3-methyl-pentanoylamino)-thiazole-4-carboxylic acid methyl ester.

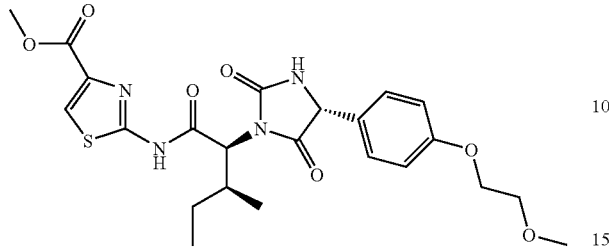

Prepared as described in Example 7 except that (2S,3S)-2-tert-butoxycarbonylamino-3-methyl-pentanoic acid was used in place of (2S,3S)-2-tert-butoxycarbonylamino-3-phenyl-butyric acid in step 2 and (R)-tert-butoxycarbonylamino-[4-(2-methoxy-ethoxy)-phenyl]-acetic acid (prepared as described in Example 2c) was used in place of (2R)-tert-butoxycarbonylamino-(2,3-dihydro-benzo[1,4]dioxin-6-yl)-acetic acid in step 4.

HRMS: Obs. Mass, 505.1758 Calcd. Mass, 505.1752 (M+H).

n) 2-{(2S,3R)-3-Hydroxy-2-[(R)-4-(4-methoxy-phenyl)-2,5-dioxo-imidazolidin-1-yl]-butyrylamino}-thiazole-4-carboxylic acid methyl ester.

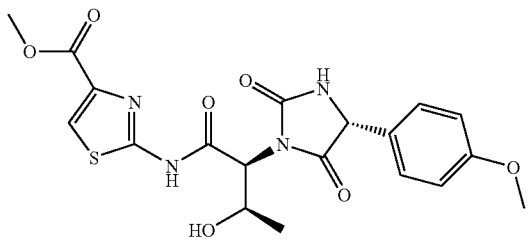

Prepared as described in Example 7 except that (2S,3R)-3-tert-butoxy-2-tert-butoxycarbonylamino-butyric acid was used in place of (2S,3S)-2-tert-butoxycarbonylamino-3-phenyl-butyric acid in step 2 and (R)-tert-butyloxycarbonylamino-4-methyoxyphenylglycine (prepared as described in example 1, step 5) was used in place of (2R)-tert-butoxycarbonylamino-(2,3-dihydro-benzo[1,4]dioxin-6-yl)-acetic acid in step 4. Prior to reaction with (R)-tert-butyloxycarbonylamino-4-methyoxyphenylglycine both tert-butyl groups were removed from 2-((2S,3R)-3-tert-butoxy-2-tert-butoxycarbonylamino-butyrylamino)-thiazole-4-carboxylic acid methyl ester with 1:1 v/v trifluoroacetic in methylene chloride at 0° C. for approximately 30 minutes. After removing the solvent the compound was dissolved in methylene chloride and washed with saturated sodium bicarbonate and saturated aqueous sodium chloride. The organic layer was dried over sodium sulfate filtered and concentrated. The crude product thus obtained was used without further purification.

HRMS: Obs. Mass, 449.1125 Calcd. Mass, 449.1126 (M+H).

o) 2-((2S,3R)-3-Hydroxy-2-{(R)-4-[4-(2-methoxy-ethoxy)-phenyl]-2,5-dioxo-imidazolidin-1-yl}-butyrylamino)-thiazole-4-carboxylic acid methyl ester.

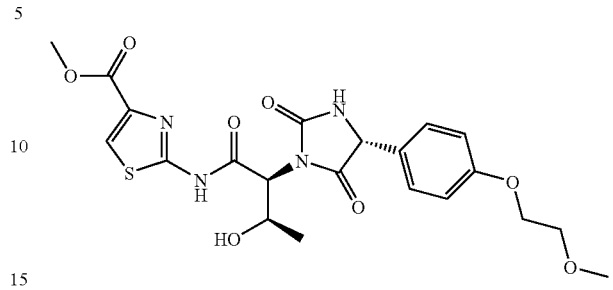

Prepared as described in Example 7 except that (2S,3R)-3-tert-butoxy-2-tert-butoxycarbonylamino-butyric acid was used in place of (2S,3S)-2-tert-butoxycarbonylamino-3-phenyl-butyric acid in step 2 and (R)-tert-butoxycarbonylamino-[4-(2-methoxy-ethoxy)-phenyl]-acetic acid (prepared as described in Example 2c) was used in place of (2R)-tert-butoxycarbonylamino-(2,3-dihydro-benzo[1,4]dioxin-6-yl)-acetic acid in step 4. Prior to reaction with (R)-tert-butoxycarbonylamino-[4-(2-methoxy-ethoxy)-phenyl]-acetic acid both tert-butyl groups were removed from 2-((2S,3R)-3-tert-butoxy-2-tert-butoxycarbonylamino-butyrylamino)-thiazole-4-carboxylic acid methyl ester with 1:1 v/v trifluoroacetic acid in methylene chloride at 0° C. for approximately 30 minutes. After removing the solvent the compound was dissolved in methylene chloride and washed with saturated aqueous sodium bicarbonate and saturated sodium chloride. The organic layer was dried over sodium sulfate filtered and concentrated. The crude product thus obtained was used without further purification.

HRMS: Obs. Mass, 515.1210 Calcd. Mass, 515.1207 (M+H).

p) 2-((2S,3R)-3-tert-Butoxy-2-{(R)-4-[4-(2-methoxy-ethoxy)-phenyl]-2,5-dioxo-imidazolidin-1-yl}-butyrylamino)-thiazole-4-carboxylic acid methyl ester.

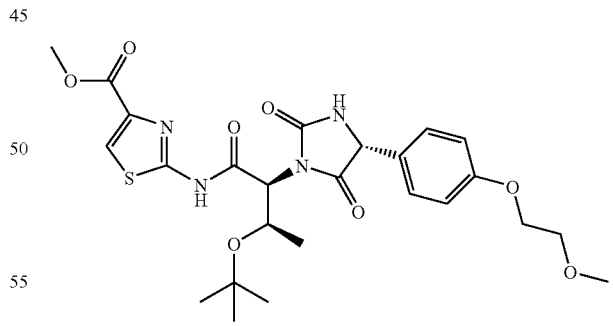

Prepared as described in Example 7 except that (2S,3R)-3-tert-butoxy-2-tert-butoxycarbonylamino-butyric acid was used in place of (2S,3S)-2-tert-butoxycarbonylamino-3-phenyl-butyric acid in step 2 and (R)-tert-butoxycarbonylamino-[4-(2-methoxy-ethoxy)-phenyl]-acetic acid (prepared as described in Example 2c) was used in place of (2R)-tert-butoxycarbonylamino-(2,3-dihydro-benzo[1,4]dioxin-6-yl)-acetic acid in step 4. Prior to reaction with (R)-tert-butoxycarbonylamino-[4-(2-methoxy-ethoxy)-phenyl]-acetic acid the carbamate tert-butyl group was removed from 2-((2S,3R)-3-tert-butoxy-2-tert-butoxycarbonylamino-butyrylamino)-thiazole-4-carboxylic acid methyl ester with 1:2 v/v trifluoroacetic acid in methylene chloride at 0° C. for approximately 30 minutes. Saturated aqueous sodium bicarbonate and ethyl acetate were added to the rapidly stirring reaction solution to quench the reaction. After further dilution with ethyl acetate and water the organic layer was separated and washed with saturated sodium chloride, dried over sodium sulfate filtered and concentrated.

HRMS: Obs. Mass, 549.2015 Calcd. Mass, 549.2014 (M+H).

q) 2-{(2S,3R)-3-Methoxy-2-[(R)-4-(4-methoxy-phenyl)-2,5-dioxo-imidazolidin-1-yl]-butyrylamino}-thiazole-4-carboxylic acid methyl ester.

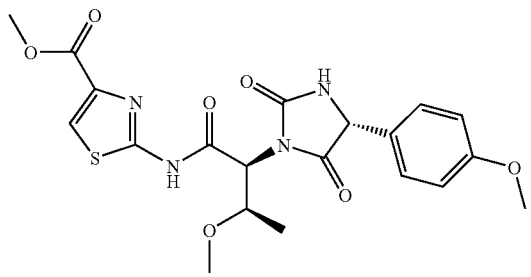

Prepared as described in Example 7 except that (2S,3R)-2-tert-butoxycarbonylamino-3-methoxy-butyric acid was used in place of (2S,3S)-2-tert-butoxycarbonylamino-3-phenyl-butyric acid in step 2 and (R)-tert-butyloxycarbonylamino-4-methyoxyphenylglycine (prepared as described in example 1, step 5) was used in place of (2R)-tert-butoxycarbonylamino-(2,3-dihydro-benzo[1,4]dioxin-6-yl)-acetic acid in step 4.

HRMS: Obs. Mass, 463.1284 Calcd. Mass, 463.1282 (M+H).

r) 2-((2S,3R)-3-Methoxy-2-{(R)-4-[4-(2-methoxy-ethoxy)-phenyl]-2,5-dioxo-imidazolidin-1-yl}-butyrylamino)-thiazole-4-carboxylic acid methyl ester.

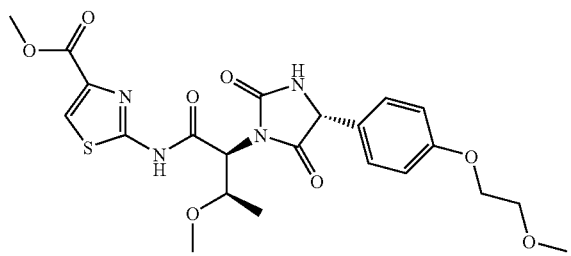

Prepared as described in Example 7 except that (2S,3R)-2-tert-butoxycarbonylamino-3-methoxy-butyric acid was used in place of (2S,3S)-2-tert-butoxycarbonylamino-3-phenyl-butyric acid in step 2 and (R)-tert-butoxycarbonylamino-[4-(2-methoxy-ethoxy)-phenyl]-acetic acid (prepared as described in Example 2c) was used in place of (2R)-tert-butoxycarbonylamino-(2,3-dihydro-benzo[1,4]dioxin-6-yl)-acetic acid in step 4.

HRMS: Obs. Mass, 507.1547 Calcd. Mass, 507.1544 (M+H).

s) 2-((2S,3R)-3-Benzyloxy-2-{(R)-4-[4-(2-methoxy-ethoxy)-phenyl]-2,5-dioxo-imidazolidin-1-yl}-butyrylamino)-thiazole-4-carboxylic acid methyl ester.

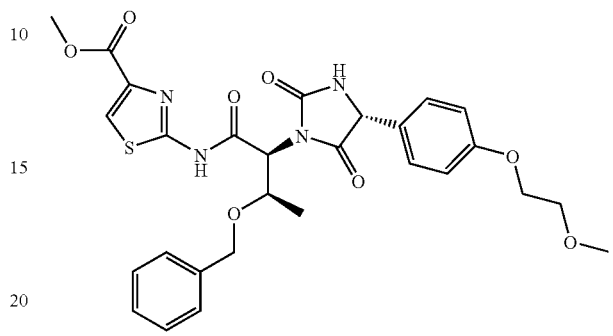

Prepared as described in Example 7 except that (2S,3R)-3-benzyloxy-2-tert-butoxycarbonylamino-butyric acid was used in place of (2S,3S)-2-tert-butoxycarbonylamino-3-phenyl-butyric acid in step 2 and (R)-tert-butoxycarbonylamino-[4-(2-methoxy-ethoxy)-phenyl]-acetic acid (prepared as described in Example 2c) was used in place of (2R)-tert-butoxycarbonylamino-(2,3-dihydro-benzo[1,4]dioxin-6-yl)-acetic acid in step 4.

HRMS: Obs. Mass, 583.1860 Calcd. Mass, 583.1857 (M+H).

t) 2-((2S,3R)-3-(4-Chloro-benzyloxy)-2-{(R)-4-[4-(2-methoxy-ethoxy)-phenyl]-2,5-dioxo-imidazolidin-1-yl}-butyrylamino)-thiazole-4-carboxylic acid methyl ester.

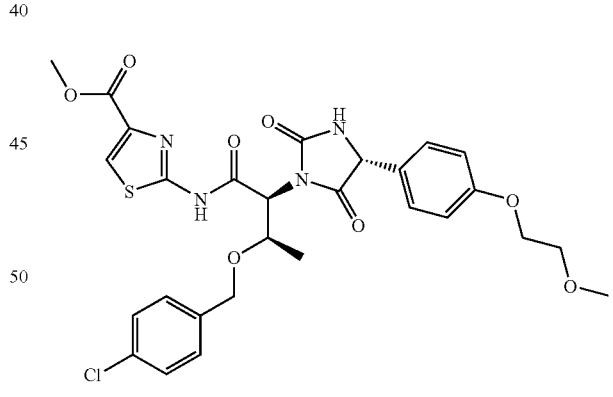

Prepared as described in Example 7 except that (2S,3R)-2-tert-butoxycarbonylamino-3-(4-chloro-benzyloxy)-butyric acid was used in place of (2S,3S)-2-tert-butoxycarbonylamino-3-phenyl-butyric acid in step 2 and (R)-tert-butoxycarbonylamino-[4-(2-methoxy-ethoxy)-phenyl]-acetic acid (prepared as described in Example 2c) was used in place of (2R)-tert-butoxycarbonylamino-(2,3-dihydro-benzo[1,4]dioxin-6-yl)-acetic acid in step 4.

HRMS: Obs. Mass, 617.1465 Calcd. Mass, 617.1468 (M+H).

u) 2-{(2S,3R)-2-[(R)-4-(4-Methoxy-phenyl)-2,5-dioxo-imidazolidin-1-yl]-3-methyl-pentanoylamino}-thiazole-4-carboxylic acid methyl ester.

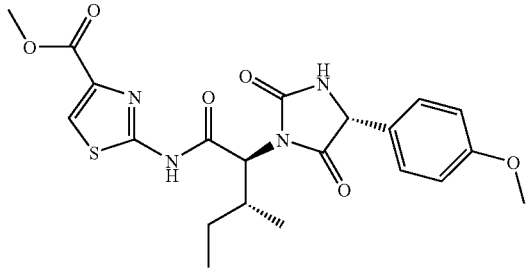

Prepared as described in Example 7 except that (2S,3R)-2-tert-butoxycarbonylamino-3-methyl-pentanoic acid was used in place of (2S,3S)-2-tert-butoxycarbonylamino-3-phenyl-butyric acid in step 2 and (R)-tert-butyloxycarbonylamino-4-methyoxyphenylglycine (prepared as described in Example 1, step 5) was used in place of (2R)-tert-butoxycarbonylamino-(2,3-dihydro-benzo[1,4]dioxin-6-yl)-acetic acid in step 4.

HRMS: Obs. Mass, 461.1490 Calcd. Mass, 461.1490 (M+H).

v) 2-((2S,3R)-2-{(R)-4-[4-(2-Methoxy-ethoxy)-phenyl]-2,5-dioxo-imidazolidin-1-yl}-3-methyl-pentanoylamino)-thiazole-4-carboxylic acid methyl ester.

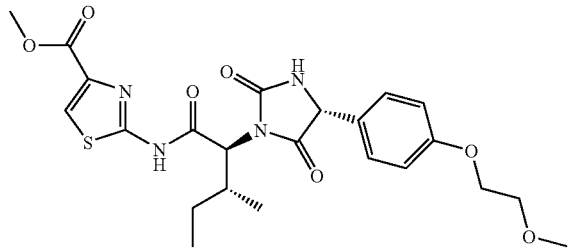

Prepared as described in Example 7 except that (2S,3R)-2-tert-butoxycarbonylamino-3-methyl-pentanoic acid was used in place of (2S,3S)-2-tert-butoxycarbonylamino-3-phenyl-butyric acid in step 2 and (R)-tert-butoxycarbonylamino-[4-(2-methoxy-ethoxy)-phenyl]-acetic acid (prepared as described in Example 2c) was used in place of (2R)-tert-butoxycarbonylamino-(2,3-dihydro-benzo[1,4]dioxin-6-yl)-acetic acid in step 4.

HRMS: Obs. Mass, 505.1754 Calcd. Mass, 505.1752 (M+H).

EXAMPLE 9

2-{(2S,3S)-2-[4-(4-Methanesulfonyl-phenyl)-2,5-dioxo-imidazolidin-1-yl]-3-phenyl-butyrylamino}-thiazole-4-carboxylic acid methyl ester

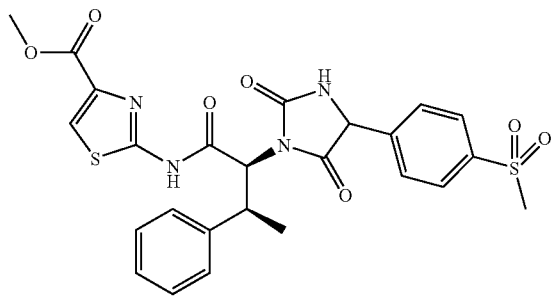

(1) A solution of 4-thiomethylbenzaldehyde (2.0 g, 13.00 mmol) in trimethylsilyl cyanide (7 mL, 52.5 mmol) was treated with a catalytic amount of zinc iodide and stirred at room temperature for 18 hours. The solvent was then removed under reduced pressure and the residue was dissolved a 7 N solution of ammonia in methanol (9 mL). The resulting mixture was heated at 45° C. for 2 hours in a sealed tube and then cooled to −20° C. The precipitated solid was collected by filtration, washed with ether, air dried and then dissolved in 6 N aqueous hydrochloric acid. The mixture was heated for 5 hours at 110° C. in a sealed tube and then cooled and concentrated under reduced pressure to give a solid residue. The solid was triturated with ether, air dried and suspended in dioxane. The suspension was treated with saturated aqueous sodium carbonate (10 mL) and di-tert-butyl dicarbonate (3.4 g, 15.6 mmol) and stirred overnight. The mixture was partitioned between ethyl acetate and 2 N aqueous hydrochloric acid. The organic layer was dried over sodium sulfate, filtered, concentrated and the solid residue was triturated with hexanes to afford tert-butoxycarbonylamino-(4-methylsulfanyl-phenyl)-acetic acid, as a yellow/brown solid (2.3 g, 59%).

(2) A solution of 2-((2S,3S)-2-amino-3-phenyl-butyrylamino)-thiazole-4-carboxylic acid methyl ester (75 mg, 0.24 mmol) and tert-butoxycarbonylamino-(4-methylsulfanyl-phenyl)-acetic acid (77 mg, 0.26 mmol) in dichloromethane (10 mL) at 0° C. was treated with 1-(3-dimethylaminopropyl)-3-ethylcarbodiimide hydrochloride (50 mg, 0.26 mmol). The reaction was allowed to slowly warm to room temperature and stirred for 60 hours. The mixture was then partitioned between ethyl acetate and water. The organic layer was dried over sodium sulfate, filtered and concentrated. The residue was purified by chromatography over silica gel gradient eluted up to 7:3 ethyl acetate/hexane. The material obtained after chromatography was further treated by precipitation of dichloromethane solution with excess of hexanes to give 2-{(2S,3S)-2-[2-tert-butoxycarbonylamino-2-(4-methylsulfanyl-phenyl)-acetylamino]-3-phenyl-butyrylamino}-thiazole-4-carboxylic acid methyl ester as a white amorphous solid (115 mg, 80%).

(3) 2-{(2S,3S)-2-[2-tert-Butoxycarbonylamino-2-(4-methylsulfanyl-phenyl)-acetylamino]-3-phenyl-butyrylamino}-thiazole-4-carboxylic acid methyl ester (110 mg, 0.18 mmol) was dissolved at 0° C. in a 30% solution of trifluoroacetic acid in dichloromethane. After 2.5 hours the reaction mixture was partitioned between ethyl acetate and aqueous saturated sodium bicarbonate. The aqueous layer was adjusted to pH=8 by the addition of solid sodium bicarbonate and then extracted twice with ethyl acetate. The combined organic layers were dried over sodium sulfate, filtered and concentrated to an off white solid. The solid was dissolved in a solution of diisopropyl ethyl amine (0.16 mL, 0.92 mmol) in dichloromethane (5 mL) and the resulting solution was added in a dropwise manner to a 0° C. mixture of diphosgene (16 µL, 0.13 mmol) in dichloromethane (5 mL). The mixture was stirred for 20 minutes and then partitioned between dichloromethane and water. The organic layer was dried over sodium sulfate, filtered and concentrated to the crude product. After purification by chromatography over silica gel gradient eluted up to 3:2 ethyl acetate/hexanes and precipitation of the material obtained from chromatography from dichloromethane with excess hexanes, 2-{(2S,3S)-2-[4-(4-methylsulfanyl-phenyl)-2,5-dioxo-imidazolidin-1-yl]-3-phenyl-butyrylamino}-thiazole-4-carboxylic acid methyl ester, was isolated as a white amorphous solid (45 mg, 46%).

(4) A solution of 2-{(2S,3S)-2-[4-(4-methylsulfanyl-phenyl)-2,5-dioxo-imidazolidin-1-yl]-3-phenyl-butyrylamino}-thiazole-4-carboxylic acid methyl ester (RO4919362-000) (40 mg, 0.08 mmol) in a 1:1 mixture of tetrahydrofuran and dichloromethane (20 mL) was treated with 3-chloroperbenzoic acid (75% purity) (40 mg, 0.17 mmol) at 0° C. After stirring for 30 minutes additional tetrahydrofuran (6 mL) was added and then the mixture was allowed to slowly warm to room temperature and was stirred for an additional 6 hours. The reaction mixture was then partitioned between ethyl acetate and aqueous saturated sodium carbonate. The organic layer was dried over sodium sulfate, filtered, concentrated and the residue was purified by chromatography over silica gel gradiet eluted up to 1:1 ethyl acetate in dichloromethane. Precipitation of the material obtained after chromatography from a dichloromethane solution with excess hexanes afforded 2-{(2S,3S)-2-[4-(4-methanesulfonyl-phenyl)-2,5-dioxo-imidazolidin-1-yl]-3-phenyl-butyrylamino}-thiazole-4-carboxylic acid methyl ester, as a white amorphous solid (29 mg, 65%).

HRMS: Obs. Mass, Calcd. Mass, (M+H).

EXAMPLE 10

2-{(S)-2-[(R)-4-(4-Methoxy-phenyl)-2,5-dioxo-imidazolidin-1-yl]-3-methyl-3-phenyl-butyrylamino}-thiazole-4-carboxylic acid methyl ester

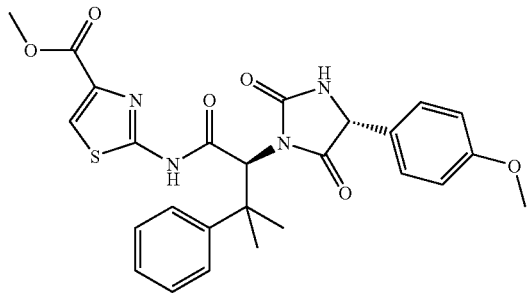

2-{(S)-2-[(R)-4-(4-Methoxy-phenyl)-2,5-dioxo-imidazolidin-1-yl]-3-methyl-3-phenyl-butyrylamino}-thiazole-4-carboxylic acid methyl ester was prepared in a similar manner as that described in Example 1 using (S)-N-tert-butoxycarbonyl-3,3-dimethylphenylalanine which was prepared according to the procedure of Nieman, J. A.; Coleman, J. E. et al. *J. Nat. Prod.* 2003, 66, 183-199.

HRMS: Obs. Mass, 523.1645. Calcd. Mass, 523.1646 (M+H).

EXAMPLE 11

2-{(2S,3R)-2-[(R)-4-(2,3-Dihydro-benzo[1,4]dioxin-6-yl)-2,5-dioxo-imidazolidin-1-yl]-3-phenyl-butyrylamino}-thiazole-4-carboxylic acid methyl ester.

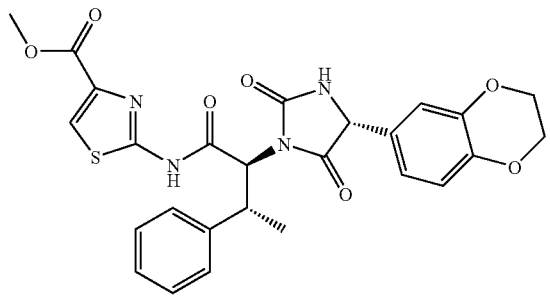

(1) Triethylamine (1.3 mL, 9.1 mmol) was added to (S)-3-phenylbutyric acid (1.0 g, 6.1 mmol) in anhydrous tetrahydrofuran (60 mL) at –78° C. followed by the dropwise addition of pivaloyl chloride (0.83 ml, 6.7 mmol) to give a white solid. The reaction was allowed to warm to room temperature for 10 minutes then cooled back down to –78° C. In a separate flask, n-butyllithium (4.6 mL, 11.6 mmol, 2.5 M F in hexanes) was added to (S)-(+)-4-phenyl-2-oxazolidinone (2.0 g, 12.2 mmol) in anhydrous tetrahydrofuran at –78° C. and allowed to stir for 10 minutes. The lithiated oxazolidinone was transfered via cannula to the mixed anhydride at –78° C. and stirring continued for 2 hours. The reaction was quenched with water (25 mL) and extracted with ethyl acetate. The combined extracts were washed with water, brine and dried over sodium sulfate. The crude product was purified by chromatography over silica gel eluted with 2:3 ethyl acetate/hexanes and the resulting solid was recrystallized from ethyl acetate/hexanes to afford (S)-4-phenyl-3-((S)-3-phenyl-butyryl)-oxazolidin-2-one (1.63 g, 88% yield).

(2) Potassium bis(trimethylsilyl)amide (2.0 mL, 1.8 mmol, 0.91 M in tetrahydrofuran) was added to (S)-4-phenyl-3-((S)-3-phenyl-butyryl)-oxazolidin-2-one (500 mg, 1.6 mmol) in anhydrous tetrahydrofuran (8 mL) at –78° C. and stirred for 1 hour. In a separate flask, a solution of 2,4,6-triisopropylbenzenesulphonyl azide (625 mg, 2.0 mmol) in anhydrous tetrahydrofuran (10 mL) at –78° C. was added via cannula to the anion at –78° C. and stirring continued for 2 hours. Acetic acid (0.45 mL, 7.8 mmol) was added to the reaction at –78° C., the mixture warmed to room temperature and stirred overnight. The mixture was poured into water (30 mL) and extracted with ethyl acetate. The combined extracts were washed with brine and dried over sodium sulfate. The crude product was purified on silica gel with 2:1 dichloromethane/hexane to give (S)-3-((2S,3R)-2-azido-3-phenyl-butyryl)-4-phenyl-oxazolidin-2-one (230 mg, 41%).

(3) To a solution of the (S)-3-((2S,3R)-2-azido-3-phenyl-butyryl)-4-phenyl-oxazolidin-2-one (595 mg, 1.7 mmol) in ethyl acetate (25 mL) was added di-tert-butyl dicarbonate (815 mg, 3.7 mmol) followed by 10% palladium on carbon (90 mg). The mixture was hydrogenated overnight at atmospheric pressure and room temperature. The mixture was filtered through celite and the solvent was removed to give [(1S,2R)-1-((S)-2-oxo-4-phenyl-oxazolidine-3-carbonyl)-2-phenyl-propyl]-carbamic acid tert-butyl ester as an oil (710 mg, 99%).

(4) To a solution of [(1S,2R)-1-((S)-2-oxo-4-phenyl-oxazolidine-3-carbonyl)-2-phenyl-propyl]-carbamic acid tert-butyl ester (710 mg, 1.7 mmol) in tetrahydrofuran (18 mL) and water (4 ml) at 0° C. was added 30% aqueous hydrogen peroxide (1.5 mL, 15.1 mmol) followed by 1M aqueous lithium hydroxide (5.0 mL, 5.0 mmol). The mixture was stirred overnight at room temperature. The excess hydrogen peroxide was quenched with 2.0 M aqueous sodium hydrogen sulfite (15 mL, 30.1 mmol). Stirring was continued for 1 hour followed by extraction with dichloromethane. The aqueous layer was acidified with 10% aqueous citric acid and extracted with ethyl acetate. The combined ethyl acetate extracts were washed with water, brine and dried over magnesium sulfate and evaporated to give (2S,3R)-2-tert-butoxycarbonylamino-3-phenyl-butyric acid (420 mg, 90% yield).

(5) In a manner similar as described in Example 1, 2-{(2S,3R)-2-[(R)-4-(2,3-dihydro-benzo[1,4]dioxin-6-yl)-2,5-dioxo-imidazolidin-1-yl]-3-phenyl-butyrylamino}-thiazole-4-carboxylic acid methyl ester was prepared from (2S,3R)-2-tert-butoxycarbonylamino-3-phenyl-butyric acid. HRMS: Obs. Mass, 537.1439. Calcd. Mass, 537.1439 (M+H).

EXAMPLE 12

2-{(2S,3S)-2-[(R)-4-(4-Acetylamino-phenyl)-2,5-dioxo-imidazolidin-1-yl]-3-phenyl-butyrylamino}-thiazole-4-carboxylic acid methyl ester.

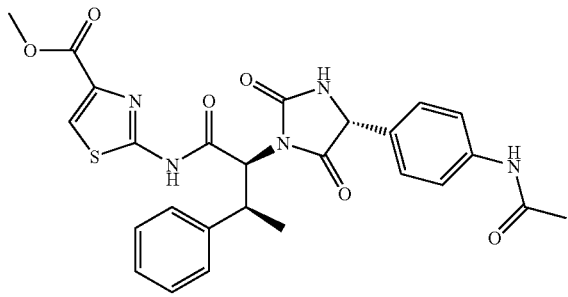

(1) To a solution of amino-(4-amino-phenyl)-acetic acid dihydrochloride (600 mg, 2.51 mmol) (prepared as described in U.S. Pat. No. 3,527,793) and triethylamine (1.1 mL, 7.53 mmol) in a 3:1 mixture of tetrahydrofuran/water (60 mL) was added di-tert-butyldicarbonate (1.4 g, 6.27 mmol). The reaction mixture was allowed to stir overnight and then partitioned between ethyl acetate and 1N aqueous hydrochloric acid. The organic layer was dried over sodium sulfate, filtered and concentrated. The residue was dissolved in a small amount of dichloromethane and precipitated with an excess of hexanes to afford (R)-tert-butoxycarbonylamino-(4-tert-butoxycarbonylamino-phenyl)-acetic acid as a white solid (730 mg, 79%).

HRMS: Obs. Mass, 389.1681. Calcd. Mass, 389.1683 (M+H).

(2) To a solution of (R)-tert-butoxycarbonylamino-(4-tert-butoxycarbonylamino-phenyl)-acetic acid (420 mg, 1.13 mmol) and (2S,3S)-2-(2-amino-3-phenyl-butyrylamino)-thiazole-4-carboxylic acid methyl ester (300 mg, 0.94 mmol) (prepared as described in Example 7) in dichloromethane (50 mL) was added 1-[3-(dimethylamino)propyl]-3-ethylcarbodiimide hydrochloride (220 mg, 1.13 mmol) at 0° C. The reaction mixture was allowed to warm to ambient temperature slowly, stirred overnight and then partitioned between dichloromethane and water. The organic layer was dried over sodium sulfate, filtered and concentrated to give the crude product. Purification by chromatography over silica gel gradient eluted between 0 and 60% ethyl acetate in hexanes followed by a precipitation of the product from dichloromethane with excess hexanes gave 2-{(2S,3S)-2-[(R)-2-tert-butoxycarbonylamino-2-(4-tert-butoxycarbonylamino-phenyl)-acetylamino]-3-phenyl-butyrylamino}-thiazole-4-carboxylic acid methyl ester as a white solid (520 mg, 82%).

HRMS: Obs. Mass, 668.2746. Calcd. Mass, 668.2749 (M+H).

(3) 2-{(2S,3S)-2-[(R)-2-tert-butoxycarbonylamino-2-(4-tert-butoxycarbonylamino-phenyl)-acetylamino]-3-phenyl-butyrylamino}-thiazole-4-carboxylic acid methyl ester (510 mg, 0.76 mmol) was dissolved in 30% v/v trifluoroacetic acid in dichloromethane solution (10 mL) at 0° C. The mixture was stirred at 0° C. for 2.5 hours and then partitioned between ethyl acetate and saturated aqueous sodium carbonate. The aqueous layer was adjusted to pH=9 by the addition of solid sodium carbonate and the organic layer collected, dried over sodium sulfate, filtered and concentrated. The residue was without further purification dissolved in tetrahydrofuran (50 mL) and the resulting solution cooled to 0° C. A solution of di-tert-butyldicarbonate (167 mg, 0.76 mmol) in tetrahydrofuran (5 mL) was added dropwise and after stirring overnight the reaction mixture was evaporated and the residue was purified by chromatography over silica gel gradient eluted with 0 to 100% ethyl acetate in hexanes to afford 2-{(2S,3S)-2-[(R)-2-(4-amino-phenyl)-2-tert-butoxycarbonylamino-acetylamino]-3-phenyl-butyrylamino}-thiazole-4-carboxylic acid methyl ester as a white solid (250 mg, 58%).

HRMS: Obs. Mass, 568.2223. Calcd. Mass, 568.2225 (M+H).

(4) To a cold solution of 2-{(2S,3S)-2-[(R)-2-(4-amino-phenyl)-2-tert-butoxycarbonylamino-acetylamino]-3-phenyl-butyrylamino}-thiazole-4-carboxylic acid methyl ester (100 mg, 0.177 mmol) in dichloromethane (10 mL) was added triethylamine (50 µL, 0.354 mmol) followed by acetic anhydride (22 µL 0.212 mmol). The reaction mixture was then stirred overnight at room temperature. The solvent was removed in vacuo and the residue was purified by chromatography over silica gel gradient eluted from 10% to 75% ethyl acetate in hexanes to afforded 2-{(2S,3S)-2-[(R)-2-(4-acetylamino-phenyl)-2-tert-butoxycarbonylamino-acetylamino]-3-phenyl-butyryl-amino}-thiazole-4-carboxylic acid methyl ester which was used immediately in the following step of the synthesis (107 mg, 98%).

(5) To a cold solution of 2-{(2S,3S)-2-[(R)-2-(4-acetylamino-phenyl)-2-tert-butoxycarbonylamino-acetylamino]-3-phenyl-butyryl-amino}-thiazole-4-carboxylic acid methyl ester (107 mg, 0.175 mmol) in dichloromethane (6 mL), was added trifluoroacetic acid (4 mL). The reaction mixture was stirred at room temperature for 45 minutes, followed by removal of volatiles in vacuo. To the residue was added diethyl ether (10 mL) and the resulting suspension was separated by centrifugation. The solid was dissolved in ethyl acetate and washed with saturated aqueous sodium bicarbonate. The aqueous layer was extracted with ethyl acetate (2×50 mL). The combined organic layers were dried over sodium sulfate, filtered and concentrated to give crude 2-{(2S,3S)-2-[(R)-2-(4-acetylamino-phenyl)-2-amino-acetylamino]-3-phenyl-butyrylamino}-thiazole-4-carboxylic acid methyl ester which was used immediately in the following step of the synthesis.

(6) Crude 2-{(2S,3S)-2-[(R)-2-(4-acetylamino-phenyl)-2-amino-acetylamino]-3-phenyl-butyrylamino}-thiazole-4-carboxylic acid methyl ester (≈0.175 mmol) was dissolved in dichloromethane (10 mL) and diisopropylethylamine (72 µL, 0.41 mmol) was added. The resulting mixture was added to an ice cooled solution of diphosgene (13 µL, 0.109 mmol) in dichloromethane (10 mL). The reaction mixture was stirred for 15 minutes, diluted with ethyl acetate (100 mL) and washed with 0.2M aqueous hydrochloric acid, saturated aqueous sodium bicarbonate, brine and dried over sodium sulfate. The solution was filtered and the solvent removed in vacu. The residue was purified by chromatography over silica gel gradient eluted from 50% to 100% ethyl acetate in hexanes to afford 2-{(2S,3S)-2-[(R)-4-(4-acetylamino-phenyl)-2,5-dioxo-imidazolidin-1-yl]-3-phenyl-butyrylamino}-thiazole-4-carboxylic acid methyl ester (70 mg, 74%).

HRMS: Obs. Mass, 536.1599. Calcd. Mass, 536.1599 (M+H).

EXAMPLE 13

N-[4-(1-Hydroxy-1-methyl-ethyl)-thiazol-2-yl]-2-[(R)-4-(4-methoxy-phenyl)-2,5-dioxo-imidazolidin-1-yl]-3-phenyl-butyramide

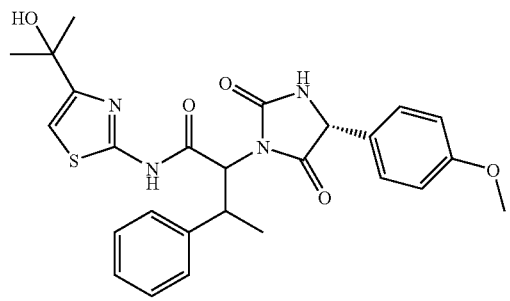

(1) (4-Acetyl-thiazol-2-yl)-carbamic acid tert-butyl ester was prepared in a similar manner as that described for (4-propionyl-thiazol-2-yl)-carbamic acid tert-butyl ester in example 4a-4d.

(2) (4-Acetyl-thiazol-2-yl)-carbamic acid tert-butyl ester (500 mg, 2.06 mmol) was taken in to dry tetrahydrofuran (8 mL) and cooled in an ice bath. To this was added a 3 M solution of methyl magnesium bromide (2.752 mL, 8.256 mmol) in diethyl ether over 5 minutes. After 30 minutes, more 3 M solution of methyl magnesium bromide (1 mL, 3 mmol) in diethyl ether was added. After 30 minutes, an additional aliquot of 3 M methyl magnesium bromide (1 mL, 3 mmol) in diethyl ether was added. No further change in the reaction mixture composition was observed after an additional 30 minutes. The reaction mixture was diluted with tetrahydrofuran (5 mL) and allowed to warm to room temperature. After 2 hours thin layer chromatography indicated no change in the composition of the reaction mixture. The reaction mixture was cooled in an ice bath and saturated aqueous ammonium chloride was added slowly. The mixture was diluted with water, extracted with ethyl acetate and washed with brine. The combined organic extracts were dried over sodium sulfate and concentrated to give a viscous oil. The crude product was purified by chromatography over silica gel gradient eluted from 1:19 upto 1:4 ethyl acetate/dichloromethane to give [4-(1-hydroxy-1-methyl-ethyl)-thiazol-2-yl]-carbamic acid tert-butyl ester as a white foam (250 mg, 47%).

(3) [4-(1-Hydroxy-1-methyl-ethyl)-thiazol-2-yl]-carbamic acid tert-butyl ester (250 mg, 0.92 mmol) was taken into dry dichloromethane and cooled in an ice bath. To this was added trifluoroacetic acid and the mixture stirred at 0° C. for 4 hours. The mixture was evaporated and the residue partitioned between dichloromethane and saturated aqueous sodium bicarbonate. The organic layer was separated out and the aqueous layer was extracted with dichloromethane. The combined organic extracts were dried over sodium sulfate and evaporated. Chromatography of the residue over silica gel gradient eluted with 1:99 up to 3:97 methanol in dichloromethane gave [4-(1-hydroxy-1-methyl-ethyl)-thiazol-2-yl]-carbamic acid (56 mg, 39%) as a white solid.

(4) N-[4-(1-Hydroxy-1-methyl-ethyl)-thiazol-2-yl]-2-[(R)-4-(4-methoxy-phenyl)-2,5-dioxo-imidazolidin-1-yl]-3-phenyl-butyramide was prepared from [4-(1-hydroxy-1-methyl-ethyl)-thiazol-2-yl]-carbamic acid and 2-tert-butoxycarbonylamino-3-phenyl-butyric acid in a similar manner as described in Example 1.

HRMS: Obs. Mass, 509.1853. Calcd. Mass, 509.1853 (M+H).

EXAMPLE 14

(2S,3S)-2-[(R)-4-(2,3-Dihydro-benzo[1,4]dioxin-6-yl)-2,5-dioxo-imidazolidin-1-yl]-N-[4-(1-hydroxy-propyl)-thiazol-2-yl]-3-phenyl-butyramide

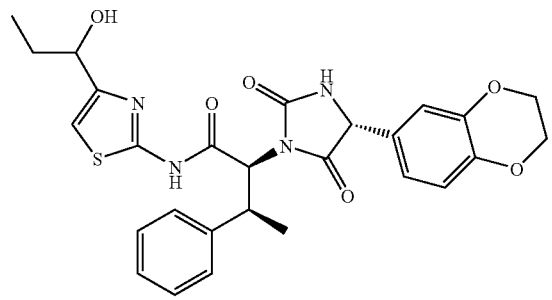

a) (2S,3S)-N-(4-Acetyl-thiazol-2-yl)-2-[(R)-4-(2,3-dihydro-benzo[1,4]dioxin-6-yl)-2,5-dioxo-imidazolidin-1-yl]-3-phenyl-N-(4-propionyl-thiazol-2-yl)-butyramide (from example 5a) (20 mg, 0.037 mmol) was dissolved in warm dry methanol (5 mL). The reaction mixture was then cooled in an ice bath and sodium borohydride (1.56 mg, 0.041 mmol) was added. The reaction was stirred at 5° C. for 30 minutes, additional sodium borohydride (1.56 mg, 0.041 mmol) was added and stirring continued for 1 hour. The clear solution was treated with 1.5 N aqueous potassium hydrogen phosphate (1 mL) and the cloudy mixture was stirred for a few minutes, then diluted with saturated brine and extracted with ethyl acetate (3×25 mL). The combined organic extracts were washed with saturated brine, dried over sodium sulfate and concentrated in vacuo. The pale yellow residue was taken into a small amount of dichloromethane (0.5 ml) then treated with diethyl ether (2 mL) and this turbid solution was further precipitated with of hexanes (3 mL). The mixture was stirred for 5 minutes then filtered over a 1.7 cm funnel, washed with hexanes and air dried to give (2S,3S)-2-[(R)-4-(2,3-dihydro-benzo[1,4]dioxin-6-yl]-2,5-dioxo-imidazolidin-1-yl]-N-[4-(1-hydroxy-propyl)-thiazol-2-yl]-3-phenyl-butyramide as a white solid (14.5 mg, 73%).

HRMS: Obs. Mass, 537.1801. Calcd. Mass, 537.1803 (M+H).

b) (2S,3S)-N-[4-(1-Hydroxy-ethyl)-thiazol-2-yl]-2-[(R)-4-(4-methoxy-phenyl)-2,5-dioxo-imidazolidin-1-yl]-3-phenyl-butyramide.

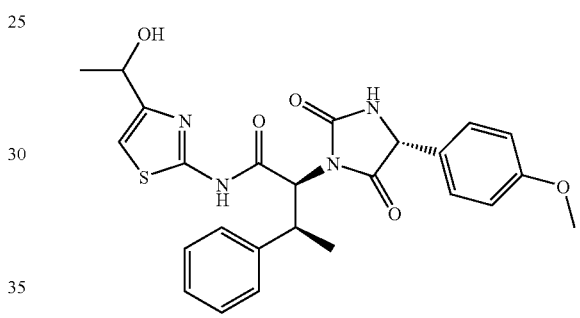

In a similar manner as that described in Example 14a, (2S,3S)-N-[4-(1-hydroxy-ethyl)-thiazol-2-yl]-2-[(R)-4-(4-methoxy-phenyl)-2,5-dioxo-imidazolidin-1-yl]-3-phenyl-butyramide was prepared from (2S,3S)-N-(4-acetyl-thiazol-2-yl)-2-[(R)-4-(4-methoxy-phenyl)-2,5-dioxo-imidazolidin-1-yl]-3-phenyl-butyramide which was in turn prepared as described in Example 1.

HRMS: Obs. Mass, Calcd. Mass, (M+H).

EXAMPLE 15

2-{(2S,3S)-2-[(R)-4-(4-Methoxy-phenyl)-2,5-dioxo-imidazolidin-1-yl]-3-phenyl-butyrylamino}-thiazole-4-carboxylic acid dimethylamide

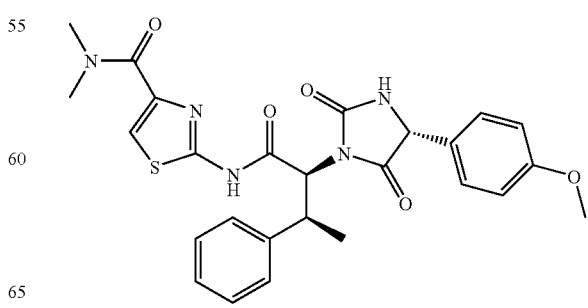

In a manner similar to that described in Example 1, 2-{(2S,3S)-2-[(R)-4-(4-methoxy-phenyl)-2,5-dioxo-imidazolidin-1-yl]-3-phenyl-butyrylamino}-thiazole-4-carboxylic acid dimethylamide was prepared from 2-amino-thiazole-4-carboxylic acid dimethylamide.

2-Amino-thiazole-4-carboxylic acid dimethylamide was prepared as follows. (1) A solution of 2-tert-butoxycarbonylamino-thiazole-4-carboxylic acid (0.5 g, 2 mmol) (prepared as described in Examples 4a and 4b) in thionyl chloride (10 mL) was heated at reflux (80° C.) for 2 hours. The reaction mixture was then concentrated under reduced pressure. To the residue was added a 2 M solution of dimethylamine in tetrahydrofuran (10 mL, 20 mmol) and methanol (10 mL). The reaction mixture was stirred at room temperature for 20 hours and concentrated. The residue was purified by chromatography over silica gel eluted with 2:1 ethyl acetate/hexanes to give (4-dimethylcarbamoyl-thiazol-2-yl)-carbamic acid tert-butyl ester as a yellow foam (0.26 g, 48%).

(2) To a solution of (4-dimethylcarbamoyl-thiazol-2-yl)-carbamic acid tert-butyl ester (0.26 g, 0.95 mmol) in dichloromethane (10 mL) was added trifluoroacetic acid (10 mL, 130 mmol). The reaction mixture was stirred at room temperature for 2 hours, then concentrated under reduced pressure. Saturated aqueous sodium bicarbonate solution (50 mL) was added to neutralize the residue. The mixture was extracted with ethyl acetate (2×100 mL). The organic layers were separated, combined and dried over sodium sulfate, concentrated under reduced pressure and dried in vacuo to give crude 2-amino-thiazole-4-carboxylic acid dimethylamide as a yellow gum which was used without further purification (0.14 g, 86%).

HRMS: Obs. Mass, 522.1803. Calcd. Mass, 522.1806 (M+H).

EXAMPLE 16

(2S,3S)-N-(4-Ethylsulfanyl-thiazol-2-yl)-2-{(R)-4-[4-(2-methoxy-ethoxy)-phenyl]-2,5-dioxo-imidazolidin-1-yl}-3-phenyl-butyramide

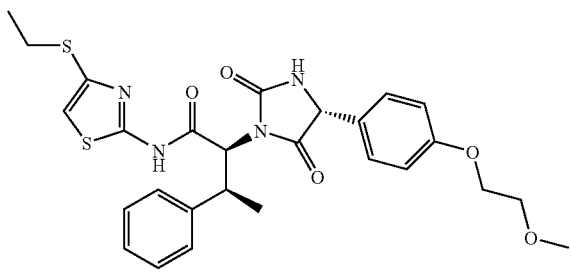

Prepared as described in Example 1 except that 4-ethylsulfanyl-thiazol-2-ylamine was used in place of 1-(2-amino-thiazol-4-yl)-ethanone and (R)-tert-butoxycarbonylamino-[4-(2-methoxy-ethoxy)-phenyl]-acetic acid (prepared as described in Example 2c) was used in place of (R)-tert-butyloxycarbonylamino-4-methyoxyphenylglycine. 4-Ethylsulfanyl-thiazol-2-ylamine was prepared as follows:

(1) N-tert-butoxycarbonyl-thiourea (0.600 g, 3.40 mmole) was suspended in ethanol (5 mL) and the mixture was cooled in an ice-water bath. To this mixture was added a solution of bromo-thioacetic acid S-ethyl ester (0.880 g [75% pure]; 3.61 mmole) in ethanol (5 mL). Following completion of the addition, the mixture was warmed to room temperature and stirred overnight. After 20 hours, the reaction was concentrated. The residue was partitioned between methylene chloride and water. The organic phase was washed with water and brine. The aqueous phases were then backwashed with methylene chloride. The two organic phases were combined, dried over sodium sulfate and concentrated. The crude material was purified by chromatography over silica gel eluted with 20% v/v ethyl acetate in hexanes, to give (4-ethylsulfanyl-thiazol-2yl)-carbamic acid tert-butyl ester (0.514 g, 58%).

(2) (4-Ethylsulfanyl-thiazol-2yl)-carbamic acid tert-butyl ester (0.583 g, 2.24 mmole) was dissolved in methylene chloride (9 mL) and the resulting solution was cooled in an ice-water bath. Trifluoroacetic acid (5 mL) was added dropwise to this solution. The solution was stirred under an argon atmosphere for 3 hours, allowing the cooling bath to slowly warm up. At the conclusion of the reaction, the bath temperature was 12° C. The reaction was concentrated. The residue was redissolved in methylene chloride and concentrated. This was repeated two additional times to remove most of the trifluoroacetic acid. Following the final concentration, the residue was dissolved again in methylene chloride and washed with saturated sodium bicarbonate, water and brine. The organic phase was dried over sodium sulfate and concentrated to yield 4-ethylsulfanyl-thiazol-2-ylamine (0.256 g, 65%).

HRMS: Obs. Mass, 555.1731. Calcd. Mass, 555.1731 (M+H).

EXAMPLE 17

(2S,3S)-N-(4-Ethanesulfinyl-thiazol-2-yl)-2-{(R)-4-[4-(2-methoxy-ethoxy)-phenyl]-2,5-dioxo-imidazolidin-1-yl}-3-phenyl-butyramide

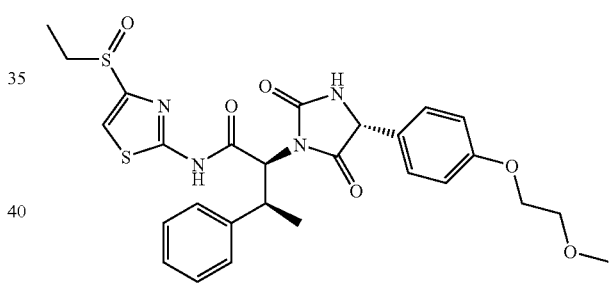

(2S,3S)-N-(4-Ethylsulfanyl-thiazol-2-yl)-2-{(R)-4-[4-(2-methoxy-ethoxy)-phenyl]-2,5-dioxo-imidazolidin-1-yl}-3-phenyl-butyramide (0.135 g, 0.24 mmole) (prepared as described in Example 16) was dissolved in anhydrous tetrahydrofuran (15 mL). To this solution was added a solution of m-chloroperbenzoic acid (0.066 g, 0.27 mmole) in tetrahydrofuran (8 mL). After stirring at room temperature for 30 minutes, the reaction was concentrated. The residue was dissolved in cold methylene chloride and washed twice with saturated sodium bicarbonate and twice with brine. Each aqueous phase was backwashed with a second portion of methylene chloride. The two organic phases were combined, dried over sodium sulfate and concentrated. The crude material was purified by chromatography over silica gel eluted with a gradient of 50-100% v/v ethyl acetate in hexanes followed by 5% v/v methanol in ethyl acetate to yield (2S,3S)-N-(4-ethanesulfinyl-thiazol-2-yl)-2-{(R)-4-[4-(2-methoxy-ethoxy)-phenyl]-2,5-dioxo-imidazolidin-1-yl}-3-phenyl-butyramide (0.103 g, 75%). This material was combined with another batch of material, dissolved in methylene chloride and added to hexanes to precipitate the product, (2S,3S)-N-(4-ethanesulfinyl-thiazol-2-yl)-2-{(R)-4-[4-(2-methoxy-ethoxy)-phenyl]-2,5-dioxo-imidazolidin-1-yl}-3-phenyl-butyramide (0.117 g).

HRMS: Obs. Mass, 571.1682. Calcd. Mass, 571.1680 (M+H).

EXAMPLE 18

(2S,3S)-N-(4-Ethanesulfonyl-thiazol-2-yl)-2-{(R)-4-[4-(2-methoxy-ethoxy)-phenyl]-2,5-dioxo-imidazolidin-1-yl}-3-phenyl-butyramide

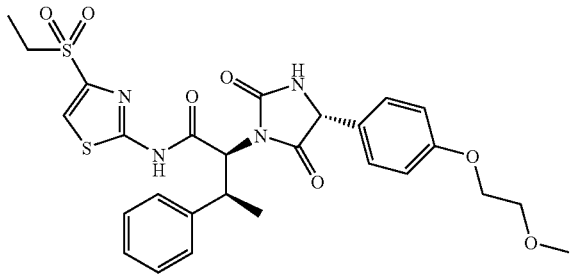

(2S,3S)-N-(4-Ethylsulfanyl-thiazol-2-yl)-2-{(R)-4-[4-(2-methoxy-ethoxy)-phenyl]-2,5-dioxo-imidazolidin-1-yl}-3-phenyl-butyramide (0.128 g, 0.23 mmole) (prepared as described in Example 16) was dissolved in anhydrous tetrahydrofuran (15 mL). To this solution was added a solution of m-chloroperbenzoic acid (0.133 g, 0.46 mmole) in tetrahydrofuran (8 mL). After stirring at room temperature for 18 minutes, the reaction was concentrated. The residue was dissolved in cold methylene chloride and washed twice with saturated aqueous sodium bicarbonate and twice with brine. Each aqueous phase was backwashed with a second portion of methylene chloride. The two organic phases were combined, dried over sodium sulfate and concentrated. The crude material was purified by chromatography over silica gel eluted with a gradient of 50-100% v/v ethyl acetate in hexanes followed by 5% v/v methanol in ethyl acetate. The pure fractions were combined and concentrated. The residue was dissolved in methylene chloride and the resulting solution was added to hexanes to precipitate out the product, (2S,3S)-N-(4-ethanesulfonyl-thiazol-2-yl)-2-{(R)-4-[4-(2-methoxy-ethoxy)-phenyl]-2,5-dioxo-imidazolidin-1-yl}-3-phenyl-butyramide (0.095 g, 68%).

HRMS: Obs. Mass, 587.1631. Calcd. Mass, 587.1629 (M+H).

EXAMPLE 19

(2S,3S)-N-[4-(2-Hydroxy-acetyl)-thiazol-2-yl]-2-{(R)-4-[4-(2-methoxy-ethoxy)-phenyl]-2,5-dioxo-imidazolidin-1-yl}-3-phenyl-butyramide

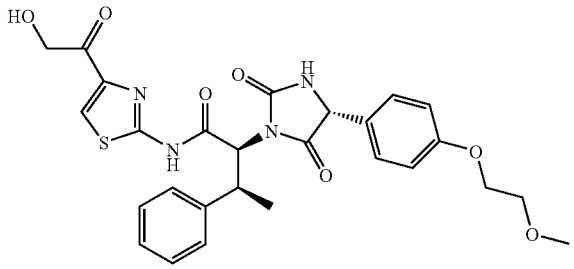

Prepared as described in Example 2c except that 1-(2-amino-thiazol-4-yl)-2-hydroxy-ethanone was used in place of 1-(2-amino-thiazol-4-yl)-ethanone. 1-(2-Amino-thiazol-4-yl)-2-hydroxy-ethanone was prepared as described below.

(1) Ethyl 2-aminothiazol-4-ylglyoxylate (4 g, 19.38 mmol) was taken into methanol (50 mL) and treated with p-toluenesulfonic acid (0.94 g, 0.25 mmol) at 85° C. for 1 hour. To this was added p-toluenesulfonic acid (3.1 g, 0.75 mmol) and stirring continued for 24 hours. p-Toluenesulfonic acid was added in 500 mg lots (2 more additions after 24 and 48 h) then stirred at 85° C. for 72 hours during which time NMR indicated >50% conversion to desired product. The reaction mixture was concentrated to ~10 mL and then diluted with ethyl acetate (200 mL) and washed 3 times with saturated aqueous sodium bicarbonate (~100 mL each) and saturated brine (100 mL). The aqueous layers were back extracted 3 times with ethyl acetate (100 mL each). The combined organic layers were dried over sodium sulfate, filtered and concentrated to give a yellow residue which was absorbed onto silica gel and purified by chromatography over a methanol deactivated silica gel column gradient eluted in 10% steps from 40 to 70% v/v ethyl acetate in hexanes and then with 100% ethyl acetate. The product containing fractions were pooled and concentrated in vacuo to give (2-amino-thiazol-4-yl)-dimethoxy-acetic acid methyl ester (1.73 g, 39%).

(2) A solution of (2-amino-thiazol-4-yl)-dimethoxy-acetic acid methyl ester (850 mg, 3.66 mmol) in dry tetrahydrofuran (40 mL) was treated portion-wise with lithium aluminum hydride (73 mg, 1.83 mmol) over 5 minutes at room temperature. The mixture was stirred for 30 minutes then treated portionwise with lithium aluminum hydride (36 mg 0.91 mmol) and stirred for 4 hours. After storing overnight in a refrigerator the reaction mixture was treated with ice chips (~10 g) then diluted with water (20 mL). The mixture was acidified with 2N aqueous sulfuric acid (~0.5 mL), then concentrated in vacuo to remove the tetrahydrofuran. The aqueous mixture was neutralized to pH 7.0 with saturated aqueous sodium bicarbonate and extracted with ethyl acetate (8×50 mL). The organic solution was washed with brine and dried over sodium sulfate, filtered and concentrated to give a tacky foam (650 mg). The residue was purified by chromatography over a methanol deactivated silica gel column gradient eluted in 1% steps between 0 and 6% methanol in methylene chloride. The product eluted from the column in 4 to 6% methanol in methylene chloride. After concentration 1-(2-amino-thiazol-4-yl)-2-hydroxy-ethanone was obtained as a yellow foam (210 mg, 28%).

HRMS: Obs. Mass, 553.1752. Calcd. Mass, 553.1752 (M+H).

EXAMPLE 20

(4-{(R)-1-[(1S,2S)-1-(4-Acetyl-thiazol-2-ylcarbamoyl)-2-phenyl-propyl]-2,5-dioxo-imidazolidin-4-yl}-phenoxy)-acetic acid methyl ester

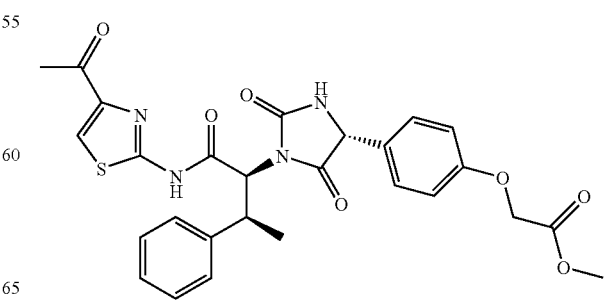

Prepared as described in example 1 except that (R)-tert-butoxycarbonylamino-(4-methoxycarbonylmethoxy-phenyl)-acetic acid was used in place of (R)-tert-butyloxycarbonylamino-4-methyoxyphenylglycine. (R)-tert-Butoxycarbonylamino-(4-methoxycarbonylmethoxy-phenyl)-acetic acid was prepared in a way similar to that described in example 1 except that methyl bromoacetate was used in place of methyl iodide.

HRMS: Obs. Mass, 551.1597. Calcd. Mass, 551.1595 (M+H).

EXAMPLE 21

(4-{(R)-2,5-Dioxo-1-[(1S,2S)-2-phenyl-1-(4-propionyl-thiazol-2-ylcarbamoyl)-propyl]-imidazolidin-4-yl}-phenoxy)-acetic acid methyl ester

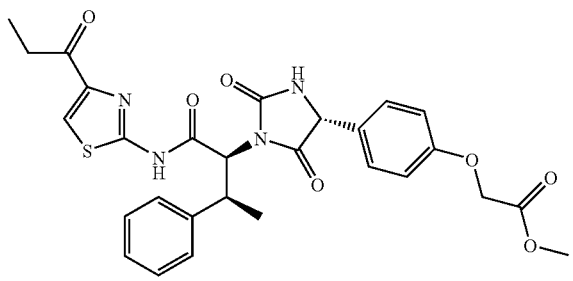

Prepared as described in example 4 except that (R)-tert-butoxycarbonylamino-(4-methoxycarbonylmethoxy-phenyl)-acetic acid was used in place of (R)-tert-butyloxycarbonylamino-4-methyoxyphenylglycine. (R)-tert-Butoxycarbonylamino-(4-methoxycarbonylmethoxy-phenyl)-acetic acid was prepared as described in example 20.

HRMS: Obs. Mass, 565.1754. Calcd. Mass, 565.1752 (M+H).

EXAMPLE 22

(4-{2,5-Dioxo-1-[(1S,2S)-2-phenyl-1-(4-propionyl-thiazol-2-ylcarbamoyl)-propyl]-imidazolidin-4-yl}-phenoxy)-acetic acid

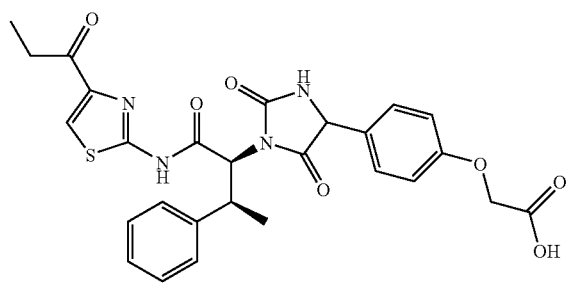

Prepared by hydrolysis of (4-{(R)-2,5-dioxo-1-[(1S,2S)-2-phenyl-1-(4-propionyl-thiazol-2-ylcarbamoyl)-propyl]-imidazolidin-4-yl}-phenoxy)-acetic acid methyl ester (prepared as described in example 21) with lithium hydroxide monohydrate in aqueous tetrahydrofuran. Under the conditions employed for the hydrolysis of the methyl ester racemization occurred at the 4-position of the imidazolidinedione ring.

HRMS: Obs. Mass, 551.1598. Calcd. Mass, 551.1595 (M+H).

EXAMPLE 23

(2S,3S)-N-(4-Acetyl-thiazol-2-yl)-2-[(R)-4-(4-dimethylcarbamoylmethoxy-phenyl)-2,5-dioxo-imidazolidin-1-yl]-3-phenyl-butyramide

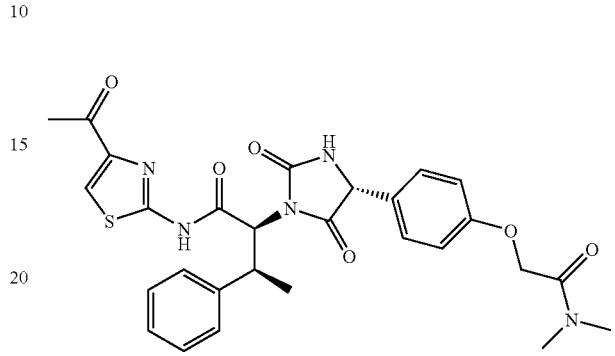

Prepared as described in example 1 except that (R)-tert-butoxycarbonylamino-(4-dimethylcarbamoylmethoxy-phenyl)-acetic acid was used in place of (R)-tert-butyloxycarbonylamino-4-methyoxyphenylglycine. (R)-tert-Butoxycarbonylamino-(4-dimethylcarbamoylmethoxy-phenyl)-acetic acid was prepared in a way similar to that described in example 1 except that the known compound 2-chloro-N,N-dimethyl-acetamide was used in place of methyl iodide.

HRMS: Obs. Mass, 564.1912. Calcd. Mass, 564.1912 (M+H).

EXAMPLE 24

In a manner similar to that described in Example 23, the following compounds were prepared.

a) (2S,3S)-N-(4-Acetyl-thiazol-2-yl)-2-[(R)-4-(4-methylcarbamoylmethoxy-phenyl)-2,5-dioxo-imidazolidin-1-yl]-3-phenyl-butyramide.

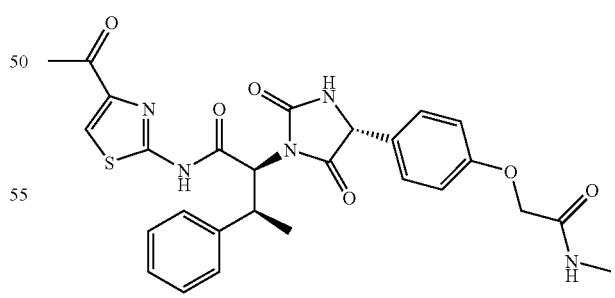

(R)-tert-Butoxycarbonylamino-(4-methylcarbamoylmethoxy-phenyl)-acetic acid was prepared and used in a manner analogous to that described for (R)-tert-butoxycarbonylamino-(4-dimethylcarbamoylmethoxy-phenyl)-acetic acid.

HRMS: Obs. Mass, 550.1757. Calcd. Mass, 550.1755 (M+H).

b) (2S,3S)-N-(4-Acetyl-thiazol-2-yl)-2-[(R)-4-(4-carbamoylmethoxy-phenyl)-2,5-dioxo-imidazolidin-1-yl]-3-phenyl-butyramide.

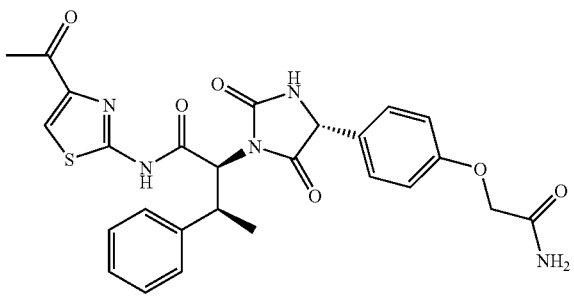

(R)-tert-Butoxycarbonylamino-(4-carbamoylmethoxy-phenyl)-acetic acid was prepared and used in a manner analogous to that described for (R)-tert-butoxycarbonylamino-(4-dimethylcarbamoylmethoxy-phenyl)-acetic acid.

HRMS: Obs. Mass, 532.1628. Calcd. Mass, 532.1625 (M+H).

c) (2S,3S)-N-(4-Acetyl-thiazol-2-yl)-2-((R)-4-{4-[(2-methoxy-ethylcarbamoyl)-methoxy]-phenyl}-2,5-dioxo-imidazolidin-1-yl)-3-phenyl-butyramide.

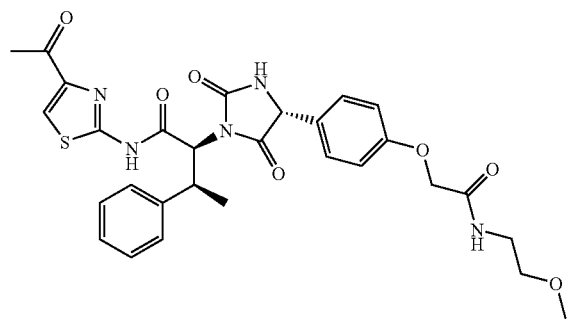

(R)-tert-Butoxycarbonylamino-{4-[(2-methoxy-ethylcarbamoyl)-methoxy]-phenyl}-acetic acid was prepared and used in a manner analogous to that described for (R)-tert-butoxycarbonylamino-(4-dimethylcarbamoylmethoxy-phenyl)-acetic acid.

HRMS: Obs. Mass, 594.2014. Calcd. Mass, 594.2017 (M+H).

d) (2S,3S)-N-(4-Acetyl-thiazol-2-yl)-2-{(R)-4-[4-(2-morpholin-4-yl-2-oxo-ethoxy)-phenyl]-2,5-dioxo-imidazolidin-1-yl}-3-phenyl-butyramide.

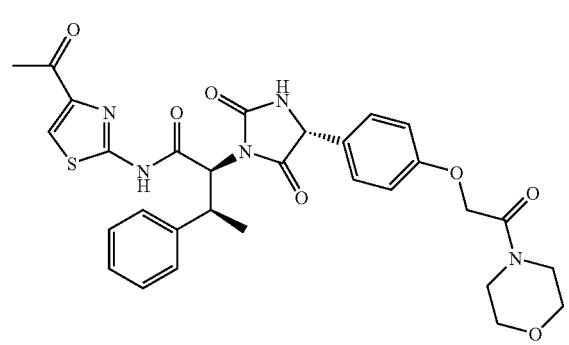

(R)-tert-Butoxycarbonylamino-[4-(2-morpholin-4-yl-2-oxo-ethoxy)-phenyl]-acetic acid was prepared and used in a manner analogous to that described for (R)-tert-butoxycarbonylamino-(4-dimethylcarbamoylmethoxy-phenyl)-acetic acid.

HRMS: Obs. Mass, 606.2009. Calcd. Mass, 606.2017 (M+H).

e) (2S,3S)-N-(4-Acetyl-thiazol-2-yl)-2-{(R)-2,5-dioxo-4-[4-(2-oxo-2-pyrrolidin-1-yl-ethoxy)-phenyl]-imidazolidin-1-yl}-3-phenyl-butyramide.

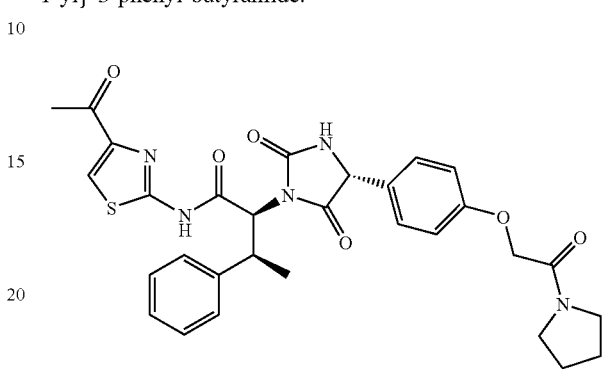

(R)-tert-Butoxycarbonylamino-[4-(2-oxo-2-pyrrolidin-1-yl-ethoxy)-phenyl]-acetic acid was prepared and used in a manner analogous to that described for (R)-tert-butoxycarbonylamino-(4-dimethylcarbamoylmethoxy-phenyl)-acetic acid.

HRMS: Obs. HRMS: Obs. Mass, 590.2063. Calcd. Mass, 590.2068 (M+H).

EXAMPLE 25

(2S,3S)-2-[(R)-4-(4-Dimethylcarbamoylmethoxy-phenyl)-2,5-dioxo-imidazolidin-1-yl]-3-phenyl-N-(4-propionyl-thiazol-2-yl)-butyramide

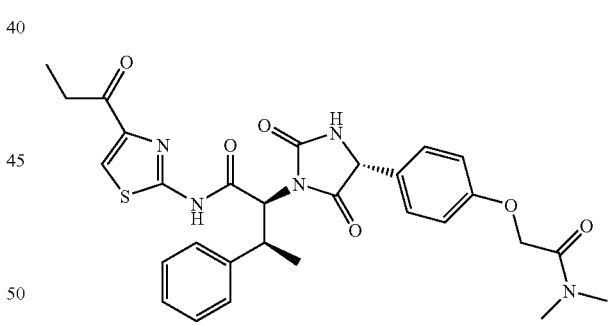

Prepared as described in Example 4 except that (R)-tert-butoxycarbonylamino-(4-dimethylcarbamoylmethoxy-phenyl)-acetic acid was used in place of (R)-tert-butyloxycarbonylamino-4-methyoxyphenylglycine. (R)-tert-butoxycarbonylamino-(4-dimethylcarbamoylmethoxy-phenyl)-acetic acid was prepared as described in Example 23.

HRMS: Obs. Mass, 578.2066. Calcd. Mass, 578.2068 (M+H).

EXAMPLE 26

In a manner similar to that described in Example 25, the following compounds were prepared.

a) (2S,3S)-2-[(R)-4-(4-Methylcarbamoylmethoxy-phenyl)-2,5-dioxo-imidazolidin-1-yl]-3-phenyl-N-(4-propionyl-thiazol-2-yl)-butyramide.

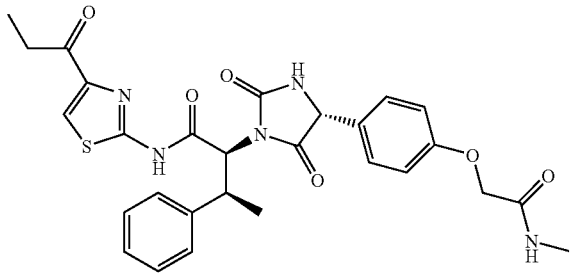

(R)-tert-Butoxycarbonylamino-(4-methylcarbamoyl-methoxy-phenyl)-acetic acid was prepared as described in Example 24a.

HRMS: Obs. Mass, 5641915. Calcd. Mass, 564.1912 (M+H).

b) (2S,3S)-2-[(R)-4-(4-Carbamoylmethoxy-phenyl)-2,5-dioxo-imidazolidin-1-yl]-3-phenyl-N-(4-propionyl-thiazol-2-yl)-butyramide.

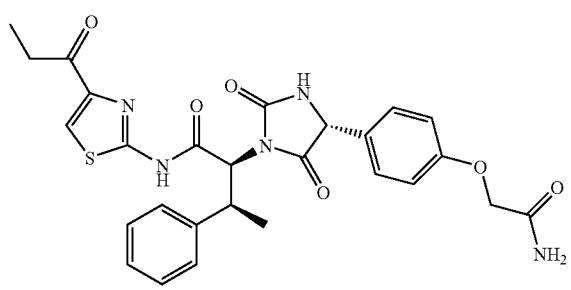

(R)-tert-Butoxycarbonylamino-(4-carbamoylmethoxy-phenyl)-acetic acid was prepared as described in Example 24b.

HRMS: Obs. Mass, 550.1755. Calcd. Mass, 550.1755 (M+H).

c) (2S,3S)-2-((R)-4-{4-[(2-Methoxy-ethylcarbamoyl)-methoxy]-phenyl}-2,5-dioxo-imidazolidin-1-yl)-3-phenyl-N-(4-propionyl-thiazol-2-yl)-butyramide.

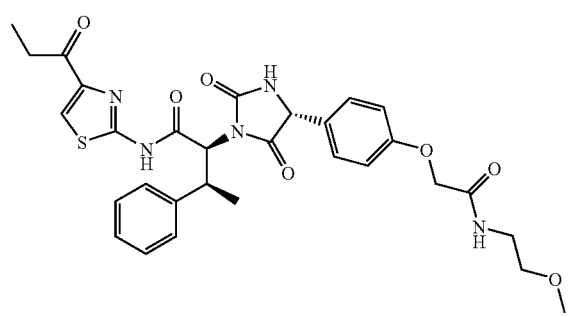

(R)-tert-Butoxycarbonylamino-{4-[(2-methoxy-ethylcarbamoyl)-methoxy]-phenyl}-acetic acid was prepared as described in Example 24c.

HRMS: Obs. Mass, 608.2169. Calcd. Mass, 608.2174 (M+H).

d) (2S,3S)-2-{(R)-4-[4-(2-Morpholin-4-yl-2-oxo-ethoxy)-phenyl]-2,5-dioxo-imidazolidin-1-yl}-3-phenyl-N-(4-propionyl-thiazol-2-yl)-butyramide.

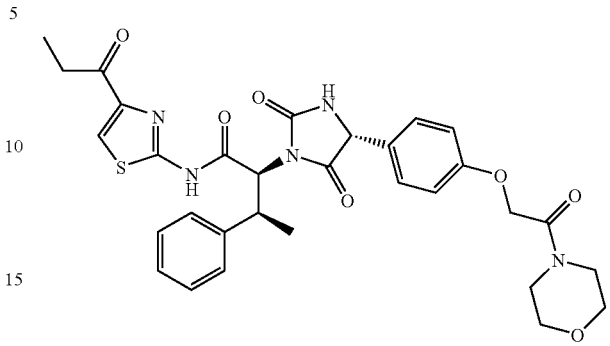

(R)-tert-Butoxycarbonylamino-[4-(2-morpholin-4-yl-2-oxo-ethoxy)-phenyl]-acetic acid was prepared as described in Example 24d.

HRMS: Obs. Mass, 620.2166. Calcd. Mass, 620.2174 (M+H).

e) (2S,3S)-2-{(R)-2,5-Dioxo-4-[4-(2-oxo-2-pyrrolidin-1-yl-ethoxy)-phenyl]-imidazolidin-1-yl}-3-phenyl-N-(4-propionyl-thiazol-2-yl)-butyramide.

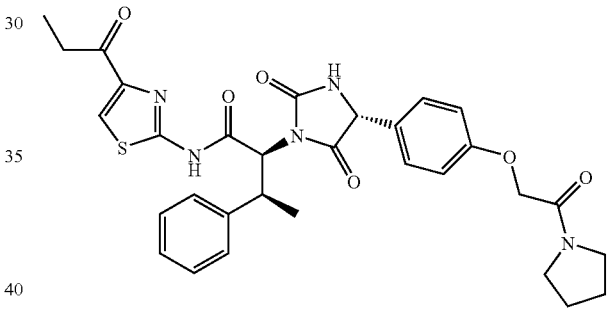

(R)-tert-Butoxycarbonylamino-[4-(2-oxo-2-pyrrolidin-1-yl-ethoxy)-phenyl]-acetic acid was prepared as described in Example 24e.

HRMS: Obs. Mass, 604.2222. Calcd. Mass, 604.2225 (M+H).

f) (2S,3S)-2-{(R)-4-[4-(2-Azetidin-1-yl-2-oxo-ethoxy)-phenyl]-2,5-dioxo-imidazolidin-1-yl}-3-phenyl-N-(4-propionyl-thiazol-2-yl)-butyramide.

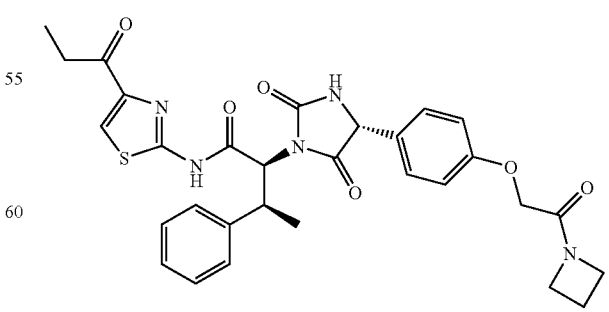

(R)-[4-(2-Azetidin-1-yl-2-oxo-ethoxy)-phenyl]-tert-butoxycarbonylamino-acetic acid was prepared and used in a manner analogous to that described for (R)-tert-butoxycarbonylamino-(4-dimethylcarbamoylmethoxy-phenyl)-acetic acid (prepared as described in Example 23).

HRMS: Obs. Mass, 612.1890. Calcd. Mass, 612.1887 (M+Na)

EXAMPLE 27

(2S,3S)-N-(4-Cyclopropanecarbonyl-thiazol-2-yl)-2-[(R)-4-(4-methylcarbamoylmethoxy-phenyl)-2,5-dioxo-imidazolidin-1-yl]-3-phenyl-butyramide

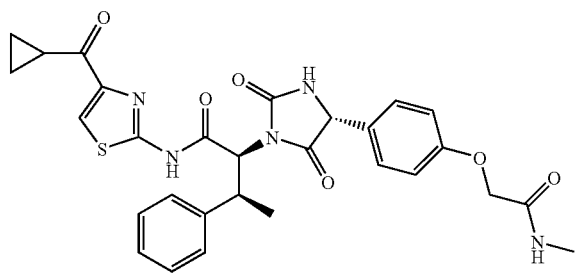

Prepared as described in example 5x except that (R)-tert-butoxycarbonylamino-(4-methylcarbamoylmethoxy-phenyl)-acetic acid (prepared as described in example 24a) was used in place of (R)-tert-butyloxycarbonylamino-4-methoxyphenylglycine.

HRMS: Obs. Mass, 576.1910. Calcd. Mass, 576.1912 (M+H).

Compound $IC_{50}$ Determination in MEK Cascade Assay

The evaluation of the compounds as MEK inhibitor was performed in a bead-based FP assay termed IMAP assay with MEK cascade components. In brief, the assay was performed in a reaction solution containing 10 mM HEPES, pH 7.0, 10 mM $MgCl_2$, 50 mM NaCl, 0.1 mM $NaVO_4$, and 1 m M DTT in the presence of 50 uM ATP, 0.45 nM c-RAF, 11.25 nM MEK, 90.5 nM ERK, and 0.5 μM FITC-labeled ERK (FITC-Aca-Ala-Ala-Ala-Thr-Gly-Pro-Leu-Ser-Pro-Gly-Pro-Phe-Ala-NH2). C-RAF, MEK, ERK and the ERK peptide substrates were added sequentially into the reaction buffer. Activated c-Raf phosphorylates MEK, activated MEK phosphorylates ERK, and subsequently activated ERK phosphrylates its peptide substrate. The FITC-labeled peptide substrates, when phosphorylated by the kinase, bind to nanoparticles derivatized with trivalent metal cations through a metal-phospholigand interaction. The result of this bound fluoresceinated phosphorylated product is an increase in polarization signal caused by a decrease in the molecular mobility of the bound product. Ten-point serial dilutions of the compounds were added into the MEK cascade assays before mixing with ERK and ERK peptide substrates. The reaction was incubated at 37° C. for 20 minutes for MEK activation, 20 minutes for ERK activation, 30 minutes for ERK peptide substrate phosphorylation, then was incubated overnight at room temperature for binding of IMAP beads. The IMAP assay was performed in a 384-well plate format. The changes in fluorescence polarization were measured by LJL instrument at 485 nm for excitation and 530 for emission. Polarization value (MP) was calculated as the following:

$$(MP)=1000\times(\text{intensity}_{vertical}-\text{intensity}_{horizontal})/(\text{intensity}_{vertical}+\text{intensity}_{horizontal}).$$

The $IC_{50}$ values were generated using Excel XLfit3 wizard. Percent activity and percent inhibition of reactions in the presence of a compound were calculated by comparing their MP values to those without a compound (as 100% activity). The compounds of formula I in the above assay exhibit $IC_{50}$ values of less than 25 micro molar.

What is claimed:

1. A compound of the formula

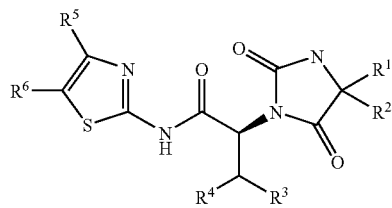

I wherein:
$R^1$ is selected from the group consisting of a substituted or unsubstituted aryl or a substituted or unsubstituted heteroaryl group;
$R^2$ is hydrogen
$R^3$ is selected from a mono- or di-alkyl group;
$R^4$ is selected from the group consisting of a substituted or unsubstituted aryl, hydroxyl, alkoxy, substituted alkoxy or a substituted or unsubstituted heteroaryl or alkyl group;
$R^5$ is selected from the group consisting of COOR, COR, $CON(R^7)_2$ or CHOHR wherein R is alkyl or alkyl substituted by an alkoxy group; and
$R^6$ and $R^7$ are selected from hydrogen or an alkyl group or the pharmaceutically acceptable salts or esters or prodrugs thereof.

2. The compound of claim 1 wherein $R^3$ is alkyl, $R^4$ is a substituted or unsubstituted aryl and $R^6$ is hydrogen.

3. The compound of claim 2 wherein $R^3$ is methyl and $R^4$ is substituted phenyl.

4. A compound selected from the group consisting of
(2S,3S)-N-(4-Acetyl-thiazol-2-yl)-2-[(R)-4-(4-methoxy-phenyl)-2,5-dioxo-imidazolidin-1-yl]-3-phenyl-butyramide;
(2S,3S)-N-(4-Acetyl-thiazol-2-yl)-2-[(R)-4-(4-hydroxy-phenyl)-2,5-dioxo-imidazolidin-1-yl]-3-phenyl-butyramide;
(2S,3S)-N-(4-Acetyl-thiazol-2-yl)-2-{(R)-4-[4-(2-hydroxy-ethoxy)-phenyl]-2,5-dioxo-imidazolidin-1-yl}-3-phenyl-butyramide;
(2S,3S)-N-(4-Acetyl-thiazol-2-yl)-2-{(R)-4-[4-(2-methoxy-ethoxy)-phenyl]-2,5-dioxo-imidazolidin-1-yl}-3-phenyl-butyramide;
(2S,3S)-N-(4-Acetyl-thiazol-2-yl)-2-((R)-4-{4-[2-(2-methoxy-ethoxy)-ethoxy]-phenyl}-2,5-dioxo-imidazolidin-1-yl)-3-phenyl-butyramide;
(2S,3S)-N-(4-Acetyl-thiazol-2-yl)-2-{(R)-4-[4-(2-ethoxy-ethoxy)-phenyl]-2,5-dioxo-imidazolidin-1-yl}-3-phenyl-butyramide;
(2S,3S)-N-(4-Acetyl-thiazol-2-yl)-2-{(R)-4-[4-(2-dimethylamino-ethoxy)-phenyl]-2,5-dioxo-imidazolidin-1-yl}-3-phenyl-butyramide; compound with trifluoro-acetic acid
(2S,3S)-N-(4-Acetyl-thiazol-2-yl)-2-{(R)-4-[4-(2-diethylamino-ethoxy)-phenyl]-2,5-dioxo-imidazolidin-1-yl}-3-phenyl-butyramide; compound with trifluoro-acetic acid (2S,3S)-N-(4-Acetyl-thiazol-2-yl)-2-[(R)-4-(4-ethoxy-phenyl)-2,5-dioxo-imidazolidin-1-yl]-3-phenyl-butyramide;

(2S,3S)-N-(4-Acetyl-thiazol-2-yl)-2-{(S)-4-[4-(2-dimethylamino-ethoxy)-phenyl]-2,5-dioxo-imidazolidin-1-yl}-3-phenyl-butyramide; compound with trifluoroacetic acid (4-{1-[(1S,2S)-1-(4-Acetyl-thiazol-2-ylcarbamoyl)-2-phenyl-propyl]-2,5-dioxo-imidazolidin-4-yl}-phenyl)-phosphonic acid diethyl ester;

(2S,3S)-N-(4-Acetyl-thiazol-2-yl)-2-[4-(4-dimethylamino-phenyl)-2,5-dioxo-imidazolidin-1-yl]-3-phenyl-butyramide;

(2S,3S)-2-[(R)-4-(4-Methoxy-phenyl)-2,5-dioxo-imidazolidin-1-yl]-3-phenyl-pentanoic acid (4-acetyl-thiazol-2-yl)-amide;

(2S,3S)-2-[(R)-4-(4-Methoxy-phenyl)-2,5-dioxo-imidazolidin-1-yl]-3-phenyl-N-(4-propionyl-thiazol-2-yl)-butyramide;

(2S,3S)-2-[(R)-4-(2,3-Dihydro-benzo[1,4]dioxin-6-yl)-2,5-dioxo-imidazolidin-1-yl]-3-phenyl-N-(4-propionyl-thiazol-2-yl)-butyramide;

(2S,3S)-2-[(R)-4-(4-Ethoxy-phenyl)-2,5-dioxo-imidazolidin-1-yl]-3-phenyl-N-(4-propionyl-thiazol-2-yl)-butyramide;

(2S,3S)-2-[(R)-4-(4-Hydroxy-phenyl)-2,5-dioxo-imidazolidin-1-yl]-3-phenyl-N-(4-propionyl-thiazol-2-yl)-butyramide;

(2S,3S)-2-{(R)-4-[4-(2-Methoxy-ethoxy)-phenyl]-2,5-dioxo-imidazolidin-1-yl}-3-phenyl-N-(4-propionyl-thiazol-2-yl)-butyramide;

(2S,3S)-2-{(S)-4-[4-(2-Methoxy-ethoxy)-phenyl]-2,5-dioxo-imidazolidin-1-yl}-3-phenyl-N-(4-propionyl-thiazol-2-yl)-butyramide;

(2S,3S)-2-{(R)-4-[4-(2-Hydroxy-ethoxy)-phenyl]-2,5-dioxo-imidazolidin-1-yl}-3-phenyl-N-(4-propionyl-thiazol-2-yl)-butyramide;

(2S,3S)-2-((R)-4-{4-[2-(2-Methoxy-ethoxy)-ethoxy]-phenyl}-2,5-dioxo-imidazolidin-1-yl)-3-phenyl-N-(4-propionyl-thiazol-2-yl)-butyramide, (2S,3S)-2-{(R)-4-[4-(2-Ethoxy-ethoxy)-phenyl]-2,5-dioxo-imidazolidin-1-yl]-3-phenyl-N-(4-propionyl-thiazol-2-yl)-butyramide, (2S,3S)-2-{(R)-4-[4-(2-Ethoxy-ethoxy)-phenyl]-2,5-dioxo-imidazolidin-1-yl]-3-phenyl-N-(4-propionyl-thiazol-2-yl)-butyramide;

(2S,3S)-2-{(R)-4-[4-(2-Dimethylamino-ethoxy)-phenyl]-2,5-dioxo-imidazolidin-1-yl}-3-phenyl-N-(4-propionyl-thiazol-2-yl)-butyramide; compound with trifluoroacetic acid (4-{(R)-2,5-Dioxo-1-[(1S,2S)-2-phenyl-1-(4-propionyl-thiazol-2-ylcarbamoyl)-propyl]-imidazolidin-4-yl}-phenoxymethyl)-phosphonic acid dimethyl ester;

(2S,3S)-N-(4-Isobutyryl-thiazol-2-yl)-2-{4-[4-(2-methoxy-ethoxy)-phenyl]-2,5-dioxo-imidazolidin-1-yl}-3-phenyl-butyramide;

(2S,3S)-N-(4-Isobutyryl-thiazol-2-yl)-2-[(R)-4-(4-methoxy-phenyl)-2,5-dioxo-imidazolidin-1-yl]-3-phenyl-butyramide;

(2S,3S)-2-{(S)-4-[4-(2-Dimethylamino-ethoxy)-phenyl]-2,5-dioxo-imidazolidin-1-yl}-3-phenyl-N-(4-propionyl-thiazol-2-yl)-butyramide; compound with trifluoroacetic acid;

(2S,3S)-2-{2,5-Dioxo-4-[4-(2-piperidin-1-yl-ethoxy)-phenyl]-imidazolidin-1-yl}-3-phenyl-N-(4-propionyl-thiazol-2-yl)-butyramide;

(2S,3S)-2-{4-[4-(2-Morpholin-4-yl-ethoxy)-phenyl]-2,5-dioxo-imidazolidin-1-yl}-3-phenyl-N-(4-propionyl-thiazol-2-yl)-butyramide;

(2S,3S)-3-(3-Fluoro-phenyl)-2-{(R)-4-[4-(2-methoxy-ethoxy)-phenyl]-2,5-dioxo-imidazolidin-1-yl}-N-(4-propionyl-thiazol-2-yl)-butyramide;

(2S,3S)-2-[(R)-4-(4-Methoxy-3-methyl-phenyl)-2,5-dioxo-imidazolidin-1-yl]-3-phenyl-N-(4-propionyl-thiazol-2-yl)-butyramide;

(2S,3S)-2-{(S)-4-[4-(2-Hydroxy-ethoxy)-phenyl]-2,5-dioxo-imidazolidin-1-yl}-3-phenyl-N-(4-propionyl-thiazol-2-yl)-butyramide;

(2S,3S)-2-((R)-2,5-Dioxo-4-phenyl-imidazolidin-1-yl)-3-phenyl-N-(4-propionyl-thiazol-2-yl)-butyramide;

(2S,3S)-2-[4-(4-Dimethylamino-phenyl)-2,5-dioxo-imidazolidin-1-yl]-3-phenyl-N-(4-propionyl-thiazol-2-yl)-butyramide;

(2S,3S)-2-[4-(4-Morpholin-4-yl-phenyl)-2,5-dioxo-imidazolidin-1-yl]-3-phenyl-N-(4-propionyl-thiazol-2-yl)-butyramide;

(2S,3S)-2-{4-[4-(4-Hydroxy-piperidin-1-yl)-phenyl]-2,5-dioxo-imidazolidin-1-yl}-3-phenyl-N-(4-propionyl-thiazol-2-yl)-butyramide;

(2S,3S)-2-(4-{4-[(2-Methoxy-ethyl)-methyl-amino]-phenyl}-2,5-dioxo-imidazolidin-1-yl)-3-phenyl-N-(4-propionyl-thiazol-2-yl)-butyramide;

(2S,3S)-N-(4-Cyclopropanecarbonyl-thiazol-2-yl)-2-{(R)-4-[4-(2-methoxy-ethoxy)-phenyl]-2,5-dioxo-imidazolidin-1-yl}-3-phenyl-butyramide;

(2S,3S)-2-{4-[4-(2-Methoxy-ethoxy)-phenyl]-2,5-dioxo-imidazolidin-1-yl}-3-methyl-pentanoic acid (4-propionyl-thiazol-2-yl)-amide;

(2S,3R)-3-Benzyloxy-2-{(R)-4-[4-(2-methoxy-ethoxy)-phenyl]-2,5-dioxo-imidazolidin-1-yl}-N-(4-propionyl-thiazol-2-yl)-butyramide;

(2S,3S)-N-[4-(2-Methoxy-acetyl)-thiazol-2-yl]-2-[(R)-4-(4-methoxy-phenyl)-2,5-dioxo-imidazolidin-1-yl]-3-phenyl-butyramide;

2-{(2S,3S)-2-[(R)-4-(2,3-Dihydro-benzo[1,4]dioxin-6-yl)-2,5-dioxo-imidazolidin-1-yl]-3-phenyl-butyrylamino}-thiazole-4-carboxylic acid methyl ester;

2-[(2S,3S)-2-((R)-2,5-Dioxo-4-phenyl-imidazolidin-1-yl)-3-phenyl-butyrylamino]-thiazole-4-carboxylic acid methyl ester;

2-{(2S,3S)-2-[(R)-4-(4-Methoxy-phenyl)-2,5-dioxo-imidazolidin-1-yl]-3-phenyl-butyrylamino}-thiazole-4-carboxylic acid methyl ester;

2-{(2S,3S)-2-[(R)-4-(4-Hydroxy-phenyl)-2,5-dioxo-imidazolidin-1-yl]-3-phenyl-butyrylamino}-thiazole-4-carboxylic acid methyl ester;

2-((2S,3S)-2-{(R)-4-[4-(2-Methoxy-ethoxy)-phenyl]-2,5-dioxo-imidazolidin-1-yl}-3-phenyl-butyrylamino)-thiazole-4-carboxylic acid methyl ester;

2-((2S,3S)-2-{(R)-4-[4-(2-Hydroxy-ethoxy)-phenyl]-2,5-dioxo-imidazolidin-1-yl}-3-phenyl-butyrylamino)-thiazole-4-carboxylic acid methyl ester;

2-{(2S,3S)-2-[(R)-4-(4-Isopropoxy-phenyl)-2,5-dioxo-imidazolidin-1-yl]-3-phenyl-butyrylamino}-thiazole-4-carboxylic acid methyl ester;

2-{(2S,3S)-2-[(R)-4-(4-Methoxy-3-methyl-phenyl)-2,5-dioxo-imidazolidin-1-yl]-3-phenyl-butyrylamino}-thiazole-4-carboxylic acid methyl ester;

2-((2S,3S)-2-{(R)-4-[4-(Dimethoxy-phosphoryl-methoxy)-phenyl]-2,5-dioxo-imidazolidin-1-yl}-3-phenyl-butyrylamino)-thiazole-4-carboxylic acid methyl ester;

2-{(2S,3S)-3-(2-Methoxy-phenyl)-2-[4-(4-methoxy-phenyl)-2,5-dioxo-imidazolidin-1-yl]-butyrylamino}-thiazole-4-carboxylic acid methyl ester;
2-((2S,3S)-3-(4-Fluoro-phenyl)-2-{(R)-4-[4-(2-methoxy-ethoxy)-phenyl]-2,5-dioxo-imidazolidin-1-yl}-butyrylamino)-thiazole-4-carboxylic acid methyl ester;
2-{(2S,3S)-2-[(R)-4-(4-Methoxy-phenyl)-2,5-dioxo-imidazolidin-1-yl]-3-methyl-pentanoylamino}-thiazole-4-carboxylic acid methyl ester;
2-[(2S,3S)-2-((R)-2,5-Dioxo-4-phenyl-imidazolidin-1-yl)-3-methyl-pentanoylamino]-thiazole-4-carboxylic acid methyl ester;
2-((2S,3S)-2-{(R)-4-[4-(2-Methoxy-ethoxy)-phenyl]-2,5-dioxo-imidazolidin-1-yl}-3-methyl-pentanoylamino)-thiazole-4-carboxylic acid methyl ester;
2-{(2S,3R)-3-Hydroxy-2-[(R)-4-(4-methoxy-phenyl)-2,5-dioxo-imidazolidin-1-yl]-butyrylamino}-thiazole-4-carboxylic acid methyl ester;
2-((2S,3R)-3-Hydroxy-2-{(R)-4-[4-(2-methoxy-ethoxy)-phenyl]-2,5-dioxo-imidazolidin-1-yl}-butyrylamino)-thiazole-4-carboxylic acid methyl ester;
2-((2S,3R)-3-tert-Butoxy-2-{(R)-4-[4-(2-methoxy-ethoxy)-phenyl]-2,5-dioxo-imidazolidin-1-yl}-butyrylamino)-thiazole-4-carboxylic acid methyl ester;
2-{(2S,3R)-3-Methoxy-2-[(R)-4-(4-methoxy-phenyl)-2,5-dioxo-imidazolidin-1-yl]-butyrylamino}-thiazole-4-carboxylic acid methyl ester;
2-((2S,3R)-3-Methoxy-2-{(R)-4-[4-(2-methoxy-ethoxy)-phenyl]-2,5-dioxo-imidazolidin-1-yl}-butyrylamino)-thiazole-4-carboxylic acid methyl ester;
2-((2S,3R)-3-Benzyloxy-2-{(R)-4-[4-(2-methoxy-ethoxy)-phenyl]-2,5-dioxo-imidazolidin-1-yl}-butyrylamino)-thiazole-4-carboxylic acid methyl ester;
2-((2S,3R)-3-(4-Chloro-benzyloxy)-2-{(R)-4-[4-(2-methoxy-ethoxy)-phenyl]-2,5-dioxo-imidazolidin-1-yl}-butyrylamino)-thiazole-4-carboxylic acid methyl ester;
2-{(2S3R)-2-[(R)-4-(4-Methoxy-phenyl)-2,5-dioxo-imidazolidin-1-yl]-3-methyl-pentanoylamino}-thiazole-4-carboxylic acid methyl ester;
2-((2S,3R)-2-{(R)-4-[4-(2-Methoxy-ethoxy)-phenyl]-2,5-dioxo-imidazolidin-1-yl}-3-methyl-pentanoylamino)-thiazole-4-carboxylic acid methyl ester;
2-((2S,3R)-2-{(R)-4-[4-(2-Methoxy-ethoxy)-phenyl]-2,5-dioxo-imidazolidin-1-yl}-3-methyl-pentanoylamino)-thiazole-4-carboxylic acid methyl ester;
2-{(2S,3S)-2-[4-(4-Methanesulfonyl-phenyl)-2,5-dioxo-imidazolidin-1-yl]-3-phenyl-butyrylamino}-thiazole-4-carboxylic acid methyl ester;
2-{(S)-2-[(R)-4-(4-Methoxy-phenyl)-2,5-dioxo-imidazolidin-1-yl]-3-methyl-3-phenyl-butyrylamino}-thiazole-4-carboxylic acid methyl ester;
2-{(2S,3R)-2-[(R)-4-(2,3-Dihydro-benzo[1,4]dioxin-6-yl)-2,5-dioxo-imidazolidin-1-yl]-3-phenyl-butyrylamino}-thiazole-4-carboxylic acid methyl ester;
2-{(2S,3S)-2-[(R)-4-(4-Acetylamino-phenyl)-2,5-dioxo-imidazolidin-1-yl]-3-phenyl-butyrylamino}-thiazole-4-carboxylic acid methyl ester;
N-[4-(1-Hydroxy-1-methyl-ethyl)-thiazol-2-yl]-2-[(R)-4-(4-methoxy-phenyl)-2,5-dioxo-imidazolidin-1-yl]-3-phenyl-butyramide;
(2S,3S)-2-[(R)-4-(2,3-Dihydro-benzo[1,4]dioxin-6-yl)-2,5-dioxo-imidazolidin-1-yl]-N-[4-(1-hydroxy-propyl)-thiazol-2-yl]-3-phenyl-butyramide;
(2S3S)-N-[4-(1-Hydroxy-ethyl)-thiazol-2-yl]-2-[(R)-4-(4-methoxy-phenyl)-2,5-dioxo-imidazolidin-1-yl]-3-phenyl-butyramide;
2-{(2S,3S)-2-[(R)-4-(4-Methoxy-phenyl)-2,5-dioxo-imidazolidin-1-yl]-3-phenyl-butyrylamino}-thiazole-4-carboxylic acid dimethylamide;
(2S,3S)-N-(4-Ethylsulfanyl-thiazol-2-yl)-2-{(R)-4-[4-(2-methoxy-ethoxy)-phenyl]-2,5-dioxo-imidazolidin-1-yl}-3-phenyl-butyramide;
(2S,3S)-N-(4-Ethanesulfinyl-thiazol-2-yl)-2-{(R)-4-[4-(2-methoxy-ethoxy)-phenyl]-2,5-dioxo-imidazolidin-1-yl}-3-phenyl-butyramide;
(2S,3S)-N-(4-Ethanesulfonyl-thiazol-2-yl)-2-{(R)-4-[4-(2-methoxy-ethoxy)-phenyl]-2,5-dioxo-imidazolidin-1-yl}-3-phenyl-butyramide;
(2S,3S)-N-[4-(2-Hydroxy-acetyl)-thiazol-2-yl]-2-{(R)-4-[4-(2-methoxy-ethoxy)-phenyl]-2,5-dioxo-imidazolidin-1-yl}-3-phenyl-butyramide;
(4-{(R)-1-[(1S,2S)-1-(4-Acetyl-thiazol-2-ylcarbamoyl)-2-phenyl-propyl]-2,5-dioxo-imidazolidin-4-yl}-phenoxy)-acetic acid methyl ester;
(4-{(R)-2,5-Dioxo-1-[(1S,2S)-2-phenyl-1-(4-propionyl-thiazol-2-ylcarbamoyl)-propyl]-imidazolidin-4-yl}-phenoxy)-acetic acid methyl ester;
(4-{2,5-Dioxo-1-[(1S,2S)-2-phenyl-1-(4-propionyl-thiazol-2-ylcarbamoyl)-propyl]-imidazolidin-4-yl}-phenoxy)-acetic acid;
(2S,3S)-N-(4-Acetyl-thiazol-2-yl)-2-[(R)-4-(4-dimethylcarbamoylmethoxy-phenyl)-2,5-dioxo-imidazolidin-1-yl]-3-phenyl-butyramide;
(2S,3S)-N-(4-Acetyl-thiazol-2-yl)-2-[(R)-4-(4-methylcarbamoylmethoxy-phenyl)-2,5-dioxo-imidazolidin-1-yl]-3-phenyl-butyramide;
(2S,3S)-N-(4-Acetyl-thiazol-2-yl)-2-[(R)-4-(4-carbamoylmethoxy-phenyl)-2,5-dioxo-imidazolidin-1-yl]-3-phenyl-butyramide;
(2S,3S)-N-(4-Acetyl-thiazol-2-yl)-2-((R)-4-{4-[(2-methoxy-ethylcarbamoyl)-methoxy]-phenyl}-2,5-dioxo-imidazolidin-1-yl)-3-phenyl-butyramide;
(2S,3S)-N-(4-Acetyl-thiazol-2-yl)-2-((R)-4-{4-[(2-methoxy-ethylcarbamoyl)-methoxy]-phenyl}-2,5-dioxo-imidazolidin-1-yl)-3-phenyl-butyramide;
(2S,3S)-N-(4-Acetyl-thiazol-2-yl)-2-((R)-4-{4-[(2-methoxy-ethylcarbamoyl)-methoxy]-phenyl}-2,5-dioxo-imidazolidin-1-yl)-3-phenyl-butyramide;
(2S,3S)-N-(4-Acetyl-thiazol-2-yl)-2-{(R)-4-[4-(2-morpholin-4-yl-2-oxo-ethoxy)-phenyl]-2,5-dioxo-imidazolidin-1-yl}-3-phenyl-butyramide;
(2S,3S)-N-(4-Acetyl-thiazol-2-yl)-2-{(R)-2,5-dioxo-4-[4-(2-oxo-2-pyrrolidin-1-yl-ethoxy)-phenyl]-imidazolidin-1-yl}-3-phenyl-butyramide;
(2S,3S)-2-[(R)-4-(4-Dimethylcarbamoylmethoxy-phenyl)-2,5-dioxo-imidazolidin-1-yl]-3-phenyl-N-(4-propionyl-thiazol-2-yl)-butyramide;
(2S,3S)-2-[(R)-4-(4-Methylcarbamoylmethoxy-phenyl)-2,5-dioxo-imidazolidin-1-yl]-3-phenyl-N-(4-propionyl-thiazol-2-yl)-butyramide;
(2S,3S)-2-((R)-4-{4-[(2-Methoxy-ethylcarbamoyl)-methoxy]-phenyl}-2,5-dioxo-imidazolidin-1-yl)-3-phenyl-N-(4-propionyl-thiazol-2-yl)-butyramide;
(2S,3S)-2-{(R)-4-[4-(2-Morpholin-4-yl-2-oxo-ethoxy)-phenyl]-2,5-dioxo-imidazolidin-1-yl}-3-phenyl-N-(4-propionyl-thiazol-2-yl)-butyramide;
(2S,3S)-2-{(R)-2,5-Dioxo-4-[4-(2-oxo-2-pyrrolidin-1-yl-ethoxy)-phenyl]-imidazolidin-1-yl}-3-phenyl-N-(4-propionyl-thiazol-2-yl)-butyramide;
(2S,3S)-2-{(R)-4-[4-(2-Azetidin-1-yl-2-oxo-ethoxy)-phenyl]-2,5-dioxo-imidazolidin-1-yl}-3-phenyl-N-(4-propionyl-thiazol-2-yl)-butyramide and
(2S,3S)-N-(4-Cyclopropanecarbonyl-thiazol-2-yl)-2-[(R)-4-(4-methylcarbamoylmethoxy-phenyl)-2,5-dioxo-imidazolidin-1-yl]-3-phenyl-butyramide.

5. A pharmaceutical composition comprising a compound of the formula

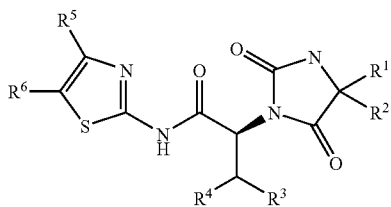

wherein:

R[1] is selected from the group consisting of a substituted or unsubstituted aryl or a substituted or unsubstituted heteroaryl group;

R[2] is hydrogen

R[3] is selected from a mono- or di-alkyl group;

R[4] is selected from the group consisting of a substituted or unsubstituted aryl, hydroxyl, alkoxy, substituted alkoxy or a substituted or unsubstituted heteroaryl or alkyl group;

R[5] is selected from the group consisting of COOR, COR, CON(R[7])$_2$ or CHOHR wherein R is alkyl or alkyl substituted by an alkoxy group; and R[6] and R[7] are selected from hydrogen or an alkyl group or the pharmaceutically acceptable salts or esters or prodrugs thereof and a pharmaceutically acceptable carrier.

* * * * *